United States Patent
Shechter et al.

(10) Patent No.: US 9,119,883 B2
(45) Date of Patent: Sep. 1, 2015

(54) REVERSIBLE PEGYLATED DRUGS

(71) Applicant: Yeda Research and Development Co., Ltd., Rehovot (IL)

(72) Inventors: Yoram Shechter, Rehovot (IL); Matityahu Fridkin, Rehovot (IL); Haim Tsubery, Elad (IL)

(73) Assignee: Yeda Research and Development Co., Ltd., Rehovot (IL)

( * ) Notice: Subject to any disclaimer, the term of this patent is extended or adjusted under 35 U.S.C. 154(b) by 0 days.

(21) Appl. No.: 14/468,672

(22) Filed: Aug. 26, 2014

(65) Prior Publication Data

US 2015/0057219 A1  Feb. 26, 2015

Related U.S. Application Data

(60) Division of application No. 14/146,396, filed on Jan. 2, 2014, now Pat. No. 8,877,709, which is a division of application No. 13/731,989, filed on Dec. 31, 2012, now Pat. No. 8,735,350, which is a division of application No. 12/540,169, filed on Aug. 12, 2009, now Pat. No. 8,343,910, which is a division of application No. 11/244,402, filed on Oct. 6, 2005, now Pat. No. 7,585,837, which is a continuation-in-part of application No. PCT/IL2004/000321, filed on Apr. 8, 2004.

(60) Provisional application No. 60/460,816, filed on Apr. 8, 2003.

(51) Int. Cl.
*A61K 47/48* (2006.01)
*A61K 38/22* (2006.01)
*C07D 207/404* (2006.01)
*C07D 207/416* (2006.01)
*C07D 207/452* (2006.01)
*C07D 403/12* (2006.01)
*A61K 38/26* (2006.01)
*A61K 38/28* (2006.01)

(52) U.S. Cl.
CPC .......... *A61K 47/48215* (2013.01); *A61K 38/22* (2013.01); *A61K 38/26* (2013.01); *A61K 38/28* (2013.01); *C07D 207/404* (2013.01); *C07D 207/416* (2013.01); *C07D 207/452* (2013.01); *C07D 403/12* (2013.01)

(58) Field of Classification Search
None
See application file for complete search history.

(56) References Cited

U.S. PATENT DOCUMENTS

| 6,504,005 | B1 | 1/2003 | Fridkin et al. |
| 7,585,837 | B2 | 9/2009 | Shechter et al. |
| 2002/0141985 | A1 | 10/2002 | Pittner et al. |

FOREIGN PATENT DOCUMENTS

WO  98/05361  12/1998

OTHER PUBLICATIONS

Zier, Andreas Doctoral Thesis presented at the Department of Chemistry of the University of Lausanne, Switzerland, 142 pages (1992).
A Zier et al. Tetrahedron Let. (1994) 25(7), pp. 1039-1042.
M. Mutter and D. Bellof. Helv. Chim. Acta (1984) 67, pp. 2009-2016.
Y. Schecter et al. Proc. Natl. Acad. Sci. USA. (2001) 98(3), pp. 1212-1217.
E. Gershonov et al. J. Med. Chem (2000) 43, pp. 2530-2537.
Y. Schecter et al. Biochem. Biophys. Res. Comm. (2003) 305, pp. 386-391.
Vettor, R et al "Effects of intravenous neuropeptide Y on insulin secretion and insulin sensitivity in skeletal muscle in normal rats" Diabetologia (1998) 41, pp. 1361-1367.
Gershonov, Eytan et al "New Concept for Long-Acting Insulin: Spontaneous Conversion of an Inactive Modified Insulin to the Active Hormone in Circulation: 9-Fluorenylmethoxycarbonyl Derivative of Insulin" Diabetes, vol. 48 (Jul. 1999) pp. 1437-1442.
Schechter, Yoram et at "N-[(2-Sulfo)-9-fluorenylmethoxycarbonyl].sub.3-gentamicin C.sub.1 Is a Long-Acting Prodrug Derivatives" J.Med.Chem. (2002) 45, pp. 4264-4270.
Greenwald, Richard B. et al "Effective drug delivery by PEGylated drug conjugates" Avanced Drug Delivery Reviews 55 (2003) pp. 217-250.
Greenwald, R.B. "PEG drugs: an overview" Journal of Controlled Release 74 (2001) pp. 159-171.

*Primary Examiner* — Thomas S Heard
(74) *Attorney, Agent, or Firm* — Browdy and Neimark, PLLC.

(57) ABSTRACT

Reversible pegylated drugs are provided by derivatization of free functional groups of the drug selected from amino, hydroxyl, mercapto, phosphate and/or carboxyl with groups sensitive to mild basic conditions such as 9-fluorenylmethoxycarbonyl (Fmoc) or 2-sulfo-9-fluorenylmethoxycarbonyl (FMS), to which group a PEG moiety is attached. In these pegylated drugs, the PEG moiety and the drug residue are not linked directly to each other, but rather both residues are linked to different positions of the scaffold Fmoc or FMS structure that is highly sensitive to bases and is removable under physiological conditions. The drugs are preferably drugs containing an amino group, most preferably peptides and proteins of low or medium molecular weight. Similar molecules are provided wherein a protein carrier or another polymer carrier replaces the PEG moiety.

12 Claims, 32 Drawing Sheets

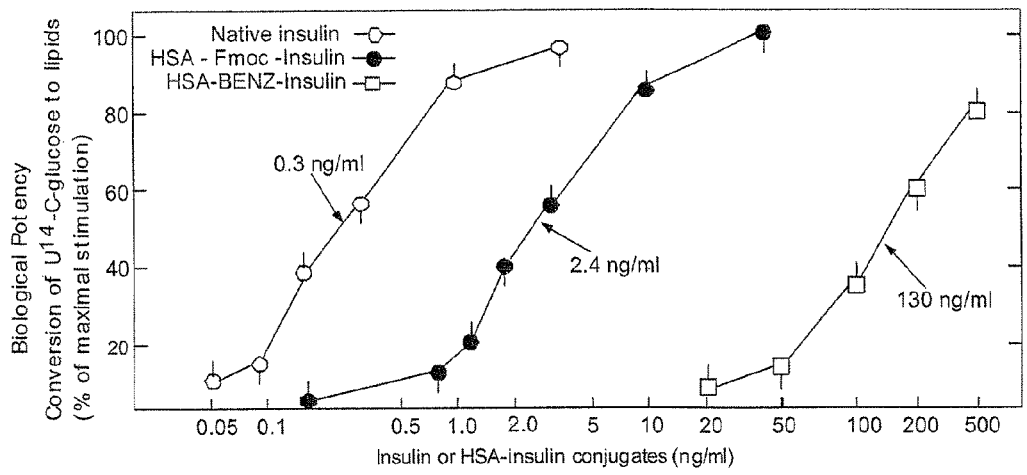
Fig. 26
Fig. 27A
Fig. 27B
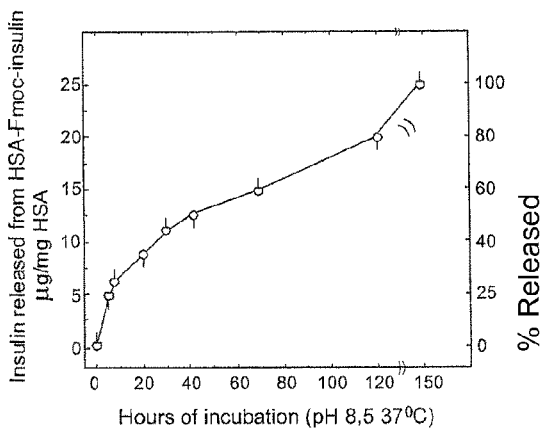
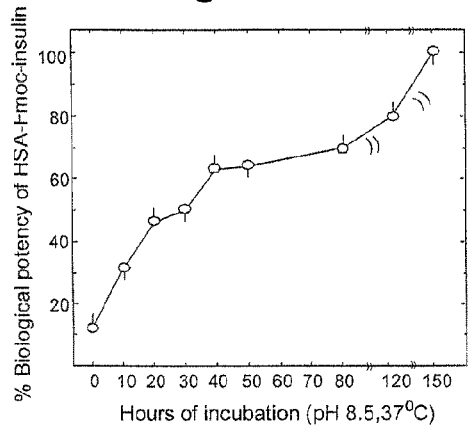

Fig. 28A
Fig. 28B
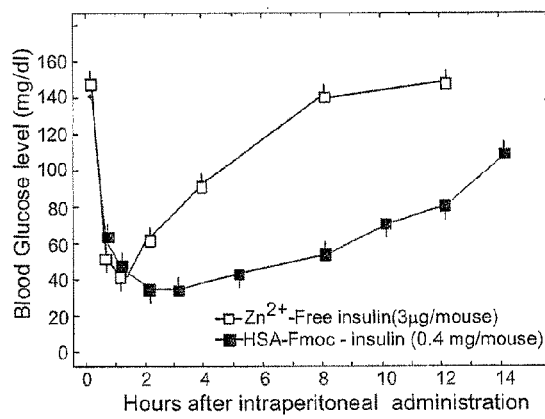
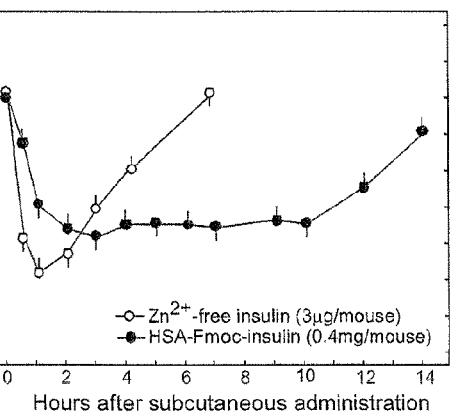

SEQUENCE LISTING

<160> NUMBER OF SEQ ID NOS: 14

<210> SEQ ID NO 1
<211> LENGTH: 39
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (39)..(39)
<223> OTHER INFORMATION: AMIDATION of the C-terminus residue

<400> SEQUENCE: 1

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 2
<211> LENGTH: 40
<212> TYPE: PRT
<213> ORGANISM: Artificial Sequence
<220> FEATURE:
<223> OTHER INFORMATION: Synthetic
<220> FEATURE:

```
<221> NAME/KEY: MOD_RES
<222> LOCATION: (40)..(40)
<223> OTHER INFORMATION: AMIDATION of the C-terminus residue

<400> SEQUENCE: 2

His Ser Asp Gly Thr Phe Ile Thr Ser Asp Leu Ser Lys Gln Met Glu
1               5                   10                  15

Glu Glu Ala Val Arg Leu Phe Ile Glu Trp Leu Lys Asn Gly Gly Pro
            20                  25                  30

Ser Ser Gly Ala Pro Pro Pro Ser
            35                  40

<210> SEQ ID NO 3
<211> LENGTH: 31
<212> TYPE: PRT
<213> ORGANISM: Artificial Sequence
<220> FEATURE:
<223> OTHER INFORMATION: Synthetic

<400> SEQUENCE: 3

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro
            20                  25                  30

<210> SEQ ID NO 4
<211> LENGTH: 31
<212> TYPE: PRT
<213> ORGANISM: Artificial Sequence
<220> FEATURE:
<223> OTHER INFORMATION: Synthetic

<400> SEQUENCE: 4

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Tyr
            20                  25                  30

<210> SEQ ID NO 5
<211> LENGTH: 30
<212> TYPE: PRT
<213> ORGANISM: Artificial Sequence
<220> FEATURE:
<223> OTHER INFORMATION: Synthetic

<400> SEQUENCE: 5

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly
            20                  25                  30

<210> SEQ ID NO 6
<211> LENGTH: 30
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (30)..(30)
<223> OTHER INFORMATION: AMIDATION of the C-terminus residue

<400> SEQUENCE: 6

His Gly Glu Gly Thr Phe Thr Ser Asp Leu Ser Lys Gln Met Glu Glu
1               5                   10                  15
```

```
Glu Ala Val Arg Leu Phe Ile Glu Trp Leu Lys Asn Gly Gly
            20                  25                  30

<210> SEQ ID NO 7
<211> LENGTH: 28
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (28)..(28)
<223> OTHER INFORMATION: AMIDATION of the C-terminus residue

<400> SEQUENCE: 7

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn
            20                  25

<210> SEQ ID NO 8
<211> LENGTH: 39
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (39)..(39)
<223> OTHER INFORMATION: AMIDATION of the C-terminus residue

<400> SEQUENCE: 8

His Gly Glu Gly Thr Phe Thr Ser Asp Leu Ser Lys Gln Leu Glu Glu
 1               5                  10                  15

Glu Ala Val Arg Leu Phe Ile Glu Phe Leu Lys Asn Gly Gly Pro Ser
            20                  25                  30

Ser Gly Ala Pro Pro Pro Ser
        35

<210> SEQ ID NO 9
<211> LENGTH: 28
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (28)..(28)
<223> OTHER INFORMATION: AMIDATION of the C-terminus residue

<400> SEQUENCE: 9

His Gly Glu Gly Thr Phe Thr Ser Asp Leu Ser Lys Gln Leu Glu Glu
 1               5                  10                  15

Glu Ala Val Arg Leu Phe Ile Glu Phe Leu Lys Asn
            20                  25

<210> SEQ ID NO 10
<211> LENGTH: 28
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (28)..(28)
<223> OTHER INFORMATION: AMIDATION of the C-terminus residue
```

```
<400> SEQUENCE: 10

His Gly Glu Gly Thr Phe Thr Ser Asp Leu Ser Lys Gln Leu Glu Glu
1               5                   10                  15

Glu Ala Val Arg Leu Ala Ile Glu Phe Leu Lys Asn
            20                  25

<210> SEQ ID NO 11
<211> LENGTH: 36
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (36)..(36)
<223> OTHER INFORMATION: AMIDATION of the C-terminus residue

<400> SEQUENCE: 11

Tyr Pro Ile Lys Pro Glu Ala Pro Gly Glu Asp Ala Ser Pro Glu Glu
1               5                   10                  15

Leu Asn Arg Tyr Tyr Ala Ser Leu Arg His Tyr Leu Asn Leu Val Thr
            20                  25                  30

Arg Gln Arg Tyr
        35

<210> SEQ ID NO 12
<211> LENGTH: 34
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (34)..(34)
<223> OTHER INFORMATION: AMIDATION of the C-terminus residue

<400> SEQUENCE: 12

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 13
<211> LENGTH: 28
<212> TYPE: PRT
<213> ORGANISM: Human
<220> FEATURE:
<221> NAME/KEY: DISULFID
<222> LOCATION: (7)..(23)
<223> OTHER INFORMATION: Cyclic peptide: disulfide bond from Cys at
      position 7 to Cys at position 23

<400> SEQUENCE: 13

Ser Leu Arg Arg Ser Ser Cys Phe Gly Gly Arg Met Asp Arg Ile Gly
1               5                   10                  15

Ala Gln Ser Gly Leu Gly Cys Asn Ser Phe Arg Tyr
            20                  25

<210> SEQ ID NO 14
<211> LENGTH: 27
<212> TYPE: PRT
<213> ORGANISM: Artificial Sequence
<220> FEATURE:
<223> OTHER INFORMATION: Synthetic
```

```
<400> SEQUENCE: 14

Ala Glu Ile Ser Gly Gln Leu Ser Tyr Val Arg Asp Val Asn Ser Trp
1               5                   10                  15

Gln His Ile Trp Thr Asn Val Ser Ile Glu Asn
            20                  25
```

REVERSIBLE PEGYLATED DRUGS

CROSS-REFERENCE TO RELATED APPLICATIONS

The present application is a division of allowed U.S. patent application Ser. No. 13/731,989, filed Dec. 31, 2012, which is a division of U.S. patent application Ser. No. 12/540,169, filed Aug. 12, 2009 (now U.S. Pat. No. 8,343,910, issued Jan. 1, 2013), which is a division of U.S. patent application Ser. No. 11/244,402 filed Oct. 6, 2005 (now U.S. Pat. No. 7,585,837, issued Sep. 8, 2009), such application being a Continuation-in-Part (CIP[1]) of International Application No. PCT/IL2004/000321, filed Apr. 8, 2004, which patent application claims the benefit of U.S. Provisional Appln. No. 60/460,816, filed Apr. 8, 2003, the entire contents of each of which are hereby incorporated by reference.

[1] Although the parent application is stated to be a OP, applicant does not concede that any matter is presented in this application which is not presented in the parent.

FIELD OF THE INVENTION

The present invention relates to reversible pegylation of drugs and to pegylated drugs that are slowly converted to the drugs in physiological conditions.

Abbreviations: ANP, atrial natriuretic peptide; t-Boc, tert-butyloxycarbonyl; BSA, bovine serum albumin; DCC, N,N'-dicyclohexylcarbodiimide; DCU, N,N'-dicyclohexylurea; DMF, N,N'-dimethylformamide; DTNB, 5,5-dithiobis(2-nitrobenzoic acid); ESMS, electrospray ionization mass spectra; Fmoc, 9-fluorenylmethoxycarbonyl; Fmoc-OSu, Fmoc-N-hydroxysuccinimide ester; FMS, 2-sulfo-9-fluorenyl-methoxycarbonyl; GSH, reduced glutathione; hGH, human growth hormone; HOSu, N-hydroxy-succinimide; HPLC, high-performance liquid chromatography; HSA, human serum albumin; HSA-Fmoc-insulin, a conjugate of human serum albumin and insulin; IDDM, insulin-dependent diabetes mellitus; IFN-α2, human interferon-α2; ifnar2-EC, extracellular part of IFN-α2 receptor; MAL-FMS-NHS, N-[2-(maleimido-propionyl amino)-7-sulfo-fluoren-9-yl-methoxy-carbonyloxy]succinimide (Precursor 8); MAL-FMS-OSu, MAL-FMS-NHS; MIB-NHS, maleimido benzoate N-hydroxysuccinimide ester; NHS, N-hydroxysuccinimide; PBS, phosphate-buffered saline; PEG, polyethylene glycol; $PEG_{5000}$, 5,000 Da-PEG; $PEG_{40}$ or $PEG_{40000}$, 40,000 Da-branched PEG; $PEG_{40}$-SH, a 40 kDa-branched PEG containing a sulfhydryl moiety; $PEG_{40}$-OSu, $PEG_{40}$-N-hydroxysuccinimide ester; SC, subcutaneous; STZ, streptozocin; TCA, trichloroacetic acid; TFA, trifluoroacetic acid; THF, tetrahydrofuran; TNBS, 2,4,6-trinitrobenzenesulfonic acid.

BACKGROUND OF THE INVENTION

Most peptide and protein drugs are short-lived and have often a short circulatory half-life in vivo. This is particularly valid for nonglycosylated proteins of a molecular mass less than 50 kDa. The short lifetime of proteins in vivo is attributed to several factors, including glomerular filtration in the kidney and proteolysis. Considering that peptide and protein drugs are not absorbed orally, prolonged maintenance of therapeutically active drugs in the circulation is a desirable feature of obvious clinical importance. Proteins with molecular masses above ~60 kDa largely avoid glomerular filtration and are not, for the mainpart, filtered in the kidney. Therefore they remain in the circulation longer than smaller proteins.

An attractive strategy for improving clinical properties of small protein drugs has come to be known as PEGylation (or pegylation, as used hereinafter). By this strategy several hydrophilic chains of polyethylene glycol (PEG) are covalently linked to the protein in order to increase its effective molecular mass. Important clinical advantages are gained by pegylation. For example, life-time in vivo can be prolonged in some instances from minutes to hours, owing to the steric interference that protects conjugates from proteolysis in vivo and the increase in molecular mass, which precludes filtration by the kidney. Protein pegylation also decreases immunogenicity, presumably by protecting conjugates from being recognized as foreign antigens by the immune system.

In spite of the profound advantages often gained by pegylating therapeutic proteins, this technology suffers from a principal drawback. On the one hand, covalently attaching PEG chains to proteins prolongs their lifetime in vivo, protecting the conjugates from proteolysis and shielding them from the immune system. On the other hand, the steric interference of the PEG chains often leads to a drastic loss or even abolish the biological and the pharmacological potencies of the proteins in the conjugates (Fuertges and Abuchowski, 1990; Katre, 1993; Bailon and Berthold, 1998; Nucci et al., 1991; Delgado et al., 1992; Fung et al., 1997; Reddy, 2000; Veronese, 2001). In principle, this deficiency can be overcome by introducing the PEG chains via a chemical bond that is sensitive to hydrolysis, or can be cleaved enzymatically by serum proteases or esterases. Clearly, a consistent rate of hydrolysis is crucial. A prerequisite condition is therefore that the hydrolysis of the PEG chains from the conjugate is to take place at a slow rate, and in a homogenous fashion in vivo.

It would be highly desirable to design PEG derivatives of proteins or peptides or small drug molecules from which PEG can be released by hydrolysis. An appropriate reversible PEG conjugate would have to be hydrolyzed slowly and spontaneously in physiological conditions and would permit time-dependent reactivation of inactive pegylated proteins and peptides.

Several methods for reversible pegylation were proposed (Greenwald et al., 1999, 2000; Lee et al., 2001; Garman and Kalindjian, 1987; Zalipsky et al., 1999). They suffer, however, from major potential drawbacks. For example, reliance on enzymatic detachment as a rate-determining step (Greenwald et al., 1999, 2000; Lee et al., 2001) of PEGs from conjugates by serum proteases and/or esterases might not yield desirable pharmacokinetic profiles in situ. Moreover, it is dependent on enzymes availability. Disulfide-bonded conjugate is not to be cleaved in the non-reducing environment of the body fluids (Zalipsky et al., 1999). A reversibly pegylated conjugate which still retain an active moiety capable of reacting with free SH functions may result in complex undesired cross-linking (Garman and Kalindjian, 1987). It would be very desirable to design a version of reversible pegylation that would overcome these deficiencies.

International PCT Publication No. WO 98/05361 of the present applicants describes a novel conceptual approach for prolonging the half-life of drugs by derivatizing a drug having at least one free amino, carboxyl, hydroxyl and/or mercapto groups with a moiety that is highly sensitive to bases and is removable under mild basic conditions. The prodrug obtained is inactive but undergoes transformation into the active drug under physiological conditions in the body. Examples of said moieties are the radicals 9-fluorenylmethoxycarbonyl (Fmoc) and 2-sulfo-9-fluorenylmethoxycarbonyl (FMS). According to this concept, Fmoc and FMS derivatives of peptidic drugs such as insulin and human growth hormone as well as of non-peptidic drugs such as propanolol, cephalexin and piperacillin have been described in said WO 98/05361. Later on, FMS derivatives of cytokines have been disclosed in WO 02/36067, and FMS derivatives of enkephalin, doxorubicin, amphotericin B, gentamicin and gonadotropin releasing hormone (GnRH) were disclosed in WO 02/7859.

U.S. Pat. No. 6,433,135 discloses a pegylated derivative of an analogue of luteinizing hormone releasing hormone (LHRH or GnRH) in which the PEG moiety is covalently bound to a serine residue of said LHRH analogue. In the process of preparation of said PEG-LHRH analogue by solid phase peptide synthesis, a pegylated serine residue such as Fmoc-Ser(PEG)-OH or tBoc-Ser(PEG)-OH is introduced into the LHRH analogue, and the produced PEG-LHRH analogue is recovered (without the protective group Fmoc or t-Boc).

JP Patent Application JP 3148298 describes PEG-peptide conjugates, e.g., PEG-GnRH conjugate, obtained by reacting the guanidino group of an arginine residue with PEG, while protecting the amino groups present in the molecules.

Citation of any document herein is not intended as an admission that such document is pertinent prior art, or considered material to the patentability of any claim of the present application. Any statement as to content or a date of any document is based on the information available to applicants at the time of filing and does not constitute an admission as to the correctness of such a statement.

SUMMARY OF THE INVENTION

It has been found, in accordance with the present invention, that drugs with a prolonged circulating half-life can be obtained by combining the technology of derivatization of the drug with Fmoc or FMS or similar moieties removable under mild basic conditions with the technology of attaching a suitable natural or synthetic carrier to the thus derivatized drug molecule, such carrier serving for delivery of the drug and providing further benefits.

The carrier may be a protein such as albumin or a protein containing a globin-like domain or a polymeric carrier consisting of a biocompatible and biodegradable polymer containing functional groups. The polymeric carrier is preferably in the form of nanoparticles or it is attached to liposomes.

In one preferred embodiment, the polymeric carrier is PEG. It has been found, in accordance with the present invention, that by combination of the protein-pegylation technology with the technology of derivatization with Fmoc or FMS or similar moieties removable under mild basic conditions, major deficiencies of the protein-pegylation technology, mainly the loss of biological and pharmacological potencies in the PEG conjugates in vivo, may be overcome.

In one embodiment of the present invention, PEG-protein conjugates are provided from which PEG can be released by hydrolysis under physiological conditions in the body.

In another embodiment, reversible PEG-protein conjugates are provided that are inactive when administered and permit time-dependent reactivation of the inactivated pegylated protein under physiological conditions in the body.

The present invention thus relates, in one aspect, to a compound of the formula:

(X)$_n$—Y wherein

Y is a moiety of a drug bearing at least one functional group selected from free amino, carboxyl, phosphate, hydroxyl and/or mercapto, and X is a radical that is highly sensitive to bases and is removable under mild basic conditions, said radical carrying a protein or a polymeric carrier moiety, n is an integer of at least one, and pharmaceutically acceptable salts thereof.

The prodrug obtained is inactive but undergoes transformation into the active drug Y under physiological conditions in the body.

In preferred embodiments of the invention, the radical X is Fmoc or 2-sulfo-Fmoc (herein "FMS"), Y is a peptide or protein drug linked to Y through an amino group, n is 1 or 2, the protein carrier is albumin and the polymeric carrier is a linear or branched PEG moiety having a molecular weight of 5,000-40,000 Da.

In another aspect, the present invention provides novel methods and intermediates and precursors for the preparation of the conjugates of the invention.

In a further aspect, the present invention provides pharmaceutical compositions comprising a pharmaceutically acceptable carrier and a prodrug of the invention.

PEG$_{5000}$-Fmoc-insulin conjugates containing one and two moles of PEG$_{5000}$-Fmoc/mole insulin were incubated at a concentration of 0.172 μM in 0.1 M NaHCO$_3$-0.5% bovine serum albumin and 1 mM NaN$_3$ at 37° C. At the indicated time points aliquots were analyzed (in several concentrations for each aliquot) for their lipogenic potencies in rat adipocytes.

Figure 6:
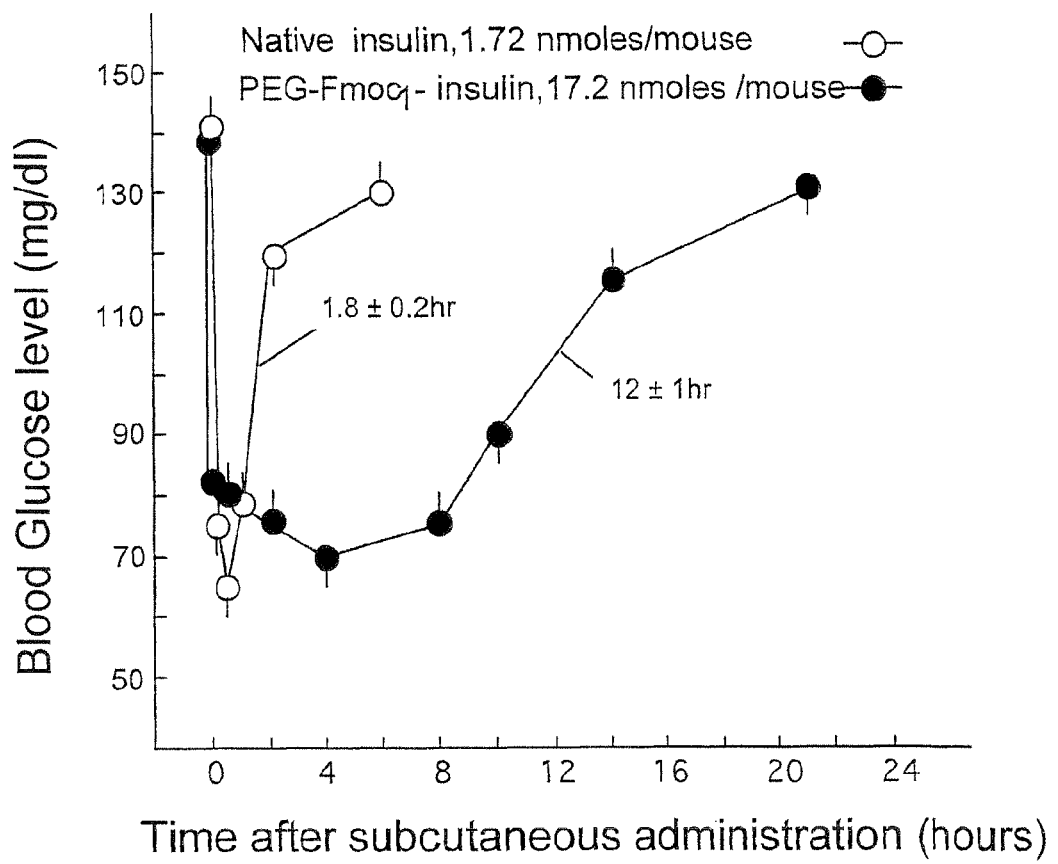

FIG. 6 shows prolonged glucose-lowering effect after a single subcutaneous (SC) administration of (PEG$_{5000}$-Fmoc)$_1$-insulin in mice. Mice received SC, either native insulin (Zn$^{2+}$-free, 1.72 nmole/mouse in 0.2 ml PBS buffer) or (PEG$_{5000}$-Fmoc)$_1$-insulin (17.2 nmole/mouse, in 0.2 ml PBS buffer). Blood glucose levels were determined at the indicated time points. Each point is the arithmetic mean±SEM of blood glucose of five mice.

Figure 7:
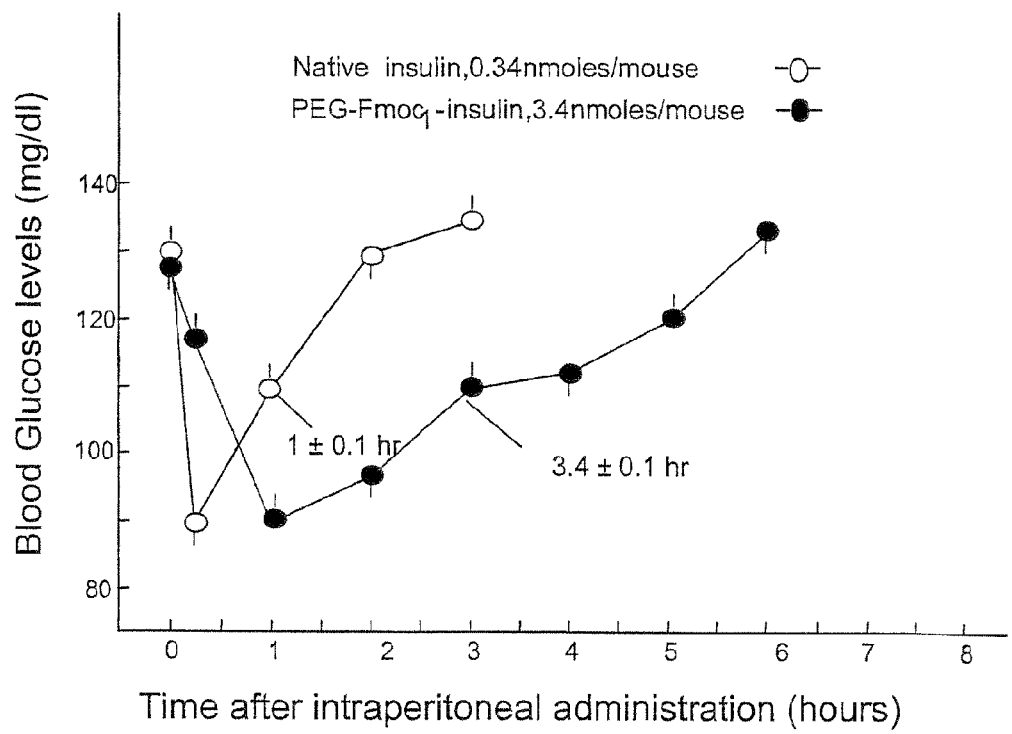

FIG. 7 shows glucose-lowering pattern in mice following single intraperitoneal (IP) administration of (PEG$_{5000}$-Fmoc)$_1$-insulin. Groups of mice received IP either insulin (Zn$^{2+}$-free, 0.345 nmol/mouse, in 0.2 ml PBS buffer) or (PEG$_{5000}$-Fmoc)$_1$-insulin (3.45 nmoles/mouse, in 0.2 ml PBS buffer). Blood glucose levels were determined at the indicated time points. Each point in the figure is the arithmetic mean±SEM of five mice.

Figure 8:
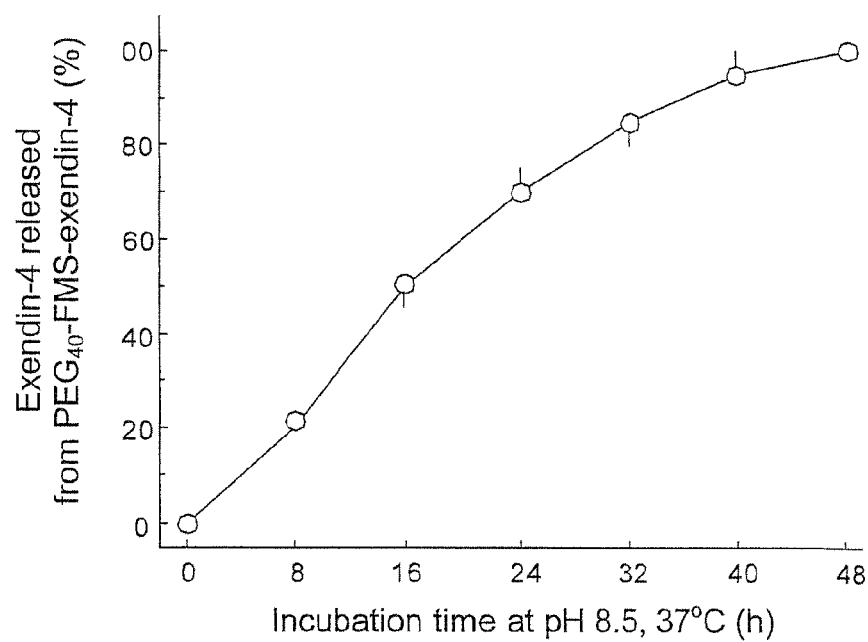

FIG. 8 shows the rate of release of exendin-4 from PEG$_{40}$-FMS-exendin-4 conjugate, upon incubation at pH 8.5, 37° C. At the indicated time points, aliquots (50 μl) were loaded on HPLC, and ran under conditions resolving well exendin-4 from the conjugate. Results are expressed as percent of maximal peak area of released exendin-4, as a function of time. Exendin-4 (50 μg) was assigned at 100% peak area.

Figure 9:
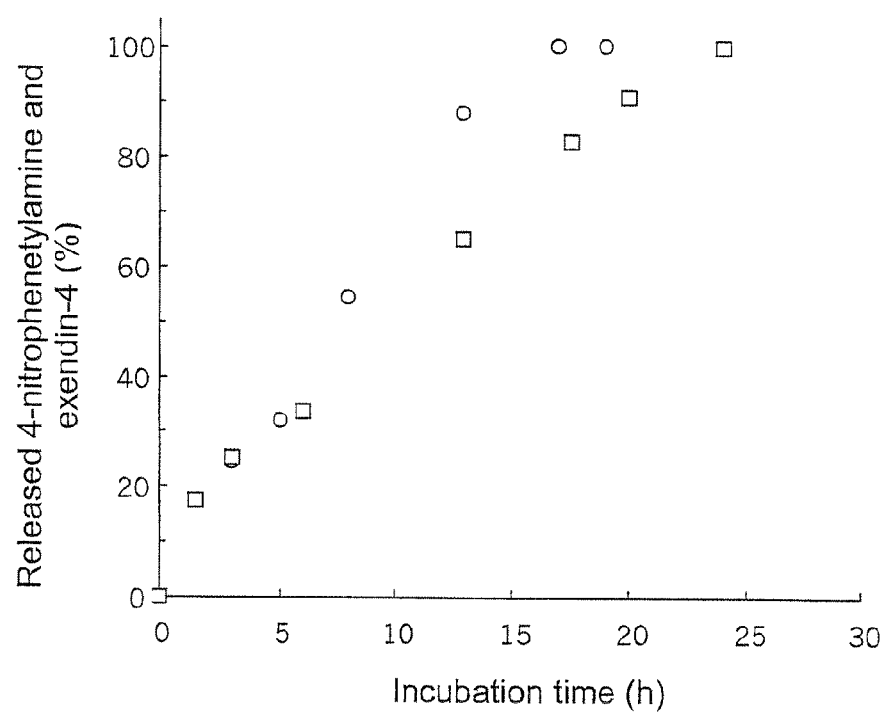

FIG. 9 shows the rate of hydrolysis of PEG-FMS conjugates, upon incubation at pH 8.5, 37° C. Solutions of PEG$_{5000}$-FMS-exendin-4 (circles) and PEG$_{5000}$-FMS-4-nitro-phenethyl amine (squares) were incubated in PBS at pH 8.5, 37° C. At the indicated time points, aliquots (50 μl) were analyzed using HPLC on a RP-4 column. Results are expressed as percent of the maximal peak area of released exendin-4 and 4-nitrophenethylamine, as a function of time.

Figure 10A:
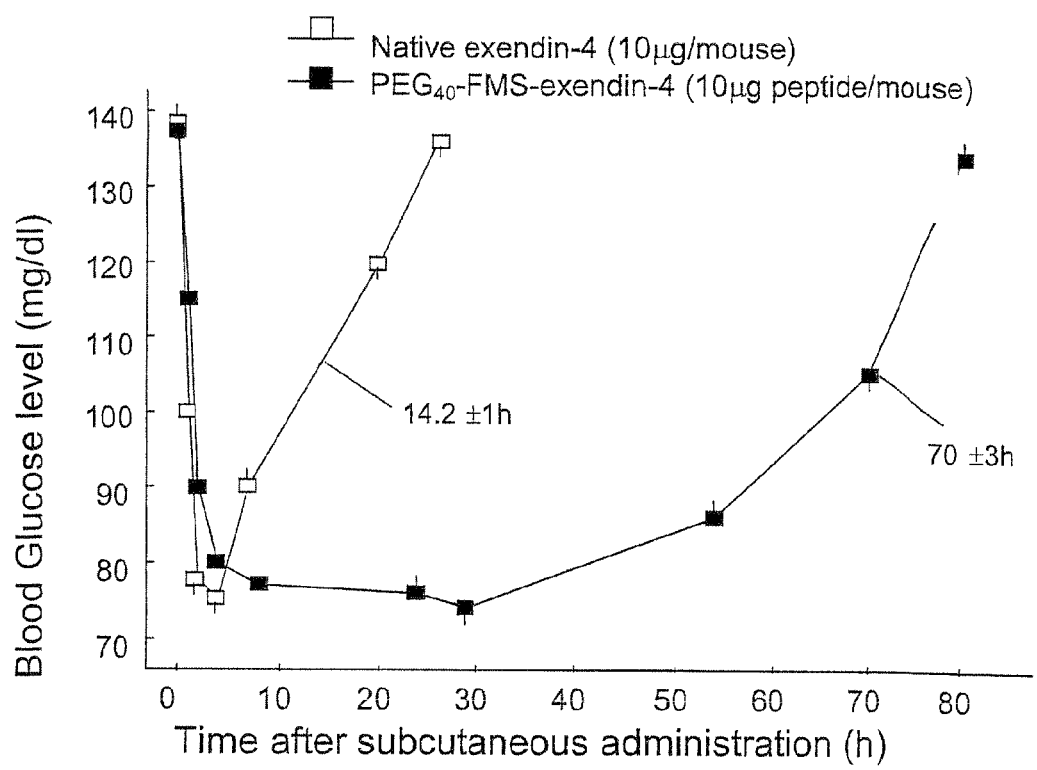
Figure 10B:
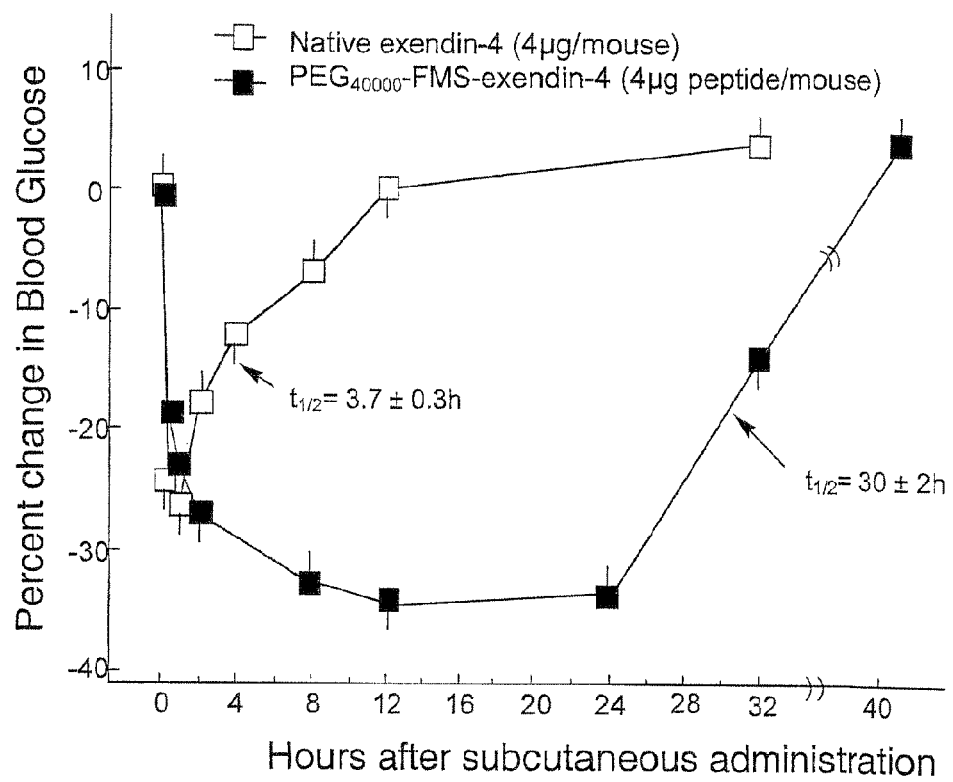

FIGS. 10A-10B show glucose-lowering patterns of native exendin-4 and PEG$_{40000}$-FMS-exendin-4 following a single subcutaneous administration to CD1-mice. (10A) CD1-mice were SC-administered with either native exendin-4 (10 μg/mouse) or with PEG$_{40}$-FMS-exendin-4 (10 μg/mouse of exendin-4 equiv). At the indicated time points, circulating glucose levels were determined. Each experimental group consisted of five mice. Data are presented as means±SE. (10B) Three groups of CD1 mice (n=6 per group) underwent one subcutaneous administration of saline, native exendin-4 (4 μg/mouse) or PEG$_{40000}$-FMS-exendin-4 (4 μg peptide/mouse). Circulating glucose levels were then monitored. Results are expressed as percent decrease in plasma glucose concentration in the groups treated with exendin-4 or PEG$_{40000}$-FMS-exendin-4 relative to that found in the saline-treated group measured at the same time-point during the day.

Figure 11A:
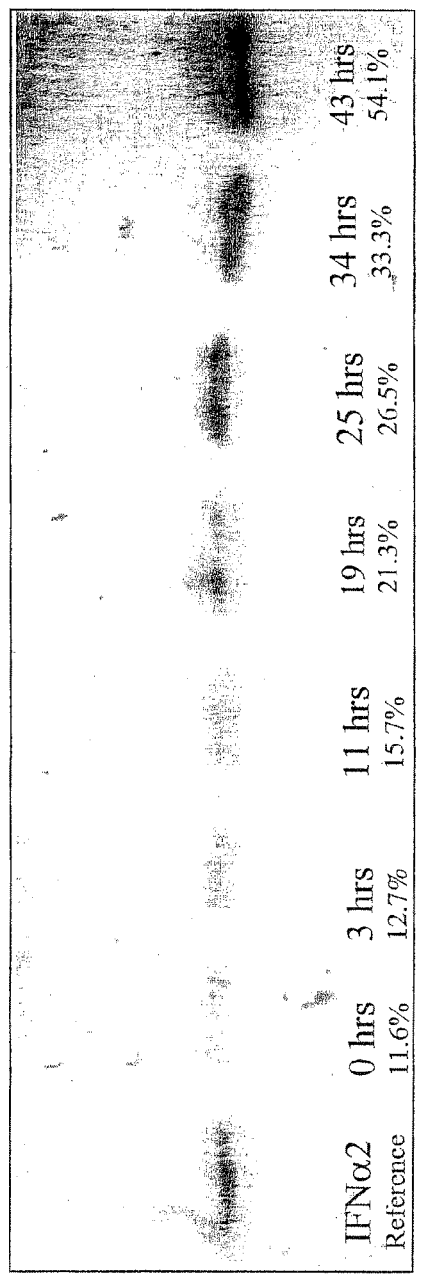
Figure 11B:
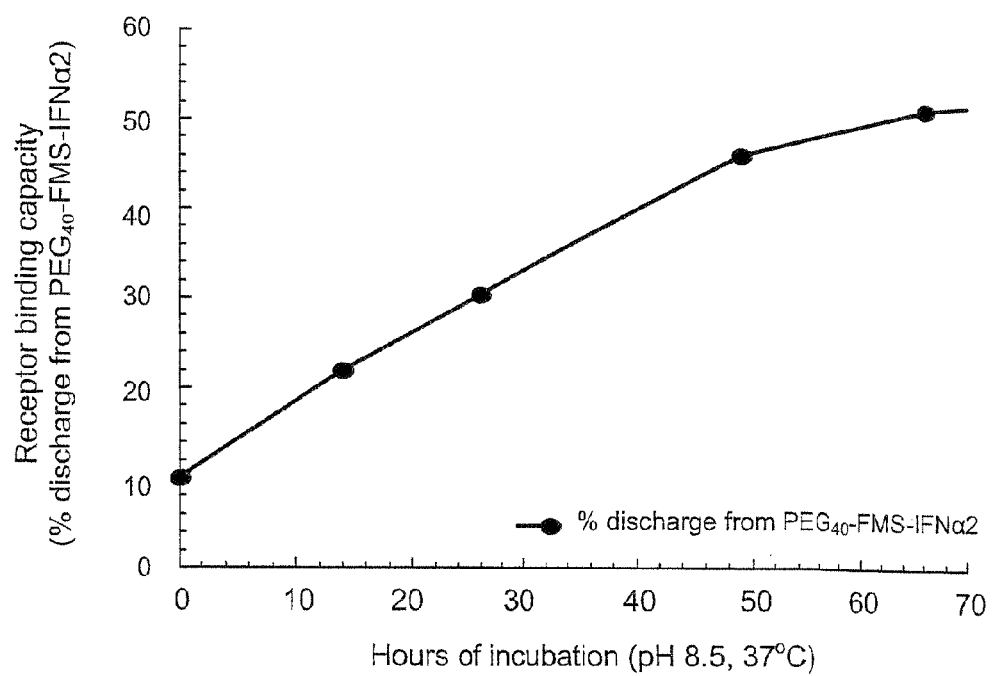
Figure 11C:
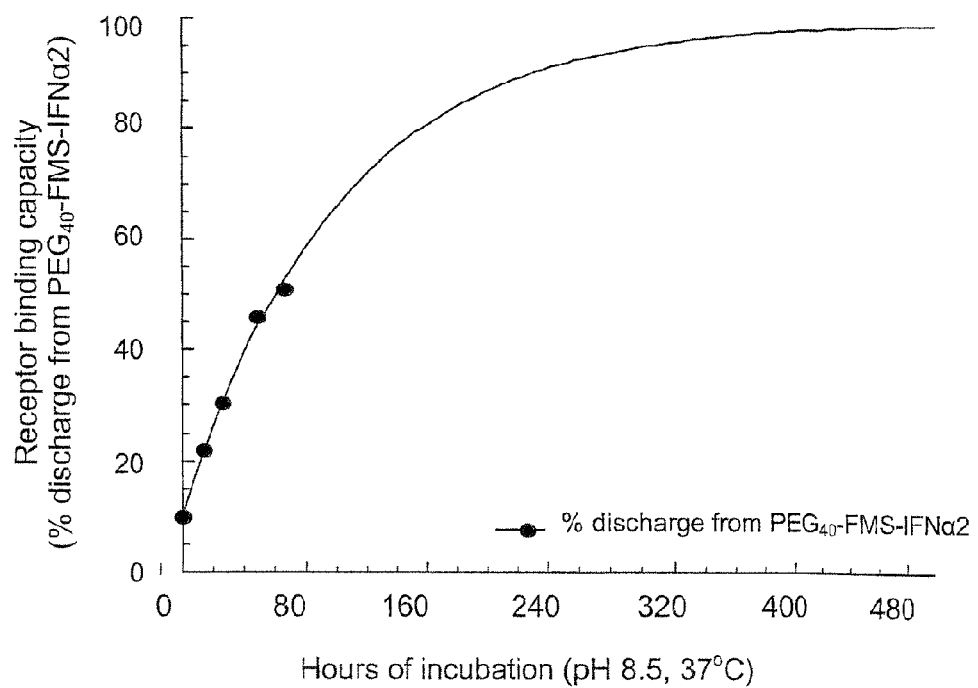

FIGS. 11A-11C show release of active IFNα2 upon incubation of PEG$_{40}$-FMS-IFNα2 at pH 8.5, 37° C. PEG$_{40}$-FMS-IFNα2 (0.3 mg protein/ml) was incubated in 0.1 M phosphate buffer with 2 mM NaN$_3$ and 6 mg/ml BSA (pH 8.5, 37° C.). At the indicated time points, aliquots were withdrawn. (11A) Analysis of IFNα2 discharge from the conjugate by SDS-PAGE; the amounts of IFNα2 discharge were quantified relative to an IFNα2 reference of known concentration and intensity (the time increments and the percentages are indicated); (11B) Aliquots withdrawn at the indicated time points were analyzed for their Ifnar2 binding capacity on BIAcore; (11C) Fitted BIAcore profile of native IFNα2 discharge from PEG$_{40}$-FMS-IFNα2.

Figure 12:
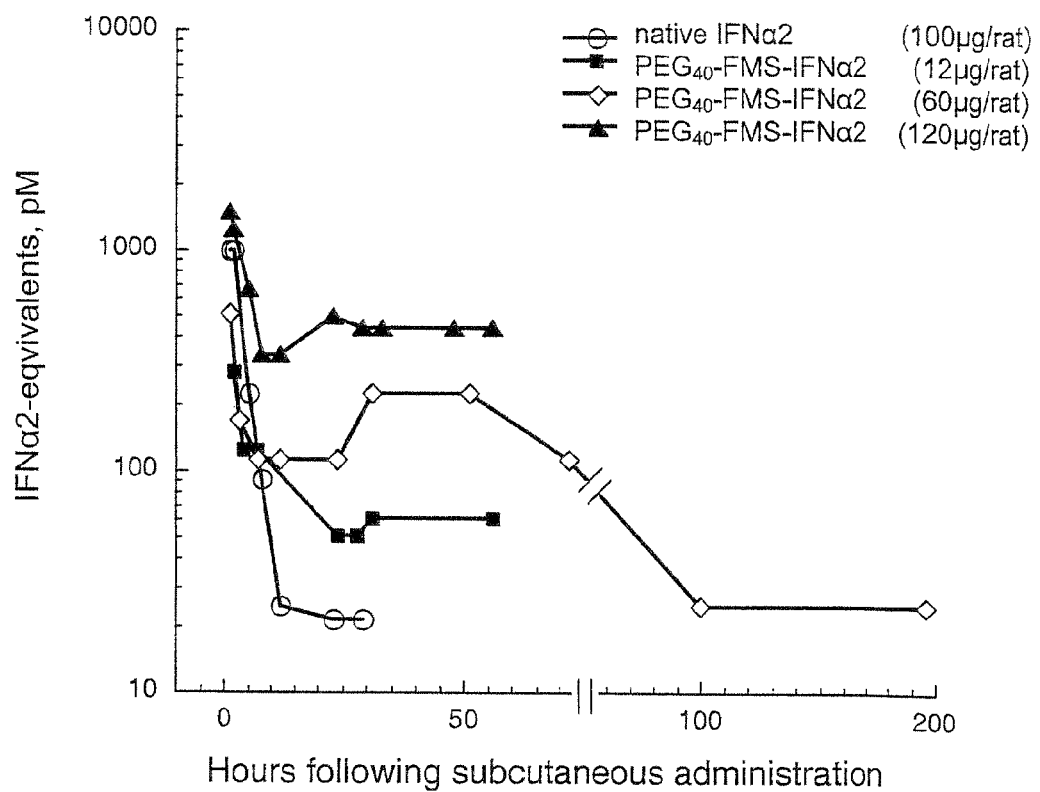

FIG. 12 shows the results of SC administration of native IFNα2 and PEG$_{40}$-FMS-IFNα2. Rats were SC injected with the indicated concentrations of native IFNα2 (100 μg/rat) or the PEG$_{40}$-FMS-IFNα2 conjugate (12, 60, 120 μg/rat) (0.2 ml/rat, dissolved in PBS). Blood aliquots were withdrawn at the indicated time points. Circulating antiviral activities in the aliquots were determined in human WISH cells with 3-fold serial dilutions of each aliquot.

Figure 13:
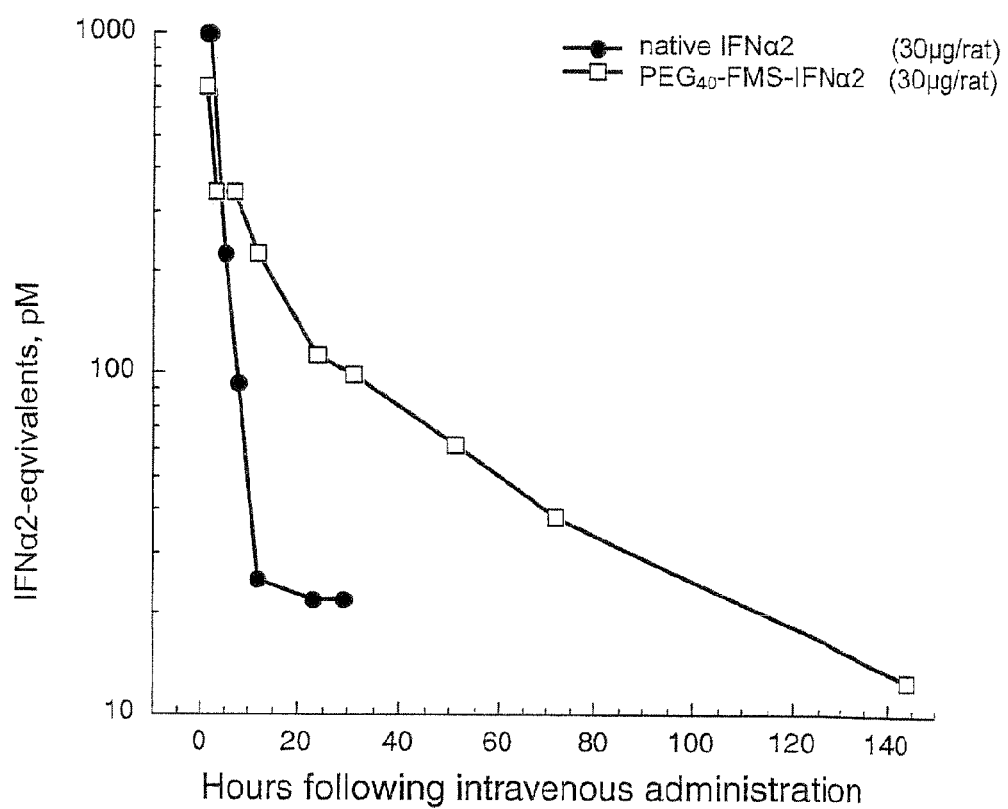

FIG. 13 shows the result of intravenous administration of PEG$_{40}$-FMS-IFNα2 to rats. Rats were intravenously injected with the indicated concentrations of native IFNα2 (30 μg/rat) or the PEG$_{40}$-FMS-IFNα2 conjugate (30 μg/rat) (0.2 ml/rat, dissolved in PBS). Blood aliquots were withdrawn at the indicated time points. Circulating antiviral activities in the aliquots were determined in human WISH cells with 3-fold serial dilutions of each aliquot.

Figure 14A:
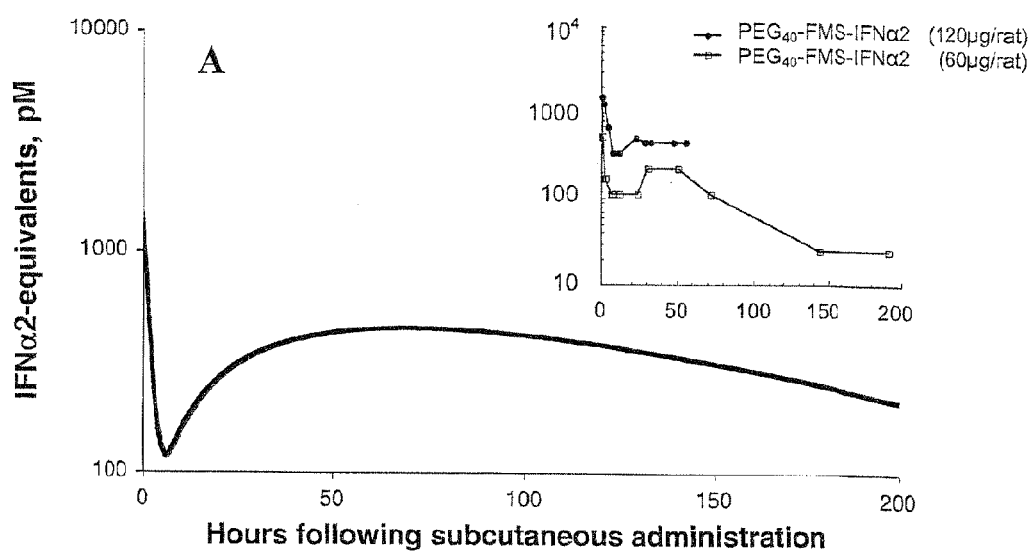
Figure 14B:
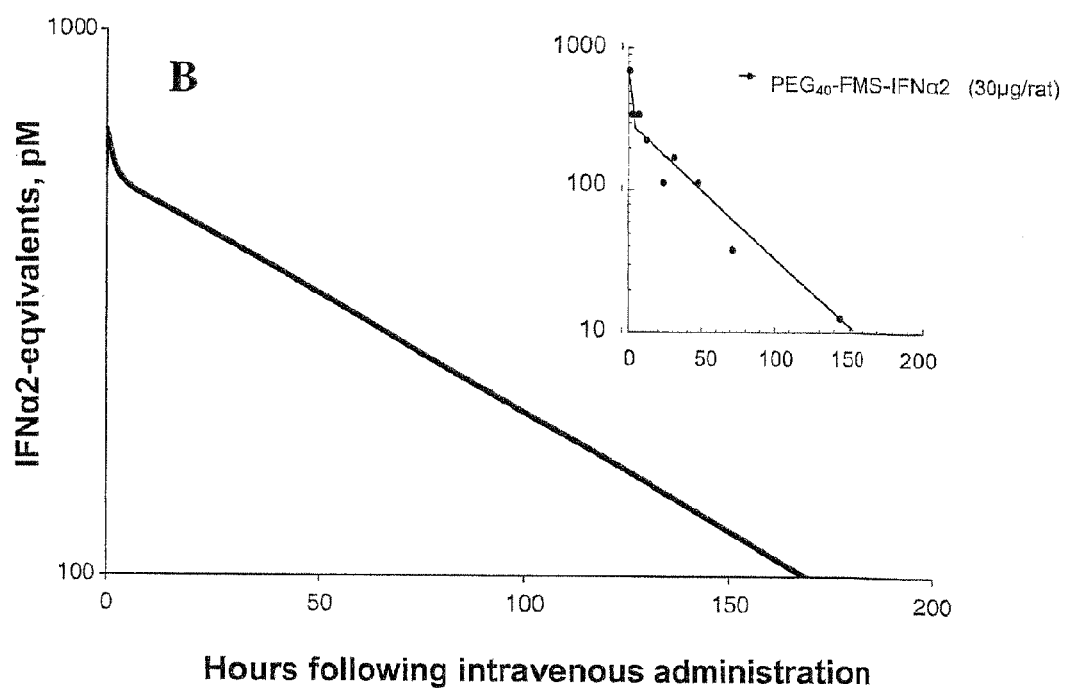

FIGS. 14A-14B show experimental vs. simulated behavior of IFNα2: (14A) following SC administration, with initial concentrations of 60 nM and 1.5 nM of PEG$_{40}$-FMS-IFNα2 and native IFNα2, respectively; (14B) following intravenous administration to rats with initial concentrations of 20 nM of PEG$_{40}$-FMS-IFNα2, 1.5 nM of native IFNα2 in the SC volume and no conjugate in circulation. The inserts are the experimental curves.

Figure 15:
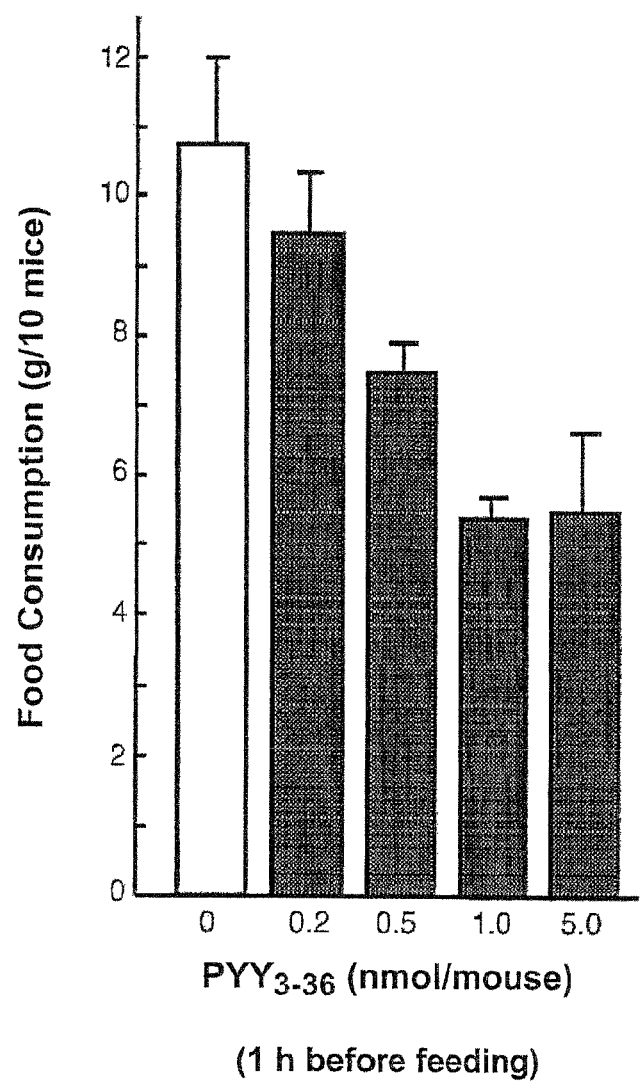

FIG. 15 shows dose-response of PYY$_{3-36}$ in food intake in mice. Male C57BL6J mice (10 per group), were deprived of food for 24 h. At time 23 h, the mice received a SC injection of either saline or the indicated doses of PYY$_{3-36}$. At time 24 h the mice were allowed to consume an excess of pre-weighted chow for 2 h. Drinking water was provided at all times. The amount of food consumed per 10 mice during 2 h is shown as a function of PYY$_{3-36}$ dose.

Figure 16:
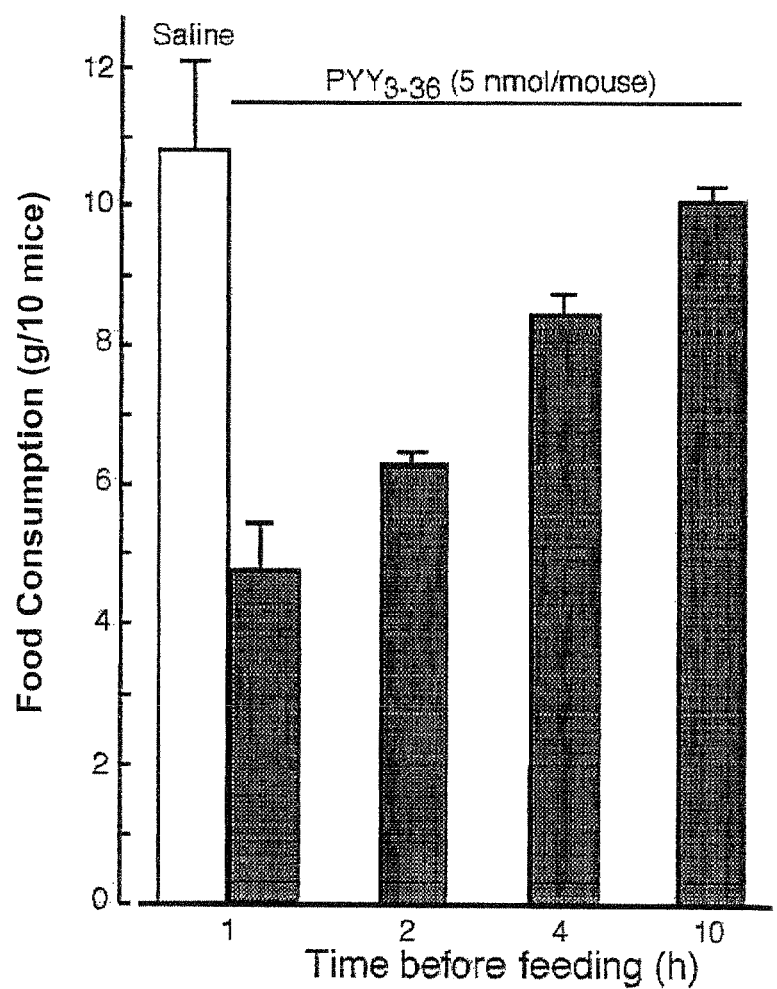

FIG. 16 shows time-dependent reduction in food intake in mice by PYY$_{3-36}$. Male C57BL6J mice (10 per group) were deprived of food as described in FIG. 15 and PYY$_{3-36}$ (5 nmol/mouse) was administered at the indicated times prior to start of the re-feeding period. Results are average of four identical experiments.

Figure 17:
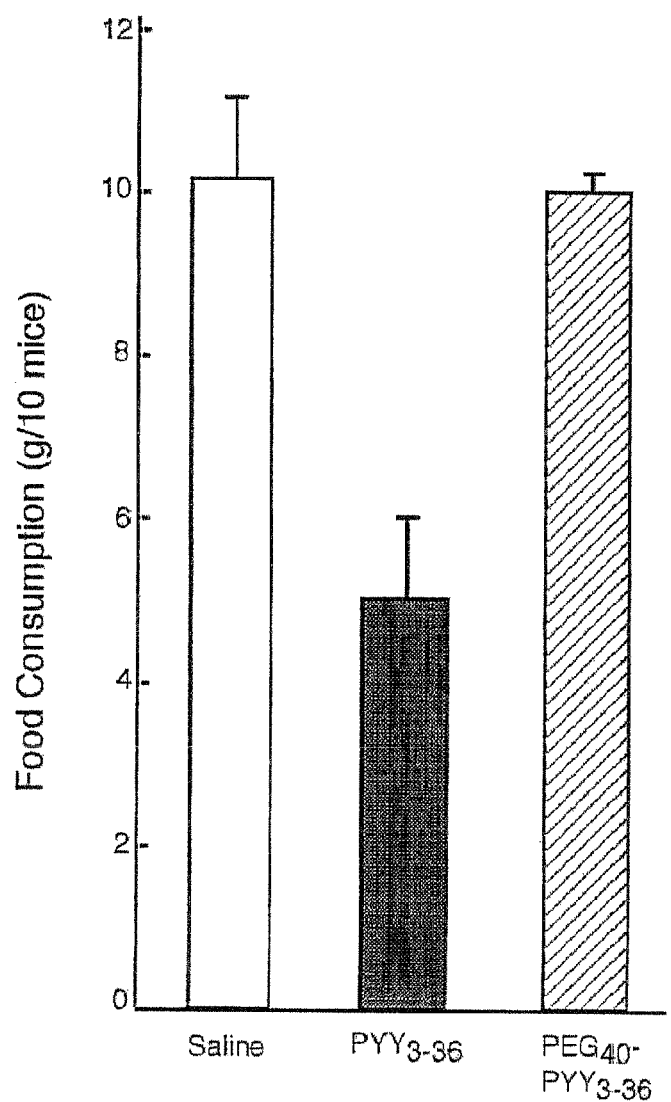

FIG. 17 shows the effects of irreversible pegylation on the biological activity of PYY$_{3-36}$. Native PYY$_{3-36}$ was allowed to react with PEG$_{40}$-OSu. Groups of 10 mice were injected SC with saline, PYY$_{3-36}$, or PEG$_{40}$-PYY$_{3-36}$ (5 nmol/mouse) at 1 h prior to start of the re-feeding period. Results are the average of two identical experiments.

Figure 18:
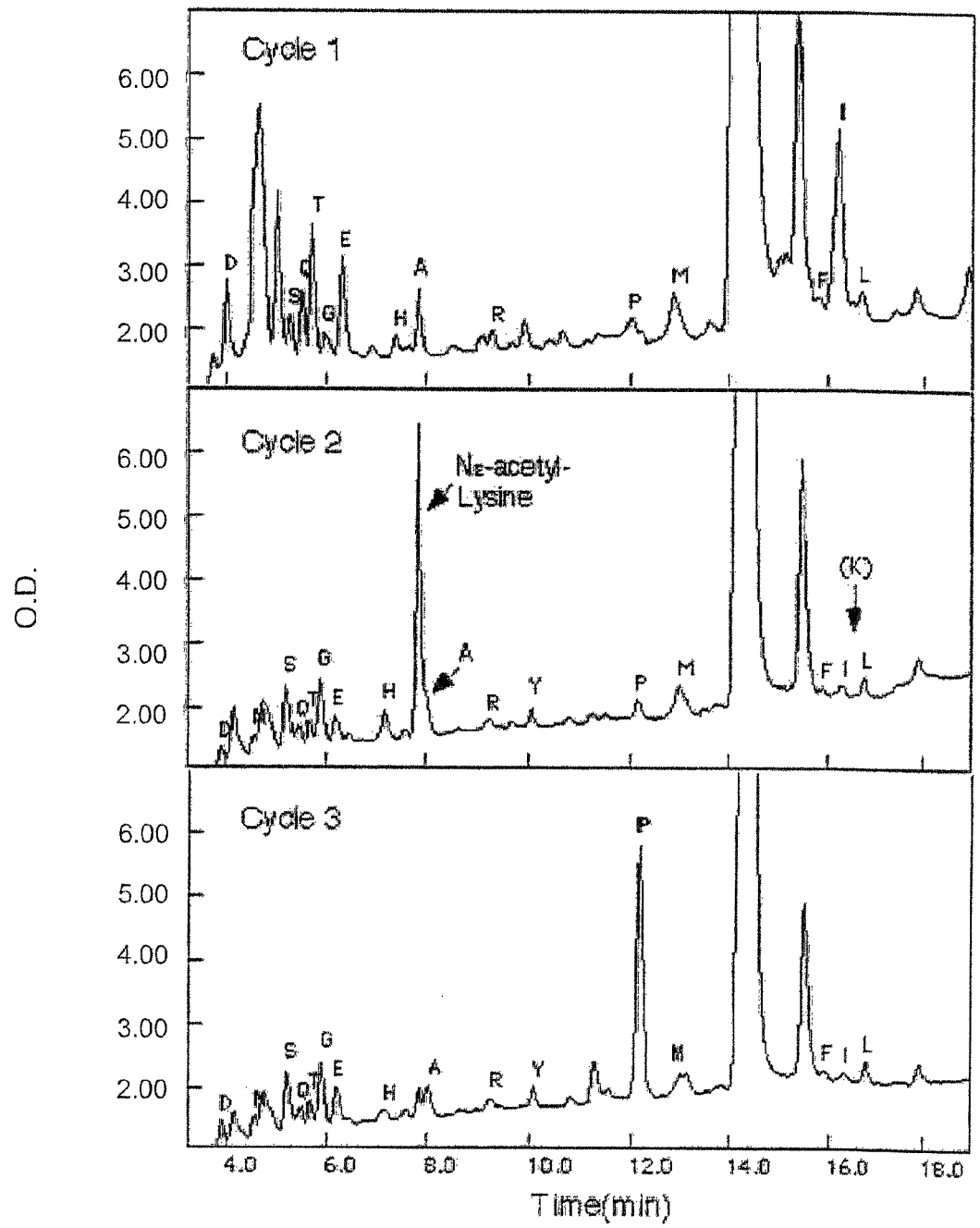

FIG. 18 shows that PEG$_{40}$-FMS is linked to the α-amino group of PYY$_{3-36}$. PEG$_{40}$-FMS-PYY$_{3-36}$ (100 μg) was acetylated by a 500 molar excess of acetic anhydride at pH 7.0, dialyzed, and incubated for 3 days at pH 8.5, 37° C. to quantitatively remove the PEG$_{40}$-FMS moiety. The resulting acetylated PYY$_{3-36}$ was then subjected to three cycles of N-terminal protein sequence analysis. The sequence obtained was Ile-(Nε-acetyl)Lys-Pro. Sequence analysis of the native peptide yielded Ile, Lys, and Pro on cycles 1, 2, 3, respectively (not shown).

Figure 19:
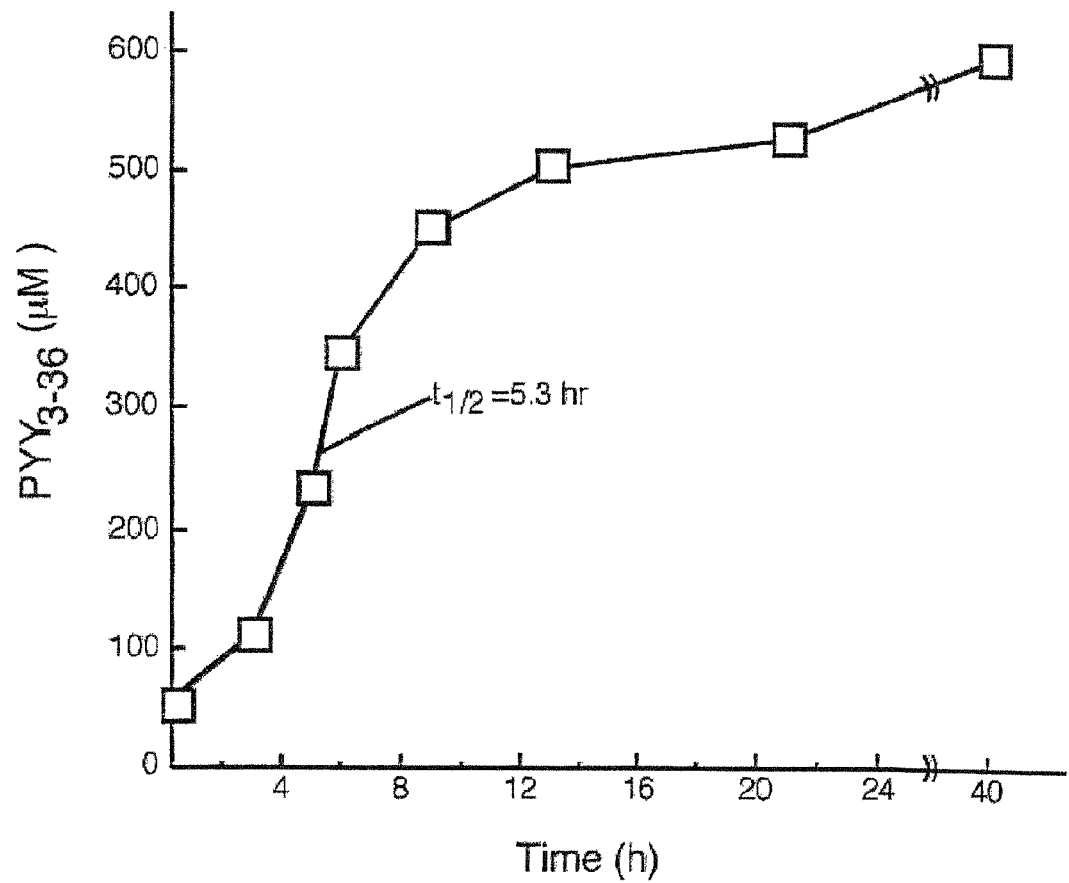

FIG. 19 shows the kinetics of PYY$_{3-36}$ release from PEG$_{40}$-FMS-PYY$_{3-36}$. PEG$_{40}$-FMS-PYY$_{3-36}$ (750 μM in 0.1 M phosphate buffer pH 8.5, 2 mM NaN$_3$), was incubated at 37° C. Aliquots (100 μl) were withdrawn at the indicated times and free PYY$_{3-36}$ was measured by HPLC. The cumulative amount of PYY$_{3-36}$ released is shown as a function of time. The amount of PYY$_{-36}$ in the initial conjugate was determined by acid hydrolysis of a 20 μl aliquot, followed by amino acid analysis.

Figure 20:
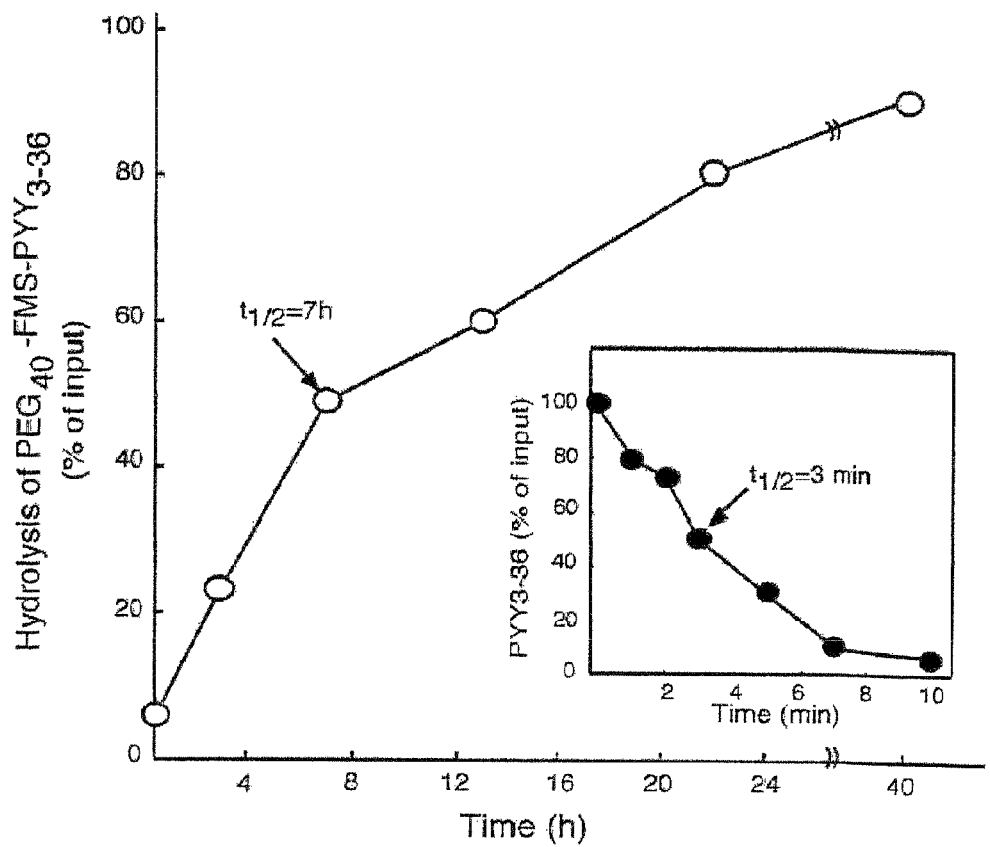

FIG. 20 shows the rate of PEG$_{40}$-FMS-PYY$_{3-36}$ hydrolysis in normal mouse serum. PEG$_{40}$-FMS-PYY$_{3-36}$ (0.5 μM) in normal mouse serum was incubated at 37° C. Aliquots were withdrawn at the indicated times and the amount of 2-PEG$_{40}$-

9-sulfo-fulvene released from $PEG_{40}$-FMS-$PYY_{3-36}$ was determined by HPLC and taken for calculating the rate of $PEG_{40}$-FMS-$PYY_{3-36}$ hydrolysis. The insert shows that $PYY_{3-36}$ degrades rapidly in normal mouse serum at 37° C. $PYY_{3-36}$ (50 nM) in normal mouse serum was incubated at 37° C. At the indicated times, aliquots (0.1 ml) were removed, de-proteinated by 3 volumes of ethanol and the quantity of $PYY_{3-36}$ was determined in the supernatants by HPLC.

Figure 21:
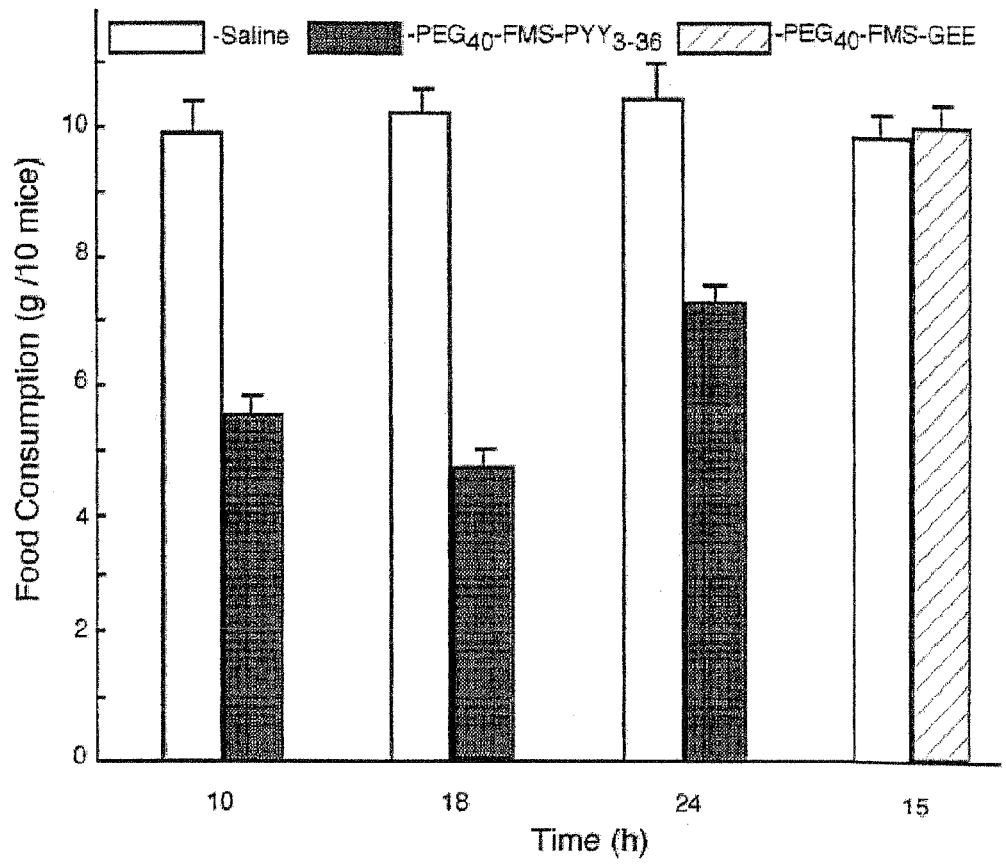

FIG. 21 shows that $PEG_{40}$-FMS-$PYY_{3-36}$ elicits prolonged satiety. The protocol described in FIG. 15 was repeated, except that the mice received SC either saline or $PEG_{40}$-FMS-$PYY_{3-36}$ (5 nmol/mouse) at the indicated times prior to re-feeding. Results are average of three identical experiments, normalized according to the saline control.

Figure 22:
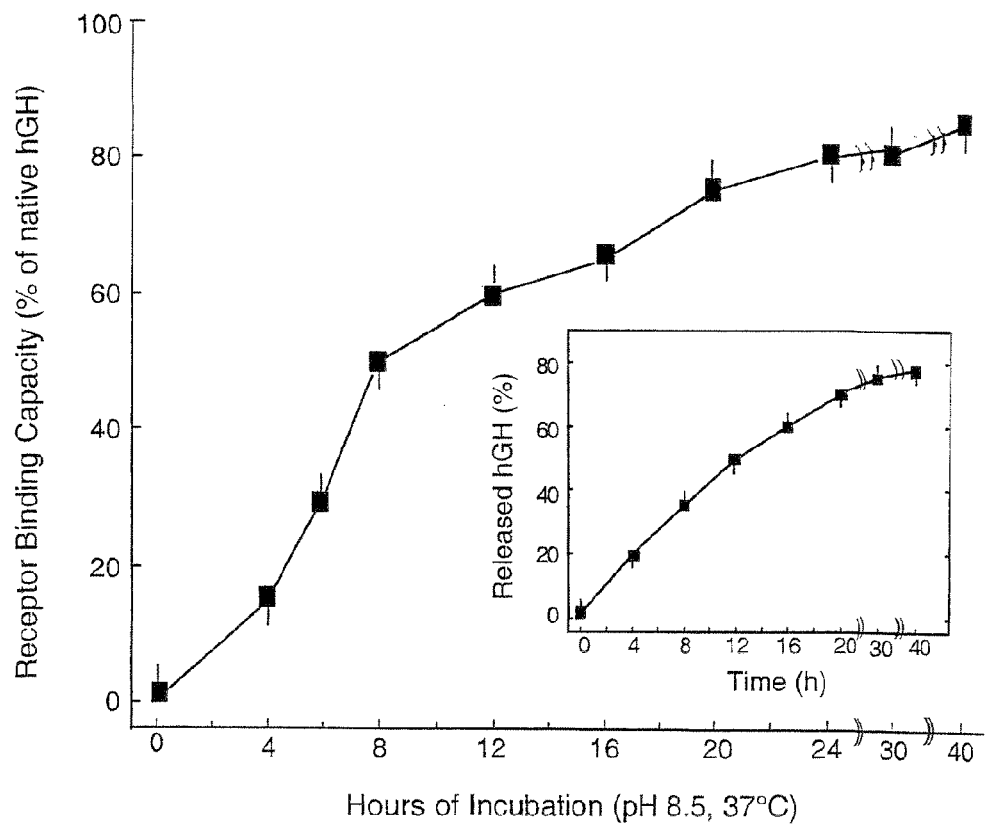

FIG. 22 shows the time course of reactivation of $PEG_{40000}$-FMS-hGH upon incubation at pH 8.5, 37° C. $PEG_{40000}$-FMS-hGH (1 mg/ml) was incubated in 0.1 M phosphate buffer, 0.6% BSA and ~2 mM $NaN_3$ at 37° C. Aliquots were withdrawn at the indicated time points, and analyzed for their potencies to displace $^{125}$I-hGH from enriched hGH-receptor preparation extracted from rabbit liver plasma membranes. Native hGH displaces $^{125}$I-hGH in this assay half maximally at a concentration of 0.3±0.03 nM. An hGH derivative exhibiting half maximal displacement in this assay at a concentration of 3.0±0.3 nM is considered to have 10% of the native receptor's binding potency. The insert shows the rate of release of hGH from $PEG_{40}$-FMS-hGH upon incubation at pH 8.5, 37° C. $PEG_{40000}$FMS-hGH (1 mg protein) was incubated as described above. At the indicated time points, 0.1 ml aliquots withdrawn and subjected to analytical HPLC analysis.

Figure 23:
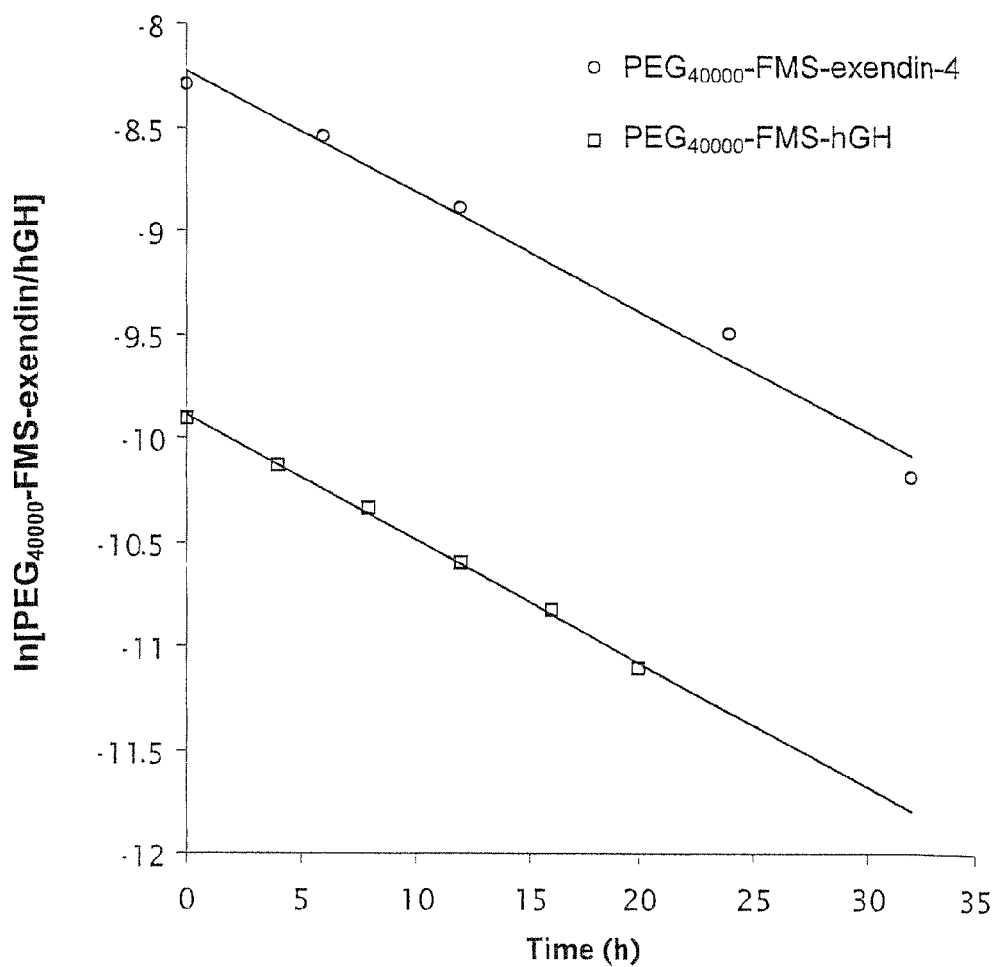

FIG. 23 shows the rate of hydrolysis of PEG-FMS conjugates, upon incubation at pH 8.5, 37° C. The concentration of $PEG_{40000}$-FMS-exendin-4 and $PEG_{40000}$-FMS-hGH was determined for each time point by HPLC. The linear plot obtained indicates that the rate of hydrolysis is of first order reaction. The half-life time of the conjugates was calculated from $t_{1/2}=\ln2/k$, when k is the slope of the linear plot ($h^{-1}$).

Figure 24:
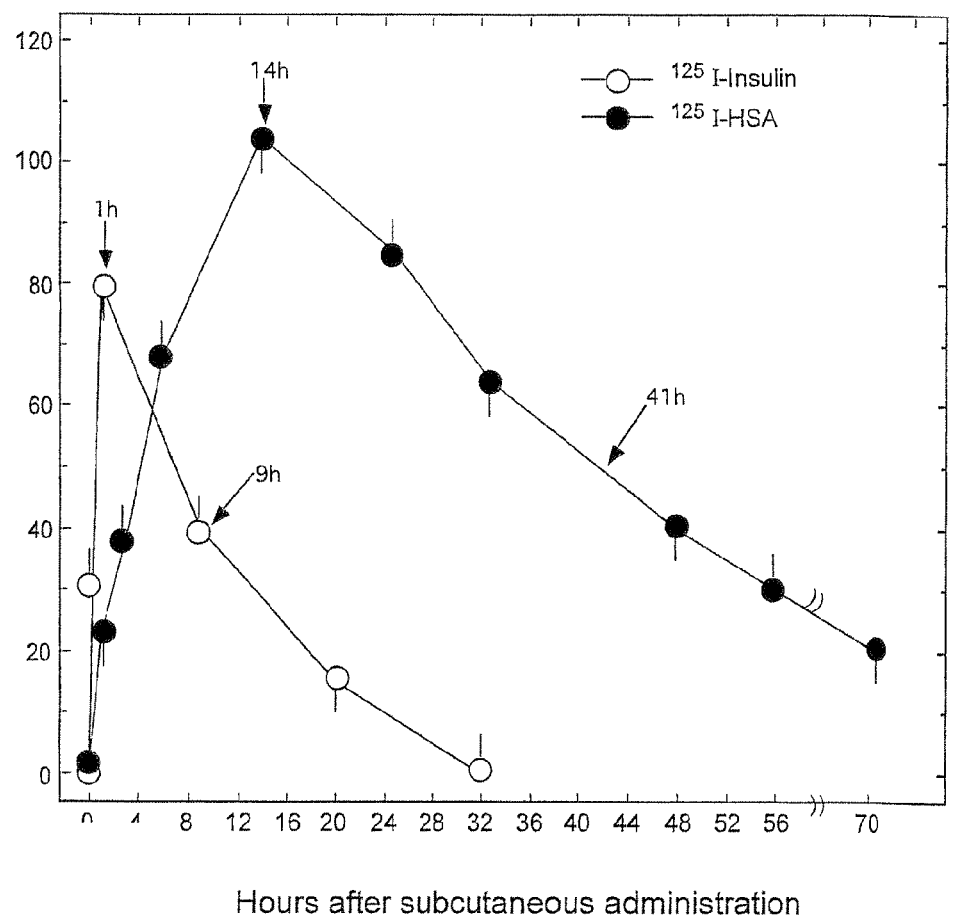

FIG. 24 shows the pharmacokinetic profiles of subcutaneously administered radiolabeled insulin and human serum albumin in rats. At t=0, groups of Wistar rats (170±5 g each, n=5 per group) were injected subcutaneously with 0.3 ml PBS (pH 7.4) and 0.5% BSA containing either 10 μg 125I-insulin (specific activity 2800 cpm/ng) or 10 μg HSA (specific activity 1400 cpm/ng). Blood aliquots obtained from the tail vein at the indicated time points were spotted onto Whatman #3 paper and weighed immediately. Each paper was washed with 10% TCA and measured for its radioactive content. Results are expressed as ng of TCA precipitable protein (insulin or HSA) per ml blood. Each point in the figure represents the arithmetic mean of 5 rats±SE. Arrows indicate the times at which peak values were attained and the species $t_{1/2}$ values.

Figure 25A:
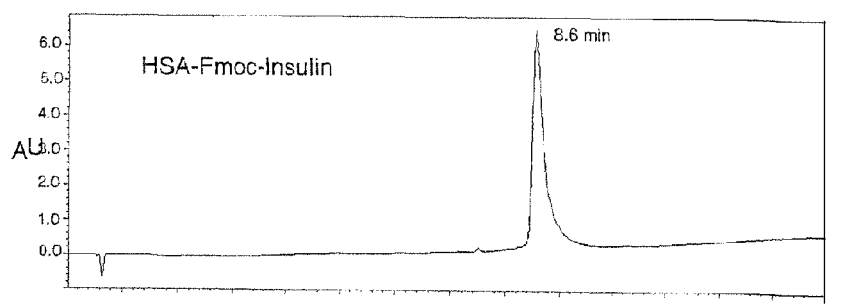
Figure 25B:
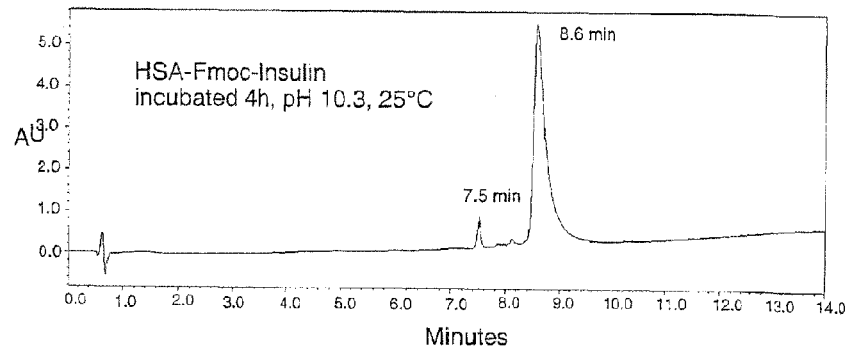

FIGS. 25A-25B show the HPLC analysis of purified HSA-Fmoc-insulin before and after the release of insulin by hydrolysis. HPLC was conducted with a linear gradient from 0 to 100% of solution A (0.1% TFA) to solution B (acetinitrile-$H_2O$, 75:25 in 0.1% TFA) over 10 minutes and then 4 minutes in solution B, using a Chromolith RP 18e (100×4 mm) column at a rate of 3 ml/minutes. The effluent was monitored at 220 nm. (25A) Purified HSA-Fmoc-insulin (100 μg loaded); (25B) Purified HSA-Fmoc-insulin following 4 hrs hydrolysis through incubation at pH 10.3, 25° C. Under the same experimental conditions, insulin elutes with Rt=6.91 min and has a surface area of 187,000±9,000 mav/μg insulin.

FIG. 26 shows the dosage-dependent stimulation of lipogenesis in rat adipocytes. Lipogenesis was carried out for 2 h at 37° C. in plastic vials containing 0.5 ml of fat cell suspension (1.5×105 cells) and 0.2 mM [U—$^{14}$C] glucose in the presence or absence of the indicated concentrations of native insulin or HSA-insulin conjugates. Results are expressed as a percentage of maximal stimulation. Insulin (100 ng/ml) stimulated lipogenesis four to five-fold above basal levels. HSA-Fmoc-insulin (1 mg/ml) was taken as containing 24±3 μg insulin per mg HSA in this assay (see Table 6). The $ED_{50}$ values for native insulin (0.3 ng/ml) for HSA-Fmoc-insulin (2.4 ng/ml) and for HSA-Benz-insulin (130 ng/ml) are indicated with arrows on the figure.

FIGS. 27A-27B show the rate of insulin release from HSA-Fmoc-insulin and reactivation of the conjugate upon incubation at pH 8.5, 37° C. A solution of HSA-Fmoc-insulin (1 mg/ml) was incubated in 0.1 M phosphate buffer at pH 8.5, 37° C. At the indicated time points, aliquots (100 μl) were analyzed by HPLC for the amount of released insulin (27A) and for biological potency in rat adipocytes (27B). Results are expressed as the amount of insulin released per mg HSA-Fmoc-insulin. An aliquot of HSA-Fmoc-insulin exhibiting $ED_{50}$ value=3.0 ng/ml in a lipogenic assay was considered to have 10% the native biological potency.

FIGS. 28A-28B show the circulating glucose levels in mice following a single subcutaneous or intraperitoneal administration of HSA-Fmoc-insulin. Mice were injected intraperitoneally (28A) or subcutaneously (28B) with Zn2+ free insulin (3 μg/mouse in 0.2 ml saline) or HSA-Fmoc-insulin (0.4 mg/mouse). Blood glucose levels were determined at the indicated time points. Food was removed during the experiment. Each point is the arithmetic mean of n=5 mice±SE.

Figure 29:
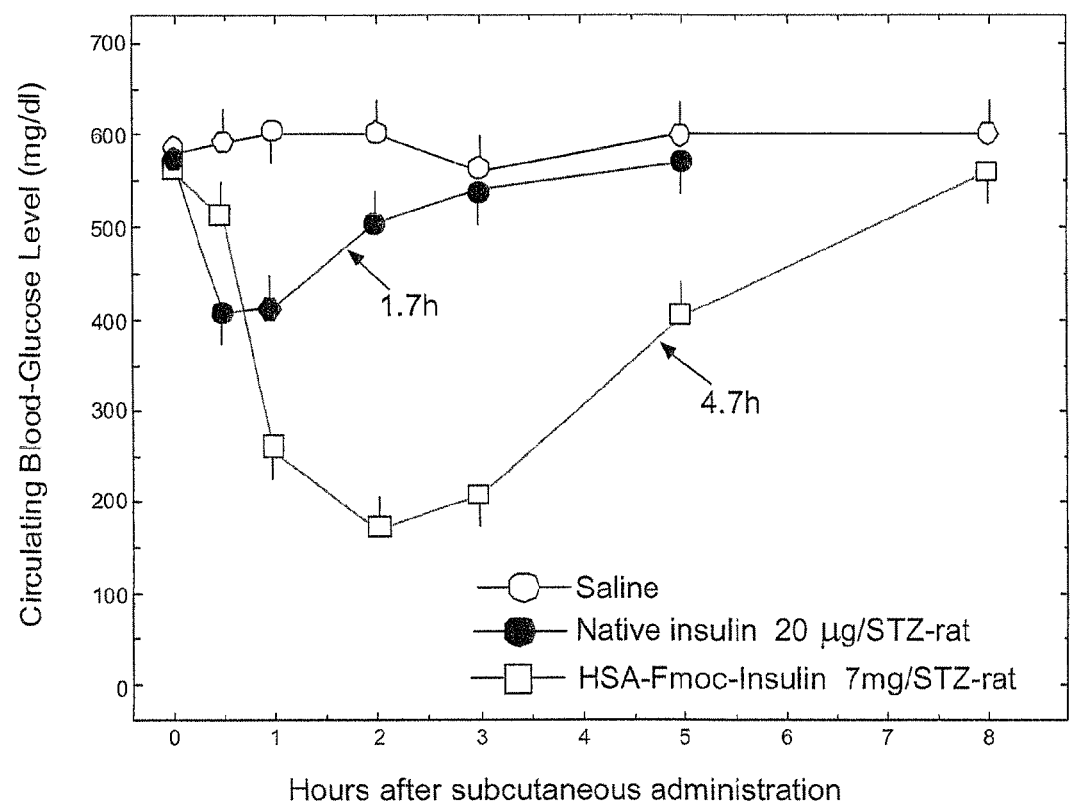

FIG. 29 shows the effect of a single subcutaneous administration of HSA-Fmoc-insulin on blood glucose levels in STZ-rats. STZ-rats received saline solution (control group), Zn2+-free insulin (20 μg/STZ rat) or HSA-Fmoc-insulin (7 mg/STZ-rat). Blood glucose levels were determined at the time points indicated in the Figure. Each point represents the arithmetic mean of the blood glucose levels of n=5 rats±SE.

DETAILED DESCRIPTION OF THE INVENTION

The present invention provides a new conceptual approach for delivery of drugs, particularly peptides and proteins of low or medium molecular weight, by natural or synthetic carriers, whereby the carrier moiety and the drug residue are not linked directly to each other or the drug molecule is not encapsulated within the carrier, as in standard drug delivery using such carriers, but rather both residues are linked to different positions of a scaffold structure that is highly sensitive to bases and is removable under physiological conditions.

The carrier used in the present invention may be a protein such as albumin or a modified albumin, e.g., cationized bovine serum albumin (CBSA) or cationized human serum albumin (CHSA), or a protein containing globin-like domains having long half-life in circulation, e.g., a hemoglobin-like protein such as hemoglobin A or S.

In one embodiment, the protein carrier is albumin, namely, human serum albumin (HSA). In another embodiment, the protein carrier is cationized albumin. Cationized albumin (pI greater than 8), unlike native albumin (pI approximately 4), enters cerebrospinal fluid (CSF) rapidly from blood. This suggests that a specific uptake mechanism for cationized albumin may exist at the brain capillary wall, i.e. the blood-brain barrier, and thus it may be used for brain targeting. Cationized albumins may be obtained, for example, by substituting anionic carboxyl groups with cationic aminoethyl-amide groups. The cationized albumin may be linked to the drug through the scaffold containing the structure that is highly sensitive to bases and is removable under physiological conditions or it may be conjugated with a polymer such as poly(ethyleneglycol)-poly(lactide) (PEG-PLA) nanoparticles (CBSA-NP), designed for brain drug delivery. The CBSA is covalently conjugated with the maleimide function group at the distal of PEG surrounding the nanoparticles. The cationized albumin may also be coupled to sterically stabilized liposomes.

In another embodiment, the carrier is a polymer carrier moiety such as, but not limited to, linear or branched poly-ethylene glycol (PEG) and block copolymers thereof, poly(lactic acid) and copolymers thereof, polyesters having suitable functional groups based on polylactide (PLA), polyglycolide (PGA), polycaprolactone (PCL), and their copolymers, and polyamides based on polymethacrylamide and their copolymers. All these polymers should have suitable functional groups for linking to a scaffold structure of the formula (i)-(iv) that is highly sensitive to bases and is removable under physiological conditions, preferably through a spacer. Examples of the polymer carriers include PEG, poly (lactic acid)-block-polyethylene glycol, N-(2-hydroxypropyl)methacrylamide (HMPA) copolymer with suitable functional groups or poly-D,L-lactide-co-glycolide (PLGA) nanoparticles. The functional groups may be hydroxy, amino, carboxyl, mercapto, sulfonic acid group, and the like.

The polymer may also be a block polymer as disclosed in U.S. Pat. No. 5,929,177, herein incorporated by reference in its entirety as if fully disclosed herein. These block polymers have functional groups, e.g., amino group, carboxyl group or mercapto group on α-terminal, and hydroxyl group, carboxyl group, aldehyde group or vinyl group on ω-terminal, and comprise hydrophilic/hydrophobic segments. Hydrophilic segment comprises polyethylene oxide, while hydrophobic segment is derived from lactide, lactone or (meth)acrylic acid ester. These block polymers form polymeric micelles which are usable as bio-compatible materials.

The invention also encompasses as polymer carriers liposomes containing phospholipids with covalently attached poly(ethylene glycol) (PEG-lipids).

Polymer carriers have several advantages over other delivery methods such as liposomes and antibodies. Because liposomes—spherical vesicles made of phospholipids—are particles, they get taken up by macrophages. High levels can be found in the liver and spleen, even when the liposomes are given "stealth" characteristics by coating them with PEG. In contrast, water-soluble polymers allow working with a single molecule rather than a large particle. It is possible to choose a material which doesn't go to the liver and the spleen. It is in effect a 'macromolecular prodrug'. To avoid the liver and spleen, one can use uncharged hydrophilic polymers, such as PEG and N-(2-hydroxypropyl)-methacrylamide. When these polymers are hydrated, they can circulate in the blood for periods of up to about 24 hours.

In one preferred embodiment, the polymeric carrier is in the form of nanoparticles. Nanoparticle drug delivery, utilizing degradable and absorbable polymers, provides a more efficient, less risky solution to many drug delivery challenges. Nanoparticles are generally defined as particles between 10 nanometers (nm) and 1000 nm in size, and can be either spherical or vesicular, The advantages of using polymeric nanoparticles (PNPs) in drug delivery are many, the most important being that they generally increase the stability of any volatile pharmaceutical agents and that they are easily and cheaply fabricated in large quantities by a multitude of methods. Additionally, the use of absorbable or degradable polymers, such as polyesters, provides a high degree of biocompatibility for PNP delivery systems. Among the adaptations that can be made are surface modifications of the polymer, use of different fabrication methods, selection of a variety of pre-existing polymers or copolymers. In one embodiment, the polymer carrier are nanoparticles of organically modified silica.

In one preferred embodiment of the invention, the polymer carrier is PEG. The present invention thus provides a new conceptual approach for reversible pegylation of drugs, particularly peptides and proteins of low or medium molecular weight, whereby the PEG moiety and the drug residue are not linked directly to each other, as in standard pegylation procedures, but rather both residues are linked to different positions of a scaffold structure that is highly sensitive to bases and is removable under physiological conditions.

In one aspect, the present invention provides a compound of the formula:

$(X)_n$—Y wherein

Y is a moiety of a drug bearing at least one functional group selected from free amino, carboxyl, phosphate, hydroxyl and/or mercapto, and X is a radical selected from the group of radicals consisting of the formulas (i) to (iv):

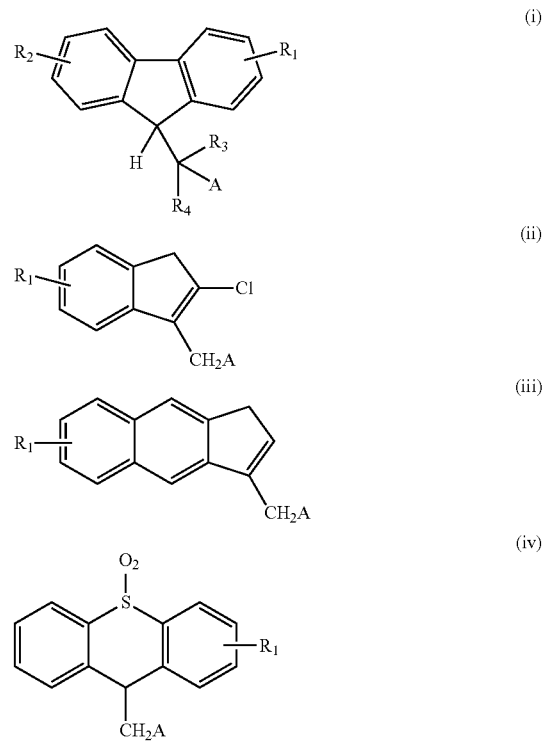

wherein:

$R_1$ is a radical containing a protein or polymer carrier moiety; polyethylene glycol (PEG) moiety;

$R_2$ is selected from the group consisting of hydrogen, alkyl, alkoxy, alkoxyalkyl, aryl, alkaryl, aralkyl, halogen, nitro, —$SO_3H$, —$SO_2NHR$, amino, ammonium, carboxyl, $PO_3H_2$, and $OPO_3H_2$;

R is selected from the group consisting of hydrogen, alkyl and aryl;

$R_3$ and $R_4$, the same or different, are each selected from the group consisting of hydrogen, alkyl and aryl;

A is a covalent bond when the radical is linked to a carboxyl, phosphate or mercapto group of the drug Y, or A is OCO— when the radical is linked to an amino or hydroxyl group of the drug Y;

n is an integer of at least one, and pharmaceutically acceptable salts thereof.

The terms "alkyl", "alkoxy", "alkoxyalkyl", "aryl", "alkaryl" and "aralkyl" in the definitions of $R_1$, $R_2$, $R_3$ and $R_4$ herein are used to denote alkyl radicals of 1-8, preferably 1-4 carbon atoms, e.g. methyl, ethyl, propyl, isopropyl and butyl, and aryl radicals of 6-10 carbon atoms, e.g. phenyl and naphthyl. The term "halogen" includes bromo, fluoro, chloro and iodo.

In one preferred embodiment of the invention, X is a radical of the formula (i), more preferably a radical of formula (i) wherein $R_2$, $R_3$ and $R_4$ are each hydrogen and A is —OCO—, namely the 9-fluorenylmethoxycarbonyl radical (hereinafter "Fmoc"), or most preferably, a radical of formula (i) wherein $R_2$ is —$SO_3H$ at position 2 of the fluorene ring, $R_3$ and $R_4$ are each hydrogen, and A is —OCO—, namely the 2-sulfo-9-fluorenylmethoxycarbonyl radical (hereinafter "FMS").

In another embodiment of the invention, the functional group is the radical (i), wherein $R_2$, $R_3$ and $R_4$ are hydrogen and A is a covalent bond, i.e. the 9-fluorenylmethyl (Fm) group, which is applicable for reversible masking of free mercapto groups, of carboxylic functions of aspartic and glutamic acid moieties, and of C-terminal carboxyl functions of the cytokine molecules. The resulting 9-fluorenylmethyl esters (Fm-esters) generate the parent free carboxylic functions following a β-elimination reaction pathway upon mild basic treatment, and thus can be similarly employed for reversible masking of carboxylic functions of drugs. The Fmoc-group is of further potential similar use in the reversible protection of hydroxyl groups of tyrosine, serine and threonine.

The halogenated Fmoc radicals (i) wherein $R_2$ is halogen in the 2 or 7 position, preferably Cl or Br, the 2-chloro-1-indenylmethoxycarbonyl (CLIMOC) radical (ii), the 1-benzo[f]indenylmethoxycarbonyl urethane (BIMOC) radical (iii), the urethane sulfone radical (iv) and corresponding radicals (i) to (iv) wherein A is a covalent bond, can be used similarly to Fmoc and Fm for substitution of free amino, carboxyl, hydroxyl and mercapto functions of drugs, thus providing a wide range of sensitivity toward removal of such groups under basic, e.g. physiological, conditions. In fact, the above radicals (i) to (iv) belong to a general family of rare chemical entities that undergo hydrolysis at neutral or slightly alkaline pH and mild conditions, and can therefore be used for temporary reversible protection of α- and ε-amino groups, for example in peptide synthesis, and can be removed from the amino function by a β-elimination reaction, under mild basic conditions.

According to the invention, a radical (i) to (iv), preferably Fmoc or FMS covalently linked to amino and/or hydroxyl moieties or Fm covalently linked to carboxyl and/or mercapto moieties, undergoes hydrolysis (via β-elimination) back to the free amino, hydroxy, mercapto or carboxyl functions, under physiological conditions in the body fluid, namely at pH 7.4 and 37° C.

In one embodiment, R1 contains a protein carrier, preferably albumin, linked through a spacer to the ring. In another embodiment, R1 contains a polymer carrier moiety; linked through a spacer to the ring. Preferably, the polymer carrier is a polyethylene glycol (PEG) moiety.

In one embodiment of the invention, $R_1$ is a radical of the formula:

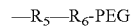

wherein $R_5$ is selected from the group consisting of —NH—, —S—, —CO—, —COO—, —$CH_2$—, —$SO_2$—, —$SO_3$—, —$PO_2$—, and —$PO_3$—; and $R_6$ is a bond or a radical by which the PEG moiety is covalently attached to $R_5$.

In a more preferred embodiment, $R_5$ is —NH—, and $R_6$ is selected from the group consisting of —CO—, —COO—, —$CH_2$—, —$CH(CH_3)$—, CO—NH—, —CS—NH, —CO—$CH_2$—NH—CO—, —CO—$CH(CH_3)$—NH—CO—, —CO—$CH_2$—NH—CO—NH,

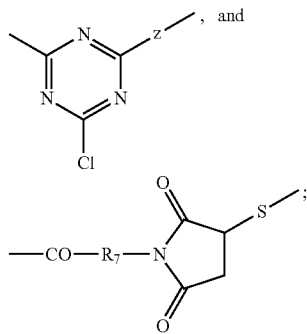

Z is O, S or NH; and $R_7$ is selected from the group consisting of C1-C18 straight or branched alkylene, phenylene, an oxyalkylene radical having 3-18 carbon atoms in the backbone, a residue of a peptide containing 2-10 amino acid residues, and a residue of a saccharide containing 1-10 monosaccharide residues.

In the 4-chloro-6-Z-triazin-2-yl radical above, the 6-Z-group is linked to the PEG moiety while the 2 position is linked to $R_5$, which is —NH— in this case. In the —CO—$R_7$-succinimido radical above, the thio —S— group at position 3 is linked to the PEG moiety while the —CO— is linked to $R_5$, which is —NH— in this case.

In one preferred embodiment, the pegylated drug compound of the invention is a conjugate of the formula:

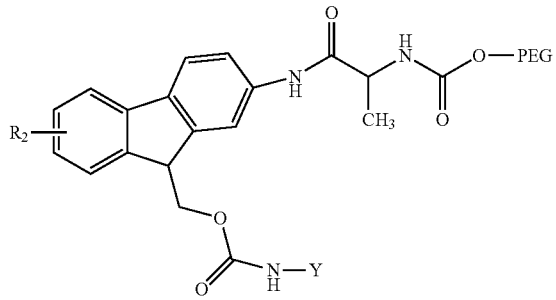

wherein $R_2$ is H or —$SO_3H$ at position 2 of the fluorene ring, and Y is preferably a peptide or protein drug. When $R_2$ is H, a herein designated PEG-Fmoc-drug Y conjugate is obtained. In a most preferred embodiment, $R_2$ is —$SO_3H$ at position 2 of the fluorene ring, and a herein designated PEG-FMS-drug Y conjugate is obtained.

In a more preferred embodiment, the pegylated drug of the invention is a compound of the formula:

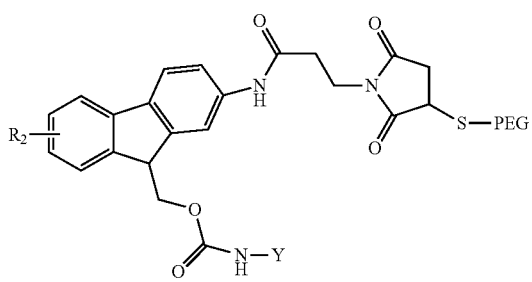

wherein $R_2$ is H or —$SO_3$H.

In a most preferred embodiment, the pegylated drug of the invention is a compound of the formula above, wherein $R_2$ is —$SO_3$H at position 2 of the fluorene ring, and the PEG moiety is a 40 kDa branched PEG. These conjugates are herein identified as (PEG$_{40}$-FMS)$_n$-peptide/protein, wherein n is 1 to 3, preferably 1 or 2, most preferably 1.

The above compounds of the invention wherein $R_5$ is —NH— can be prepared from N-(9-fluorenylmethoxy-carbonyloxy)-succinimide (Fmoc-OSu) or N-(2-sulfo-9-fluorenylmethoxy-carbonyloxy)-succinimide (FMS-OSu) substituted by —NH$_2$ in the fluorene ring (depicted in Scheme 7, page a, first row, first column), by reacting the amino group with the activated PEG-OH (e.g. PEG-O—CO—Cl) or an activated derivatized PEG such as PEG-carboxylate (PEG-COOH, e.g. via PEG-CO—Cl), PEG-aldehyde (PEG-CHO), PEG-isocyanate (PEG-N=C=O), PEG-isothiocyanate (PEG-N=C=S), 2,4-dichloro-6-S-PEG-1,3,5-triazine, 2,4-dichloro-6-NH-PEG-1,3,5-triazine, or 2,4-dichloro-6-O-PEG-1,3,5-triazine (Scheme 7, page a, right column) in order to obtain the derivatives wherein —$R_6$-PEG is as presented in Scheme 7 (page a, middle column).

In one preferred embodiment of the invention, the conjugate of the invention is a (PEG-Fmoc)$_n$-peptide/protein, and the starting compound for their preparation is the maleimido derivative of Fmoc-OSu, herein designated Precursor 7 or MAL-Fmoc-NHS or MAL-Fmoc-OSu, of the formula depicted in Scheme 3.

In a most preferred embodiment of the invention, the conjugate of the invention is a (PEG-FMS)$_n$-peptide/protein, and the starting compound for their preparation is the maleimido derivative of FMS-OSu, herein designated Precursor 8 or MAL-FMS-NHS or MAL-FMS-OSu, of the formula depicted in Scheme 3.

Two possible pathways for the pegylation of target peptides/proteins and preparation of the (PEG-Fmoc)$_n$-peptide/protein or (PEG-FMS)$_n$-peptide/protein conjugates are provided by the invention, as depicted in Scheme 6. Both pathways are two-step procedures.

According to one pathway, MAL-FMS-NHS or MAL-Fmoc-NHS is first attached to the amine component of the target peptide/protein, thus obtaining a MAL-FMS-peptide/protein or MAL-Fmoc-peptide/protein conjugate, and then substituting PEG-SH for the maleimide moiety, producing the (PEG-FMS)$_n$-peptide/protein or (PEG-Fmoc)$_n$-peptide/protein conjugate, respectively.

In the second pathway, MAL-FMS-NHS or MAL-Fmoc-NHS is first reacted with PEG-SH, thus forming a PEG-FMS-NHS or PEG-Fmoc-NHS conjugate, and then reacting it with the amine component of the target peptide or protein resulting in the desired (PEG-FMS)$_n$-peptide/protein or (PEG-Fmoc)$_n$-peptide/protein conjugate, respectively. This pathway is suitable for sulfhydryl- or disulfide-containing peptides and proteins.

The compounds wherein $R_5$ is —NH— and $R_6$ is —CO—NH— or —CS—NH— can be prepared from Fmoc-OSu or FMS-OSu substituted by —N=C=O or —N=C=S in the fluorene ring (depicted in Scheme 7, page C, first row and last rows, first column), respectively, by reaction with PEG-NH$_2$. No activation is necessary because these Fmoc/FMS species are already activated.

In a further embodiment of the invention, $R_5$ is —S—; and $R_6$ is selected from the group consisting of

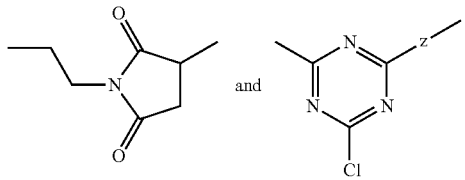

wherein Z is O, S or NH.

The above compounds of the invention wherein $R_5$ is —S— can be prepared from Fmoc-OSu or FMS-OSu substituted by —SH in the fluorene ring (depicted in Scheme 7, page b, second row, first column), by reaction with PEG-maleimide of the formula shown in Scheme 7, page b, second row, right column), thus obtaining a pegylated compound of the invention wherein the PEG moiety is linked to the fluorene ring trough a residue as depicted in Scheme 7, page b, second row, middle column, or by reaction with 2,4-dichloro-6-S-PEG-1,3,5-triazine, 2,4-dichloro-6-NH-PEG-1,3,5-triazine, or 2,4-dichloro-6-O-PEG-1,3,5-triazine.

In yet another embodiment, in the pegylated drug of the invention, $R_5$ is —CO; $R_6$ is selected from the group consisting of —O—; —NH—; —NH—$R_7$—COO—; —NH—$R_7$—NH; —NH—$R_7$—CO—NH;

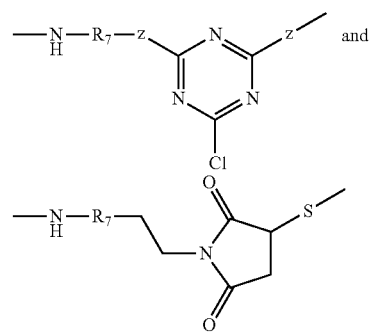

Z is O, S or NH; and $R_7$ is selected from the group consisting of C1-C18 straight or branched alkylene, phenylene, an oxyalkylene radical having 3-18 carbon atoms in the backbone, a residue of a peptide containing 2-10 amino acid residues, and a residue of a saccharide containing 1-10 monosaccharide residues.

The above compounds of the invention wherein $R_5$ is —CO— can be prepared from Fmoc-OSu or FMS-OSu substituted by —COOH in the fluorene ring (depicted in Scheme 7, page b, third row, first column). When $R_6$ is —O— or —NH—, the reaction will occur with PEG (PEG-OH) or PEG-amine (PEG-NH$_2$), respectively, thus obtaining a pegylated compound wherein the PEG moiety is linked to the fluorene ring trough a residue —CO—O— or —CO—NH—, respectively, as depicted in Scheme 7, page b, middle column (3$^{rd}$ and 4$^{th}$ rows).

The compounds of the invention wherein $R_5$ is —CO— and $R_6$ is NH—$R_7$—COO— can be prepared from Fmoc-OSu or FMS-OSu substituted by —COOH in the fluorene ring, by reaction with $H_2N$—$R_7$—CO-OtBu using a coupling reagent (e.g. DCC/HOBt, or PyBOP(benzotriazol-1-yloxy) tripyrrolidinophosphonium hexa-fluorophosphate)/triethylamine), removal of the tBu protecting group under acidic conditions (e.g. trifluoroacetic acid or HCl in dioxane), activation of the free carboxyl group by triphosgen and reaction of the —NH—$R_7$—COCl formed with PEG-OH to obtain the —CO—NH—$R_7$—CO—O-PEG derivative.

The compounds of the invention wherein $R_5$ is —CO— and $R_6$ is NH—$R_7$—NH can be prepared from Fmoc-OSu or FMS-OSu substituted by —COOH in the fluorene ring, by reaction with $H_2N$—$R_7$—NH-tBu using a coupling reagent and removing the tBu protecting group as described above, reacting the free amino group with PEG-OSu to obtain the —CO—NH—$R_7$—NH-PEG derivative.

The compounds of the invention wherein $R_5$ is —CO— and $R_6$ is NH—$R_7$—CO—NH— can be prepared from Fmoc-OSu or FMS-OSu substituted by —COOH in the fluorene ring, by reaction with $H_2N$—$R_7$—CO—NH-tBu using a coupling reagent and removing the tBu protecting group as described above, activating the free carboxyl group with DCC/NHS and reacting of the —NH—$R_7$—CO—N-hydroxysuccinimide ester formed with PEG-$NH_2$ to obtain the —CO—NH—$R_7$—CO—NH-PEG derivative.

The compounds of the invention wherein $R_5$ is —CO— and $R_6$ is —NH—$R_7$—NH—Z-(4-chloro-6-Z-PEG-1,3,5-triazin-2-yl can be prepared from Fmoc-OSu or FMS-OSu substituted by —COOH in the fluorene ring, by reaction with $H_2N$—$R_7$—NH-tBoc or $H_2N$—$R_7$—O-tBu or $H_2N$—$R_7$—S-trityl using a coupling reagent and removing the tBoc, tBu or trityl protecting group as described above, reacting the free $NH_2$, OH or SH group with 2,4,6-trichloro-1,3,5-triazine, and further reacting the —NH—$R_7$—NH[O or S]-(4-chloro-6-NH[O or S]-1,3,5-triazin-2-yl thus formed with PEG-$NH_2$, PEG-OH or PEG-SH to obtain the corresponding —CO—NH—$R_7$—NH[O or S]-(4-chloro-6-NH[O or S]-PEG-1,3,5-triazine derivative.

The compounds of the invention wherein $R_5$ is —CO— and $R_6$ is NH—$R_7$-ethylene-succinimido can be prepared from Fmoc-OSu or FMS-OSu substituted by —COOH in the fluorene ring, by reaction with $H_2N$—$R_7$-ethylene-maleimide using a coupling reagent (e.g. DCC/HOBt, PyBoP/Triethylamine) followed by reaction of the maleimide moiety with PEG-SH at pH 6-8 to obtain the —CO—NH—$R_7$-ethylene-succinimido-S-PEG derivative.

The pegylated-Fmoc/FMS-drugs of the invention are then prepared from these intermediates by the one-step procedure described in Example 5 hereinafter.

In yet a further embodiment of the invention, $R_5$ is —$CH_2$—; and $R_6$ is —$(CH_2)_n$—S— or —$(CH_2)_n$—NH—, wherein n is 0 to 18, preferably 1.

The above compounds of the invention wherein $R_5$ is —$CH_2$— and $R_6$ is —$CH_2$—S— or —$R_6$ is —$CH_2$—NH— can be prepared from Fmoc-OSu or FMS-OSu substituted by —COH in the fluorene ring (depicted in Scheme 7, page c, $4^{th}$ row, first column), by reaction with PEG-SH or PEG-$NH_2$ followed by reduction with $NaHBH_3$, respectively.

The above compounds of the invention wherein $R_5$ is —$CH_2$— and $R_6$ is —$(CH_2)_n$—S— or $R_6$ is —$(CH_2)_n$—NH— can be prepared from Fmoc-OSu or FMS-OSu substituted by —$(CH_2)_n$-Hal in the fluorene ring, wherein Hal is F, Cl, Br or I (depicted in Scheme 7, page d, $3^{rd}$ row, first column), by reaction with PEG-$NH_2$ or PEG-SH, thus obtaining a pegylated compound of the invention wherein the PEG moiety is linked to the fluorene ring trough a residue as depicted in Scheme 7, page d, middle column, $3^{rd}$ and $4^{th}$ rows, respectively.

The pegylated-Fmoc/FMS-drugs of the invention are then prepared from the above intermediates by the one-step procedure described in Example 5 hereinafter.

In still another embodiment, $R_5$ is —$SO_2$— and $R_6$ is —O—, —NH— or —$CH_2$—$CH_2$—S. The compounds wherein $R_6$ is —O— or —NH— can be prepared from Fmoc-OSu or FMS-OSu substituted by —$SO_2Cl$ in the fluorene ring (depicted in Scheme 7, page c, first column, $3^{rd}$ row), by reaction with PEG-OH or PEG-$NH_2$, respectively. The pegylated-Fmoc/FMS-drugs of the invention are then prepared from these intermediates by the one-step procedure described in Example 5 hereinafter.

The compounds wherein $R_6$ is —$CH_2$—$CH_2$—S, can be prepared from Fmoc-OSu or FMS-OSu substituted by —$SO_2CH$=$CH_2$ in the fluorene ring (depicted in Scheme 7, page c, first column, $2^{nd}$ row), by reaction with PEG-SH. The pegylated-Fmoc/FMS-drugs of the invention are then prepared from these intermediates by the two-step procedure described in Examples 16 or 17 hereinafter.

In yet still another embodiment, $R_5$ is —$PO_2$— and $R_6$ is —O— or —NH—. These compounds can be prepared from Fmoc-OSu or FMS-OSu substituted by —$PO_2Cl$ in the fluorene ring (depicted in Scheme 7, page d, first column, first row), by reaction with PEG-OH or PEG-$NH_2$, respectively. The pegylated-Fmoc/FMS-drugs of the invention are then prepared from these intermediates by the one-step procedure described in Example 5 hereinafter.

According to the present invention, Y is a moiety of a drug bearing at least one functional group selected from free amino, carboxyl, hydroxyl, phosphate and/or mercapto. In a more preferred embodiment of the invention, the drug contains at least one free amino group and is a peptide or a protein drug or a non-peptidic drug.

In one embodiment of the invention, the drug is a non-peptidic drug that contains at least one amino group and the invention relates to PEG-Fmoc and PEG-FMS conjugates thereof. Non-peptidic drugs that are amenable to the technology of the invention include antibiotic aminoglycosides such as gentamicin and amphotericin B, and antineoplastic drugs such as aminolevulinic acid, daunorubicin and doxorubicin.

In a more preferred embodiment of the invention, the drug containing at least one amino group is a peptide or protein drug, most preferably a peptide or protein of low or medium molecular weight, that can be used as a drug for human or veterinary use.

Thus, further provided by the invention are pegylated drug conjugates PEG-FMS-Y and PEG-Fmoc-Y herein identified by the formulas:

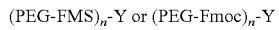

(PEG-FMS)$_n$-Y or (PEG-Fmoc)$_n$-Y wherein Y is a moiety of a peptide or protein drug, n is an integer of at least one, preferably 1 or 2, and Y is linked to the FMS or Fmoc radical through at least one amino group. In the most preferred embodiment the conjugate is (PEG-FMS)$_n$-Y and the PEG moiety is PEG$_{40000}$.

Examples of peptides and proteins Y that can be pegylated according to the invention include, but are not limited to, insulin, an interferon such as IFN-α2, a PYY agonist such as the peptide PYY$_{3-36}$, an exendin such as exendin-3 and exendin-4 and exendin analogues and agonists, atrial natriuretic peptide (ANP), human growth hormone (hGH), erythropoietin, TNF-α, calcitonin, gonadotropin releasing hormone (GnRH) or an analogue thereof such as leuprolide and D-Lys[6]-GnRH, hirudin, glucagon, and a monoclonal antibody fragment such as anti-TNF-α monoclonal antibody fragment.

In one preferred embodiment of the invention, the peptidic drug is insulin and the invention provides PEG-Fmoc-insulin and PEG-FMS-insulin conjugates and pharmaceutical compositions comprising them for treatment of diabetes mellitus and hyperglycemia. Examples of such conjugates are the $(PEG_{5000}$-Fmoc$)_1$-insulin, $(PEG_{5000}$-Fmoc$)_2$-insulin and $PEG_{40000}$-FMS-insulin conjugates.

In another preferred embodiment of the invention, the drug is an exendin or an exendin agonist.

In a more preferred embodiment, the drug is exendin-4 of the sequence represented by SEQ. ID. NO:1:

```
HGEGTFTSDL SKQMEEEAVR LFIEWLKNGG PSSGAPPPS-NH2
```

In another preferred embodiment, the drug is exendin-3 of the sequence represented by SEQ. ID. NO:2:

```
HSDGTFITSDL SKQMEEEAVR LFIEWLKNGG PSSGAPPPS-NH2
```

In a further preferred embodiment, the drug is an exendin agonist defined herein as a compound that mimics the activities of exendin-3 or exendin-4 by binding to the receptor(s) at which exendin-3 or exendin-4 exerts its actions which are beneficial as insulinotropic and in the treatment of diabetes mellitus or by mimicking the effects of exendin on increasing urine flow, increasing urinary sodium excretion and/or decreasing urinary potassium concentration, by binding to the receptor(s) where exendins cause these effects. Preferably, the exendin agonist is selected from the group of insulinotropic exendin-4 fragments and analogues consisting of exendin agonists represented by SEQ ID NO:3 to SEQ ID NO: 10:

```
exendin-4 (1-31)
                                            [SEQ ID No: 3]
HGEGTFTSDLSKQMEEEAVRLFIEWLKNGGP;

Y31 exendin-4(1-31)
                                            [SEQ ID No: 4]
HGEGTFTSDLSKQMEEEAVRLFIEWLKNGGY;

exendin-4 (1-30)
                                            [SEQ ID No: 5]
HGEGTFTSDLSKQMEEEAVRLFIEWLKNGG;

exendin-4 (1-30) amide
                                            [SEQ ID No: 6]
HGEGTFTSDLSKQMEEEAVRLFIEWLKNGG-NH2;

exendin-4 (1-28) amide
                                            [SEQ ID No: 7]
HGEGTFTSDLSKQMEEEAVRLFIEWLKN-NH2;

L14, F25 exendin-4 amide
                                            [SEQ ID No: 8]
HGEGTFTSDLSKQLEEEAVRLFIEFLKNGGPSSGAPPPS-NH2;

L14, F25 exendin-4 (1-28) amide
                                            [SEQ ID No: 9]
HGEGTFTSDLSKQLEEEAVRLFIEFLKN-NH2;
and L14, A22, F25 exendin-4 (1-28) amide
                                            [SEQ ID No: 10]
HGEGTFTSDLSKQLEEEAVRLAIEFLKN-NH2.
```

According to this embodiment, the invention provides PEG-Fmoc-exendin/exendin agonist and PEG-FMS-exendin/exendin agonist conjugates and pharmaceutical compositions comprising them for prevention of hyperglycemia and for treatment of diabetes mellitus selected from the group consisting of non-insulin dependent diabetes mellitus, insulin-dependent diabetes mellitus, and gestational diabetes mellitus. In a most preferred embodiment, the pegylated exendin conjugate of the invention is $PEG_{40}$-FMS-exendin-4.

In a further preferred embodiment of the invention, the peptidic drug is an interferon, preferably IFN-α, and the invention provides PEG-Fmoc-IFN-α and PEG-FMS-IFN-α conjugates and pharmaceutical compositions comprising them for treatment of diseases treatable by IFN-α, particularly viral diseases, more particularly hepatitis B or C, both as sole therapy or in conjunction with an antiviral agent such as ribavirin, or for treatment of cancer, e.g. transitional cell carcinoma, the most common type of bladder cancer, ovarian cancer, pancreatic cancer melanoma, non-Hodgkin's lymphoma, hairy cell leukemia, and AIDS-related Kaposi's sarcoma, both as sole therapy or in conjunction with a cytotoxic agent such as carboplatin and/or cyclophosphamide. In a more preferred embodiment, the conjugate is $(PEG_{40}$-FMS$)_2$—IFNα2 or, most preferably, $PEG_{40}$-FMS-IFNα2.

In still another preferred embodiment of the invention, the peptidic drug is a PYY agonist, herein defined as a molecule that has a PYY- or PYY[3-36]-like biological activity such as reducing food intake in mammals, and acts by a mechanism similar to that of PYY and PYY[3-36], for example by binding to the Y2 receptor. The PYY agonist is preferably an agonist specific for the Y2 receptor and is preferably a peptide containing, at a minimum, the sequence of amino acids 25-36 of PYY, most preferably the sequence 3-36 of PYY.

In one embodiment of the invention, the PYY agonist is the 36-mer peptide PYY of the sequence represented by SEQ ID NO: 11:

```
YPIKPEAPGEDASPEELNRYYASLRHYLNLVTRQRY-NH2
```

In a more preferred embodiment of the invention, the PYY agonist is the peptide PYY[3-36] of the sequence represented by SEQ ID NO: 12:

```
IKPEAPGEDASPEELNRYYASLRHYLNLVTRQRY-NH2
```

According to this embodiment, the invention provides PEG-Fmoc-PYY agonist and PEG-FMS-PYY agonist conjugates and pharmaceutical compositions comprising them for particularly for reduction of food intake, for inducing weight loss and for the treatment of diseases or disorders which can be alleviated by reduction of food intake such as obesity, hypertension, dyslipidemia, cardiovascular risk, insulin-resistance, and diabetes mellitus (particularly type II diabetes). In a preferred embodiment, the pegylated PYY agonist of the invention is $PEG_{40}$-FMS-PYY$_{3-36}$.

In another preferred embodiment, the peptidic drug is human growth hormone (hGH) and the invention provides PEG-Fmoc-hGH and PEG-FMS-hGH conjugates and pharmaceutical compositions comprising them for treatment of conditions and disorders treatable by hGH, particularly for treatment of children of pathologically short stature and as anti-aging agent. In preferred embodiments, the pegylated hGH conjugates of the invention are $(PEG_{40}$-FMS$)_2$-hGH and PEG-FMS-hGH.

In a further preferred embodiment of the invention, the peptidic drug is atrial natriuretic peptide (ANP) or an analog thereof, particularly the cyclic 28-amino acid ANP of the sequence represented by SEQ ID NO:13, as follows:

```
Ser-Leu-Arg-Arg-Ser-Ser-[Cys7-Phe-Gly-Gly-Arg-
Met-Asp-Arg-Ile-Gly-Ala-Gln-Ser-Gly-Leu-Gly-
Cys23]-Asn-Ser-Phe-Arg-Tyr
```

According to this embodiment, the invention provides PEG-Fmoc-ANP and PEG-FMS-ANP conjugates and pharmaceutical compositions comprising them for treatment of conditions and disorders treatable by the invention provides PEG-Fmoc-ANP and PEG-FMS-ANP conjugates and pharmaceutical compositions comprising them for treatment of conditions and disorders treatable by natriuretic peptides and variants thereof, particularly treatment of cardiovascular diseases, congestive heart failure, hypertension, acute kidney failure and adult respiratory distress syndrome (ARDS). In one preferred embodiment of the invention, the pegylated ANP is the $PEG_{40}$-FMS-ANP conjugate.

Also included in the scope of the invention are pharmaceutically acceptable salts of the pegylated conjugates of the invention. As used herein, the term "salts" refers to both salts of carboxyl groups and to acid addition salts of amino groups of the drug, e.g. peptide or protein, molecule. Salts of a carboxyl group may be formed by means known in the art and include inorganic salts, for example, sodium, calcium, ammonium, ferric or zinc salts, and the like, and salts with organic bases such as those formed for example, with amines, such as triethanolamine, arginine, or lysine, piperidine, procaine, and the like. Acid addition salts include, for example, salts with mineral acids such as, for example, hydrochloric acid or sulfuric acid, and salts with organic acids, such as, for example, acetic acid or oxalic acid.

The present invention further relates to methods for the preparation of the pegylated conjugates of the invention and to several novel precursor compounds used in these methods.

Thus, the present invention also relates to a precursor of the formula:

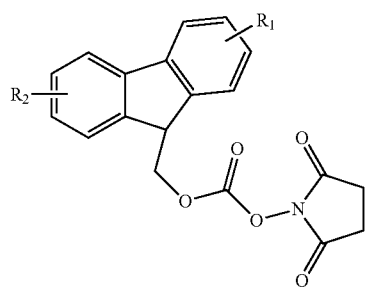

wherein:

$R_1$ is a radical of the formula —$R_5$—$R_6$—B;

$R_2$ is H or —$SO_3H$ at position 2 of the fluorene ring;

B is maleimido, —S—CO—$CH_3$ or a PEG moiety;

$R_5$ is selected from the group consisting of —NH—, —S—, —CO—, —COO—, —$CH_2$—, —$SO_2$—, —$SO_3$—, —$PO_2$—, and —$PO_3$—; and $R_6$ is a bond or a radical by which the maleimido, —S—CO—$CH_3$ or PEG moiety is attached to $R_5$.

In one preferred embodiment, $R_5$ is NH—; $R_6$ is selected from the group consisting of —CO—, —COO—, —$CH_2$—, —CH($CH_3$)—, CO—NH—, —CS—NH—, —CO—$CH_2$— NH—CO—, —CO—CH($CH_3$)—NH—CO—, —CO— $CH_2$—NH—CO—NH, —CO—$R_8$—;

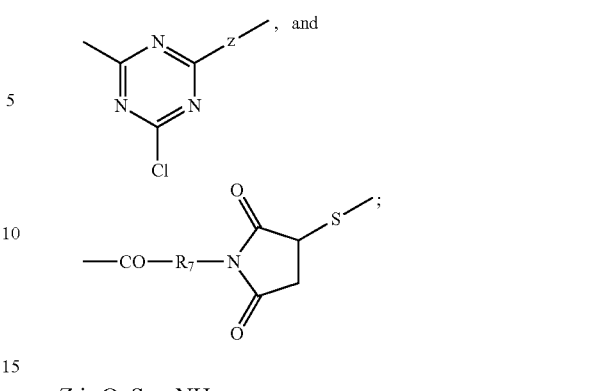

Z is O, S or NH;

$R_7$ is selected from the group consisting of C1-C18 straight or branched alkylene, phenylene, an oxyalkylene radical having 3-18 carbon atoms in the backbone, a residue of a peptide containing 2-10 amino acid residues, and a residue of a saccharide containing 1-10 monosaccharide residues; and $R_8$ is a C1-C8 straight or branched alkylene, preferably ethylene, when B is maleimido or —S—CO—$CH_3$.

In one preferred embodiment, the invention relates to the novel Precursors 1-7, whose formulas are depicted in Schemes 1 and 3. In the most preferred embodiment, the invention relates to the compound herein identified as Precursor 8 or MAL-FMS-NHS of the formula:

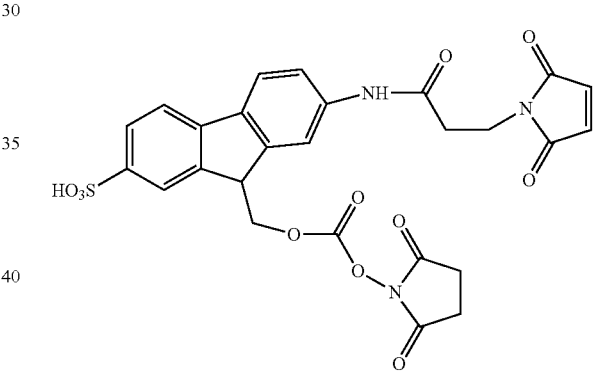

Precursor 8 is the compound N-[2-(maleimido-propionyl amino)-7-sulfo-fluoren-9-yl-methoxycarbonyloxy]-succinimide [or 9-hydroxymethyl-2-(amino-3-maleimidopropionate)-7-sulfo-fluorene-N-hydroxysuccinimide] and is also herein identified as MAL-FMS-OSu.

MAL-FMS-NHS is a water-soluble hetero-bifunctional reagent, consisting of a sulfonated fluorenyloxycarbonyl N-hydroxysuccinimide ester that reacts with peptide and protein amino groups. A maleimide group was attached to the fluorenyl backbone to enable coupling to sulfhydryl-containing PEG, most preferably $PEG_{40000}$-SH.

Thus, further provided by the invention are precursor drug conjugates herein identified by the formula:

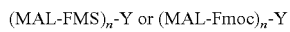

(MAL-FMS)$_n$-Y or (MAL-Fmoc)$_n$-Y wherein Y is a moiety of a drug, more preferably a peptide or protein drug, n is an integer of at least one, preferably 1 or 2, and Y is linked to the FMS or Fmoc radical through an amino group.

The present invention also provides a method for the preparation of a conjugate (PEG-Fmoc)$_n$-Y, wherein Y is a moiety of a drug, more preferably a peptide or protein drug, n is an integer of at least one, preferably 1 or 2, and Y is linked to the Fmoc radical through an amino group, which comprises:

(i) reacting a drug Y, e.g. a peptide or protein drug, with at least one equivalent of Precursor 7, thus obtaining a conjugate (MAL-Fmoc)$_n$-Y; and (ii) reacting the conjugate (MAL-Fmoc)$_n$-Y with PEG-SH.

In a most preferred embodiment, the invention relates to a method for preparation of a conjugate (PEG-FMS)$_n$-Y, wherein Y is a moiety of a drug, more preferably a peptide or protein drug, n is an integer of at least one, preferably 1 or 2, and Y is linked to the FMS radical through an amino group, which comprises:

(i) reacting a drug Y, e.g. a peptide or protein drug, with at least one equivalent of MAL-FMS-NHS, thus obtaining a conjugate (MAL-FMS)$_n$-Y; and (ii) reacting the conjugate (MAL-FMS)$_n$-Y with PEG-SH, thus obtaining the conjugate (PEG-FMS)$_n$-Y.

In another most preferred embodiment, the invention relates to a method for preparation of a conjugate (PEG-FMS)$_n$-Y, which comprises:

(i) reacting MAL-FMS-NHS with PEG-SH, thus obtaining a conjugate PEG-FMS-NHS; and (ii) reacting the drug Y, e.g. a peptide or protein drug, with at least one equivalent of the conjugate PEG-FMS-NHS, thus obtaining the conjugate (PEG-FMS)$_n$-Y.

The PEG-SH reagent is preferably PEG$_{40}$-SH, wherein the PEG moiety is a branched PEG moiety of molecular weight 40,000 Da.

As mentioned in the Background section herein, the pegylation technique has been extensively used for modifying molecules, in particular peptide and protein drugs, in an attempt to improve some of its characteristics such as improved stability and solubility, reduced immunogenicity, reduced proteolysis, reduced toxicity, reduced clearance by the kidneys, improved bioavailability, and extended circulating life thus less frequent dosing being required. However, one of the main problems of pegylation is that covalent bonding between the PEG moiety and the drug most often causes loss of biological activity or drastic decrease of pharmacological potency of the drug. For this reason, pegylation is used more for high-molecular weight proteins, that are less likely to be inactivated by the reaction with PEG, but is less frequent for peptides and low-molecular weight proteins.

Theoretically, decreased bioactivity of peptides and proteins by pegylation can be overcome by linking the PEG-chains via a chemical bond sensitive to mild alkaline and/or acid hydrolysis, or enzymatically cleavable by serum proteases or esterases. Obviously, an inconsistent rate of hydrolysis would render such an approach impractical. A prerequisite condition is therefore that the hydrolysis of the PEG-chains from the conjugate take place at a slow rate and in a homogenous fashion under the strictly homeostatic pH and temperature conditions of the mammalian circulatory system.

Previously, we have prepared 2-sulfo-9-fluorenyl-methoxycarbonyl-N-hydroxysuccinimide (FMS-OSu) (Gershonov et al., 1999, 2000; Shechter et al., 2001, 2001a) as a reversible protein modifier. Protein-linked FMS moieties undergo slow and spontaneous hydrolysis under physiological conditions generating the unmodified parent molecule. Hydrolysis of FMS-protein conjugates at 37° C. in normal human serum, in aqueous buffers of pH 8.5, or in the circulatory system in vivo, takes place with a t$_{1/2}$ of 5-7 hrs. Using the FMS moiety as the scaffold for the suggested reversible pegylation technology enables the hydrolysis rates of various PEG-FMS-protein conjugates to be predicted. The t$_{1/2}$ for the hydrolysis of modified small molecules and PEG-conjugated polypeptides and proteins falls within a relatively narrow range of 8-14 h. The constant hydrolysis rate for PEG-FMS-protein conjugates is due to the β-elimination reaction, which occurs at position 9 of the fluorenyl moiety, being solely dependent on the pH of the surrounding medium. Thus, in contrast to what occurs in approaches based on enzymatic hydrolytic bond cleavage, similar PEG-FMS hydrolysis rates are expected from all conjugates, regardless of the identity of the protein/peptide moiety conjugated. Using the present approach one can further control the hydrolysis rate by substitution of the fluorenyl moiety with electron-withdrawing or electron-inducing groups that increase or decrease, respectively, the hydrolysis rate. The number of PEG-FMS chains attached to the drug should also affect the rate at which the native drug is released.

The sulfonated fluorene moiety is not toxic, as previously shown (Shechter et al, 2001). High molecular-weight PEG is known to be safe in terms of toxicity and immunogenicity and is widely used in the food, cosmetic and pharmaceutical industries (Working et al., 1997; Roberts et al., 2002).

Thus, the present invention provides a procedure herein designated "reversible pegylation". In this new conceptual approach, that was implemented according to the invention with low molecular-weight polypeptides and proteins, the PEG moiety is not attached directly to the drug, as in the standard pegylation procedure, but rather the PEG moiety is attached directly or through a linker to a moiety of formula (i) to (iv) herein, and the drug is attached to another position of the moiety (i) to (iv). Said moiety (i) to (iv), preferably the Fmoc or FMS moiety (i), is highly sensitive to bases and is removable under mild basic conditions. Thus, in this way, a prodrug is obtained that is inactive, but undergoes transformation into the active drug under the physiological conditions of the body. The prodrug has an extended circulation life but the PEG moiety is removed together with the Fmoc or FMS moiety and the drug recovers its full pharmacological potency.

This novel approach enables the desirable pharmacological features associated with pegylation to be conferred on low molecular-weight peptide and protein drugs that would otherwise have been fully or partially inactivated by this technique. A pharmacologically 'silent' conjugate that is 'trapped' in the circulatory system releases the covalently-linked parent peptide or protein, with a desirable pharmacokinetic profile. This new approach is expected to extend the life-time, bioavailability and efficacy of existing peptide drugs, and to extend the same in known peptide drugs and peptide drug candidates that may yet be discovered.

This new technology has been successfully tested according to the invention on several peptide and protein drugs. In addition to prolonging life-times in vivo, the inactive but reactivatable PEG-protein conjugate has the profound advantage of maintaining a low circulating level of the active protein drug at any time point after administration. In this way, a well-known risk of the presence of a "burst" of toxifying or desensitizing drug in the circulation is avoided.

As mentioned above, in theory one can design PEG chains that can be released from PEG-protein conjugates by serum proteases or esterases. However, rapid or unpredictable rate of release is not useful. A prerequisite condition with this new technology is that the PEG-chains should be hydrolyzed spontaneously from the conjugates at a slow, continuous and predictable rate. Release of PEG-chains should occur over a prolonged period, thus maintaining the projected conjugates in the circulatory system, prior to removal of PEG-chains by hydrolysis. The present invention fulfills these requirements. For example, upon incubation in normal human serum at 37°

C., PEG-chains are hydrolyzed from proteins, with a half-time of 8.0±2 hrs. Rates of release are dictated exclusively by the nature of the Fmoc-moiety (Fmoc/FMS), by the pH and the reactivity of the blood serum, and mammals maintain strict homeostasis with regards to these last two parameters.

According to the present invention, a pilot experiment included synthesis of a pegylated insulin. Upon incubation of $(PEG_{5000}\text{-Fmoc})_1$-insulin derivative at pH 8.5, or at normal human serum at 37° C., the lipogenic activity was restored with a half-life of 30±2 hrs. Regeneration of the lipogenic potency of bis-modified insulin, $(PEG_{5000}\text{-Fmoc})_2$-insulin, followed an additional lag period of 10±1 hrs.

A single subcutaneous administration of $(PEG_{5000}\text{-Fmoc})_1$-insulin in mice, lowered circulating glucose levels and the half time of return to normoglycemic values exceeded 6.7 fold that for native insulin. Following intraperitoneal administration of $(PEG_{5000}\text{-Fmoc})_1$-insulin, the return to normoglycemia was 3.4 fold slower than after administration of the native hormone. In sum, a prototype of a reversible PEG has been established. It undergoes slow spontaneous hydrolysis after conjugation, regenerating the non-modified parent drugs, at physiological conditions. Thus, the principal drawback of inactivating drugs by pegylation is solved by the technology of the present invention. The PEG-FMS moieties hydrolyze at faster rates as compared to PEG-Fmoc-moieties ($t_{1/2}$=5-7 hrs, ref.). Compounds containing FMS-PEG moieties are more suitable when 2-5 PEG-chains are to be introduced into a peptide or a protein drug, for obtaining the desirable pharmacological features of the conjugates.

In another example of the present invention, it is shown herein that when native exendin-4 was subcutaneously administered at a dose of 4 µg/mouse, the blood glucose level (BGL) declined by 26-28% (from 140 mg/dl to 104-101 mg/dl), with the largest percent change in BGL occurring 0.5-1 h after administration. Glucose concentrations then returned to their initial levels with a $t_{1/2}$ of 3.7±0.3 h. Following the subcutaneous administration of $PEG_{40000}$-FMS-exendin-4, the decrease in BGL took place at a more moderate rate. Circulating glucose reached its lowest concentration 8-12 hours after administration (92 mg/dl, 33%). Stable, low circulating glucose concentrations were then maintained for a further 12 hours. Return to initial glucose levels took place with a $t_{1/2}$ of 30±2 h, being 7.5 times longer than that obtained by the same dose of the native exendin-4.

In a further example of the present invention, it is shown herein that using a BIAcore binding assay, the in vitro rate of regeneration of native interferon was estimated to have a half-life of 65 hrs. Following subcutaneous administration to rats and monitoring circulating antiviral potency, active IFNα2 levels peaked at 50 hrs, with substantial levels still being detected 200 hrs post administration. This value contrasts with a half-life of about 1 hr measured for unmodified interferon. The concentration of active IFNα2 scaled linearly with the quantity injected. Comparing subcutaneous to intravenous administration of $PEG_{40}$-FMS-IFNα2, we found that the long circulatory lifetime of IFNα2 was affected both by the slow rate of absorption of the pegylated protein from the subcutaneous volume and by the slow rate of discharge from the PEG in circulation. A numerical simulation of the results was in good agreement with the results observed in vivo. The pharmacokinetic profile of this novel pegylated IFNα2 conjugate combines a prolonged maintenance in vivo with the regeneration of active-native IFNα2, ensuring ready access to peripheral tissues and thus an overall advantage over currently used formulations.

Peptide $YY_{3-36}$ ($PYY_{3-36}$) was recently shown to induce satiety in mice and humans. It is described herein that the satiety induced by subcutaneous administration of $PYY_{3-36}$ to fasting mice had a half-life of ~3 h. Pegylation of $PYY_{3-36}$ through a non-hydrolysable bond yielded an inactive conjugate but the conjugate of the invention $PEG_{40}$-FMS-$PYY_{3-36}$ gradually released unmodified $PYY_{3-36}$ under physiological conditions. Subcutaneous administration of $PEG_{40}$-FMS-$PYY_{3-36}$ to mice resulted in protracted satiety, with a half-life of ~24 h. $PEG_{40}$-FMS-$PYY_{3-36}$ can therefore serve as a long-acting prodrug of $PYY_{3-36}$, thereby providing a more practical means for controlling human obesity.

The PEG moiety according to the invention may be linear or branched PEG and has a molecular weight in the range of 200 to 200,000 Da, preferably up to 80,000 Da, more preferably 5,000-40,000 Da, and most preferably between about 20,000 Da and 40,000 Da. Preferably, the PEG moiety is a branched PEG molecule of 40,000 Da.

The prodrugs of the present invention are prepared using PEGylating agents, meaning any PEG derivative which is capable of reacting with a functional group such as, but not limited to, $NH_2$, OH, SH, COOH, CHO, —N=C=O, —N=C=S, —$SO_2Cl$, —$SO_2CH=CH_2$, —$PO_2Cl$, —$(CH_2)_x$Hal, present at the fluorene ring of the Fmoc or FMS moiety. Examples of these reagents and of the products obtained are depicted in Scheme 7 herein. These derivatized PEGs that can be used according to the invention and similar reagents are commercially available. It should be noted that the PEGylating agent is usually used in its mono-methoxylated form where only one hydroxyl group at one terminus of the PEG molecule is available for conjugation. However, a bifunctional form of PEG where both termini are available for conjugation may be used if, for example, it is desired to obtain a conjugate with two peptide or protein residues covalently attached to a single PEG moiety.

In a preferred embodiment of the invention, the PEG moiety is branched. Branched PEGs are in common use. They can be represented as $R(PEG-OH)_m$ in which R represents a central core moiety such as pentaerythritol or glycerol, and m represents the number of branching arms. The number of branching arms (m) can range from three to a hundred or more. The hydroxyl groups are subject to chemical modification.

The use of branched PEG molecules has several advantages including the fact that they require substantially fewer conjugation sites and loss of bioactivity is minimized. Branched PEG molecules are described in U.S. Pat. No. 6,113,906, U.S. Pat. No. 5,919,455, U.S. Pat. No. 5,643,575, and U.S. Pat. No. 5,681,567, hereby incorporated by reference as if fully disclosed herein in their entirety.

The present invention further provides pharmaceutical compositions comprising a pegylated compound according to the invention or a pharmaceutically acceptable salt thereof, and a pharmaceutically acceptable carrier.

The carrier must be "acceptable" in the sense of being compatible with the active ingredient(s) of the formulation (and preferably, capable of stabilizing peptides) and not deleterious to the subject to be treated.

The formulations may conveniently be presented in unit dosage form and may be prepared by any of the methods well known in the art of pharmacy, for example as described in Remington: The Science and Practice of Pharmacy, A. R. Gennaro, ed., 20th edition, 2000. All methods include the step of bringing the active ingredient(s) into association with the carrier which constitutes one or more accessory ingredients.

Any suitable route of administration of the conjugates of the invention to humans or for veterinary purposes is envisaged by the invention, for example via conventional oral, intramuscular, intravenous, subcutaneous, intranasal and transdermal administration.

The invention further provides methods for treatment of diseases, disorders and conditions treatable by peptide and protein drugs which comprises the administration of a pegylated peptide or protein prodrug of the invention to an individual in need.

Thus, in one embodiment, there is provided a method for the treatment of diabetes mellitus or hyperglycemia which comprises administering to an individual in need an effective amount of a pegylated FMS conjugate of insulin of or a HSA-Fmoc-insulin conjugate of the invention.

In another embodiment, there is provided a method for the treatment of a viral disease which comprises administering to an individual in need an effective amount of a pegylated FMS conjugate of IFN-α2 of the invention. The viral disease is particularly hepatitis B or hepatitis C.

In a further embodiment, the invention relates to a method for the treatment of cancer such as bladder cancer, ovarian cancer, pancreatic cancer melanoma, non-Hodgkin's lymphoma, hairy cell leukemia, or AIDS-related Kaposi's sarcoma, which comprises administering to an individual in need an effective amount of a pegylated FMS conjugate of IFN-α2 of the invention.

In another embodiment, the invention relates to a method for reduction of food intake, treatment of obesity and diseases, conditions or disorders which can be alleviated by reduction of food intake including hypertension, dyslipidemia, cardiovascular risk, insulin-resistance, and diabetes mellitus which comprises administering to an individual in need an effective amount of a pegylated FMS conjugate of $PYY_{3-36}$ of the invention.

In another embodiment, there is provided a method for treatment of children of pathologically short stature which comprises administering to a child in need an effective amount of a pegylated FMS conjugate of hGH of the invention.

In a further embodiment, the invention relates to an anti-aging treatment which comprises administering to an individual in need an effective amount of a pegylated FMS conjugate of hGH of the invention.

In still another embodiment, the invention provides a method for treatment of a disease or disorder selected from the group consisting of cardiovascular diseases, congestive heart failure, hypertension, acute kidney failure and adult respiratory distress syndrome (ARDS), which comprises administering to an individual in need an effective amount of a pegylated FMS conjugate of ANP of the invention.

In yet another embodiment, the invention provides a method for treatment of insulin-dependent diabetes mellitus, non-insulin-dependent diabetes mellitus, or gestational diabetes mellitus, or for prevention of hyperglycemia which comprises administering to an individual in need an effective amount of a pegylated FMS conjugate of exendin of the invention.

The invention will now be illustrated by the following non-limiting Examples.

EXAMPLES

I. Chemical Section

Pegylation

Materials and Methods (Chemical Section)

(i) Materials: Human ($Zn^{2+}$-free) insulin was donated by Novo Nordisk (Bagsvaerd, Denmark) or by Biotechnology General (Rehovot, Israel), and was used without further purification. Recombinant hGH was a gift from Biotechnology General (Rehovot, Israel). Fmoc-Osu was obtained from Novabiochem (Laüfelfingen, Switzerland). $PEG_5$-OSu (also referred herein as $PEG_{5,000}$-OSu) and $PEG_{40}$-OSu (also referred herein as $PEG_{40,000}$-OSu) were from Shearwater (now Nektar Therapeutics, San Carlos, Calif., USA). TNBS, DTNB, α-lactalbumin, reduced glutathione (GSH), cystamine-2 HCl, dithiothreitol (DTT), iodoacetamide, gentamicin and TPCK-treated trypsin were purchased from Sigma Chemical Co. (St. Louis, Mo., USA). Non-glycosylated human IFN-α2 was prepared as described in WO 02/36067. Exendin-4, Peptide $YY_{3-36}$ and Peptide 27, a nonlysine-containing synthetic peptide of 27 amino acids (AEISGQL-SYVRDVNSWQHIWTNVSIEN) (SEQ ID NO: 14), used as control, were synthesized by the solid phase method using a multiple-peptide synthesizer (AMS 422, Abimed Analysen-Technik GmbH, Langenfeld, Germany). All other reagents, including a long list of compounds used for synthesizing MAL-FMS-NHS, were of analytical grade and purchased from Sigma Chemical Co. (St. Louis, Mo., USA).

(ii) Reverse-phase HPLC was performed with a Spectra-Physics SP8800 liquid chromatography system (Spectro-Physics, San Jose, Calif.) equipped with an Applied Biosystem 757 variable wavelength absorbance detector. The column effluents were monitored by UV absorbance at 220 nm and chromatograms were recorded on a chrom-Jet integrator (Thermo-Separation, Riviera Beach, Fla., USA). HPLC prepacked columns used in the examples included LiChroCART 250-10 mm containing LiChrosorb RP-18 (7 µm) and LiChrospher 100 RP-18 (5 µm) 250-4 mm (Merck, Rathway, N.J., USA) and pre-packed Vydac RP-18 or RP-4 columns (22×250 mm; 12 µm bead size; Vydac, Hesperia, Calif., USA). Linear gradients were used between solution A (0.1% TFA in $H_2O$) and solution B (0.1% TFA in acetonitrile-$H_2O$, 75:25). For analytical HPLC procedures, a linear gradient between 30 and 100% of solution B was run for 50 min at a flow rate of 0.8 ml/min.

(iii) HPLC analyses were performed using a Spectra-Physics SP8800 liquid chromatography system equipped with an Applied Biosystems 757 variable wavelength absorbance detector and a Spectra-SYSTEM P2000 liquid chromatography system equipped with a Spectra-SYSTEM AS100 autosampler and a Spectra-SYSTEM UV1000, all controlled by a ThermoQuest chromatograpy data system (ThermoQuest Inc., San Jose, Calif., USA). The column effluents were monitored by UV absorbance at 220 nm. Analytical RP-HPLC was performed using a prepacked Chromlith™ Performance RP-18e (4.6×100 mm, Merck KGaA, Darmstadt, Germany). The column was eluted with a binary gradient of 10-100% solution B over 10 min with a flow rate of 3 ml/min (solution A was 0.1% TFA in $H_2O$ and solution B was 0.1% TFA in acetonitrile:water, 3:1, v:v). Pegylated compounds were analyzed using a RP-4 column (250×4 mm, 5 µm bead size, VYDAC, Hesperia, Calif.) with a binary gradient of 10-100% solution B in 50 min at a flow rate of 1 ml/min.

(iv) Mass spectroscopy: Mass spectra (MS) were determined using matrix-assisted laser-desorption/ionizationtime-of-flight (MALDI-TOF) mass spectroscopy (Micromass UK Ltd.) and electrospray ionization mass spectra (ESMS) techniques (Bruker-Reflex-Reflectron model, Germany, and VG-platform-II electrospray single quadrupole mass spectrometer, Micromass UK Ltd., respectively). The polypeptides were deposited on a metal target as cocrystals with sinaptic acid, and the mass spectrum was determined in the positive ion mode.

(v) UV spectra: Ultraviolet spectra were obtained with a Beckman DU 7500 spectrophotometer in 1 cm path length UV cuvettes.

(vi) Thin-layer chromatography was performed on silica-gel plates, that were developed either with chloroform:methanol:acetic acid (9.2:0.5:0.3, v:v:v, TLC, A) or by chloroform:methanol (9:1, v:v, TLC, B).

(vii) Amino acid analyses were performed following 6N HCl acid hydrolysis at 110° C. for 24 h using a Dionex Automatic amino acid analyzer HP1090 (Palo Alto, Calif., USA). N-terminal sequence analyses were performed with a Model 491A Procise Protein sequencer (Applied Biosystems, Foster City, Calif., USA).

Identification of the intermediate compounds—Most of the chemical compounds used as reagents and intermediates in the Examples are identified by their formulas in the Schemes 1-7 hereinafter and the following characterization: the intermediates are identified by a bold underlined letter a to k (small cap) or by the term Precursor and a number in bold italics, i.e. Precursors 1-8.

Example 1

Synthesis of $PEG_{5,000}$-Fmoc-OSu (Precursor 1)

Precursor 1 of the formula depicted in Scheme 1 was prepared starting from 2-aminofluorene and t-Boc-alanine (BocAla) by several steps, as depicted in Scheme 2.

1(a). Synthesis of 2-(t-BocAla-amino)fluorene (Intermediate a)

t-Boc-Ala (4.16 gr, 22 mmol) was dissolved in 11 ml dioxane. N,N'-Dicyclohexylcarbodiimide (DCC) (11 mmol in 11 ml 1 M DMF) was then added and the reaction was carried out for 3 hours at 25° C. under stirring. Dicyclohexylurea (DCU) formed was removed by centrifugation. The symmetrical anhydride product thus obtained (t-Boc-Ala-anhydride) was reacted overnight under stirring with 2-aminofluorene (0.925 g, 11 mmol) in 30 ml dioxane-water (1:1, v:v) containing 11 mmol of $NaHCO_3$. The white solid formed was collected and dried under $P_2O_5$ in vacuum for 24 hours. Intermediate a was obtained in 60% yield (1.31 g, 3.34 mmol). It migrated on TLC (dichloromethane) with Rt=0.17. Mass-spectroscopy revealed a mass of 352.45 Da (calculated mass=352.2 Da).

1(b). Synthesis of 9-formyl-2-(t-BocAla-amino)fluorene (Intermediate b)

Intermediate a (1.31 g, 3.34 mmol) obtained in Example 1(a) was dissolved in 10 ml dry THF and combined with sodium hydride (NaH, 60%) (0.412 g, 11 mmol, 3.3 equivalents) suspended in dry THF. Ethyl formate (0.675 ml, 8.35 mmol) was then added and the reaction was carried out for 1 hour under stirring and argon atmosphere. After addition of ice chips and water, the organic solvent was removed by evaporation in vacuum. The aqueous solution was washed with ether and acidified to pH 5.0 with acetic acid. The precipitate formed was dissolved in ethyl acetate, the organic solution was washed several times with 0.5 M $NaHCO_3$, and dried over anhydrous sodium sulfate. The yellow solid formed after evaporation was triturated with ether and dried in vacuum. Intermediate b was obtained in 35% yield (0.46 g, 1.2 mmol). It migrated on TLC (chloroform:methanol:acetic acid, 9.2:0.5:0.3, v:v:v) with Rf=0.59. Mass-spectrum analysis (electrospray ionization technique) revealed a mass of 380.26 Da (calculated mass=380.2 Da).

1(c). Synthesis of 9-hydroxymethyl-2-(t-BocAla-amino) fluorene (Intermediate c)

Intermediate b (0.46 g, 1.2 mmol) obtained in Example 1(b) was suspended in dry methanol. Solid sodium borohydride ($NaBH_4$) (57 mg, 1.5 mmol) was added in several aliquots and the reaction mixture was stirred for 4 hours. The crude product obtained was further purified by flash chromatography on silica gel column and eluted with chloroform:methanol (95:5), to yield 80 mg (17%, 0.2 mmol) of pure Intermediate c that migrated on TLC (chloroform:methanol; 9:1, v:v) with Rf=0.53. Mass spectrum analysis revealed a mass of 382.2 Da (calculated mass=382 Da). $^1$H-NMR ($CD_3SOCD_3$) δ: 1.4 (S, 12H), 3.8-4.0 (m, 2H), 4.29 (d, 1H), 6.2 (s, broad), 7.2-7.3 (m, 2H), 7.6-8.0 (m, 4H), 8.4 (S, 1H).

1(d). Synthesis of 9-hydroxymethyl-2-(Ala-amino)fluorene (Intermediate d)

Intermediate c (80 mg, 0.2 mmol) obtained in Example 1(c) was dissolved in 5 ml of dichloromethane:trifluoroacetic acid (TFA) (1:1, v:v). After one hour, the solvents were removed by evaporation, and Intermediate d was suspended in ether, collected by precipitation and lyophilized.

1(e). Synthesis of Intermediate e

To a solution of Intermediate d (0.2 mmol) obtained in Example 1(d) and $NaHCO_3$ (0.8 mmol) in 3 ml $H_2O$, $PEG_{5,000}$-OSu (1 g, 0.2 mmol) was added. The reaction was carried out at 25° C., for several hours, with stirring. Product formation was verified by analytical HPLC procedure using C18 column (Rt=36.6 min). Mass spectrum analysis (MALDI) of Intermediate e revealed a mass of 5342 Da.

1(f). Synthesis of $PEG_{5,000}$-Fmoc-OSu (Precursor 1)

To a solution of the Intermediate e obtained in Example 1(e) (0.2 mmol) in 2 ml chloroform, triphosgene (1 mmol, 5 molar excess) in 3 ml cold chloroform was added portion-wise. Reaction was carried out overnight with stirring. The solvent was then evaporated and the residue was dissolved in 1.0 ml dry THF. N-hydroxysuccinimide (NHS) (100 mg, 4 equivalents) and 2,4,6-trimethylpyridine (0.163 ml, 6 equivalents) were added, and the reaction was carried out for 2 hours at room temperature with stirring. The title product, $PEG_{5,000}$-Fmoc-OSu, was purified to homogeneity by preparative HPLC procedure using a C18 column (HPLC, Rt=39.0 min). Mass spectrum analysis revealed a mass of 5654 kDa.

Unlike Fmoc-OSu, $PEG_{5,000}$-Fmoc-OSu is highly soluble in aqueous solutions, and absorbs in the UV region with a molar extinction coefficient of $\epsilon_{280}$=21,200 and $\epsilon_{301}$=10,100.

Example 2

Synthesis of $PEG_{5,000}$-FMS-OSu (Precursor 2)

Precursor 2, $PEG_{5,000}$-FMS-OSu, depicted in Scheme 1, was prepared by sulfonation of Precursor 1, $PEG_{5,000}$-Fmoc- OSu, with chlorosulfonic acid, as depicted in Scheme 2. Briefly, to a solution of Precursor 1 in 4.0 ml $CH_2Cl_2$, cooled to 0° C., a solution of $ClSO_3H$ in $CH_2Cl_2$ was added dropwise over a period of 15 min and the solution was stirred for 2 hours at 25° C. The product, $PEG_{5,000}$-FMS-OSu, sulfonated at position 2 of the fluorene ring, was purified by preparative HPLC-procedure, and characterized by mass spectroscopy, elementary analysis (for sulfur), following extensive dialysis, and for its rate of hydrolysis (at pH 8.5, 37° C.) following conjugation to either gentamicin or insulin.

Example 3

Synthesis of $PEG_{40000}$-Fmoc-OSu (Precursor 3)

Precursor 3, $PEG_{40000}$-Fmoc-OSu, depicted in Scheme 1, was prepared as described in Example 1, steps 1(e) and 1(f), but replacing $PEG_{5000}$-OSu with $PEG_{40000}$-OSu under the same reaction conditions.

Example 4

Synthesis of $PEG_{40000}$-FMS-OSu (Precursor 4)

Precursor 4, $PEG_{40000}$-FMS-OSu, depicted in Scheme 1, was prepared by sulfonation of Precursor 3, $PEG_{40000}$-Fmoc-OSu, as described in Example 2, but replacing Precursor 1 with Precursor 3 under the same reaction conditions.

Example 5

"One-Step" Procedure for Preparation of PEG-Fmoc/Drug Conjugates and PEG-FMS-Drug Conjugates For the preparation of PEG-Fmoc and PEG-FMS conjugates with drugs according to the invention, a "one-step" procedure can be used wherein a PEG-Fmoc-OSu or PEG-FMS-OSu precursor reacts with one or more amino groups of the drug in aqueous conditions.

Thus, in the following Examples 6-8, solid Precursor 1, $PEG_{5000}$-FMS-OSu, obtained in Example 1, was added at a 10-fold molar excess to stirred solutions of gentamicin or insulin (10 mg/ml) in phosphate-buffered saline (PBS) buffer, pH 7.4, at 0° C. Under these conditions, five to seven moles of Precursor 1 were incorporated per mole protein. The reaction was completed within 15 minutes after addition of the solid PEG-Fmoc-OSu.

Example 6

Synthesis of $(PEG_{5000}$-Fmoc$)_1$-Gentamicin

Solid Precursor 1 obtained in Example 1 (6 mg, 1 µmol) was added to a stirred solution of gentamicin (200 µmol in 1.0 ml 0.01 M $NaHCO_3$, pH ~7.5). The reaction was carried out for 3 hours at 25° C. and then dialyzed against $H_2O$ at 7° C. for several days. Under these dialyzing conditions, free gentamicin, that has not been covalently linked to PEG-Fmoc, was dialyzed out. The product, $PEG_{5000}$-Fmoc-gentamicin, contained one mol PEG-Fmoc covalently linked to one mol gentamicin as judged by its absorbance at 280 nm, and by amino acid analysis, following acid hydrolysis of a measured aliquot. The hydrolyzate contained alanine (derived from the PEG-ala-Fmoc moiety) and two peaks that emerged at the positions of proline and leucine, following acid hydrolysis of gentamicin (not shown).

Example 7

Synthesis of $(PEG_{5000}$-Fmoc$)_2$-Gentamicin

Solid Precursor 1 (11.3 mg, 2.1 µmol) was added to a stirred solution of gentamicin (0.5 mg, 1 µmol, in 1.0 ml 0.05 M $NaHCO_3$). The reaction was carried out for 2 hours at 25° C. and dialyzed overnight. The product, $(PEG_{5000}$-Fmoc$)_2$-gentamicin, contained about two moles PEG-Fmoc covalently linked to gentamicin, as verified by amino acid analysis following acid hydrolysis (see Example 6 above) and by determining the amount of non-modified amino groups with TNBS.

Example 8

Synthesis of $(PEG_{5000}$-Fmoc$)_1$-Insulin and $(PEG_{5000}$-Fmoc$)_2$-Insulin For the preparation of $(PEG_{5000}$-Fmoc$)_1$-insulin, to a stirred solution of $Zn^{2+}$-free insulin (1 mg in 2.0 ml 0.01 M $NaHCO_3$, 0.172 µmol), a fresh solution of Precursor 1 (8.8 µl, 20 mg/ml in DMF) was added (1.76 mg, 0.329 µmol, 1.9 molar excess of reagent over the protein). The reaction was carried out for 2 hours at 25° C. The reaction mixture was dialyzed overnight against $H_2O$, to remove $NaHCO_3$ and DMF. The title product contained about one mol PEG-Fmoc per mol insulin, as judged by several procedures described in the Biological Section hereinafter. The concentration of insulin in the sample was routinely determined by acid hydrolysis of a 20 µl aliquot, followed by amino acid analysis, and was calculated according to glutamic acid (7 residues), aspartic acid (3 residues) and isoleucine (2 residues).

The preparation of $(PEG_{5000}$-Fmoc$)_2$-insulin was carried out as described above while using 4.63 mg, 0.865 µmol, 5 molar excess of reagent over the protein.

Example 9

Synthesis of N-[2-(3-acetylthiopropionylamino)-9-fluorenyl-methoxycarbonyloxy]-succinimide (Precursor 5)

Precursor 5, depicted in Scheme 3, was synthesized starting from 2-aminofluorene by the procedure depicted in Scheme 4, as follows:

9(a). Synthesis of 2-(t-Boc-amino)fluorene (Intermediate f)

Di-t-butyl-dicarbonate (Boc anhydride, 14 g, 64.2 mmol) solution in dioxane (50 ml) was combined with 2-aminofluorene (10 g, 55 mmol in 100 ml dioxane:water, 1:1, v:v) and with $NaHCO_3$ (9.24 g, 110 mmol), and stirred overnight. The white solid thus formed was filtered, washed with ice water (200 ml) and dried under high vacuum. Intermediate f was obtained in 60% yield (9.24 g, 33 mmol. TLC (chloroform: methanol:acetic acid, 9.5:0.5:0.3, v:v:v); Rf=0.73. Calculated ESMS=280.4 Da. found ESMS=280.45 Da.

9(b). Synthesis of 9-formyl-2-(t-Boc-amino)fluorene (Intermediate g)

Intermediate f (3 g, 10 mmol), obtained in step 9(a), was dissolved in dry THF (30 ml) and added to a suspension of sodium hydride (NaH) (60%, 1.23 g, 33 mmol, 3.3 eq) in dry THF under Argon atmosphere. Ethyl formate (2 ml, 25 mmol, 2.5 eq) was then added and the reaction mixture was stirred for 1 hour. Ice chips and water were added, the organic solvent was evaporated, and the aqueous solution was washed with ether and acidified with acetic acid (pH ~5). The precipitate thus formed was dissolved in ethyl acetate, washed with NaHCO$_3$ (0.5N), brine and dried over anhydrous sodium sulfate. The yellow solid was washed with ether and dried. Intermediate g was obtained in 90% yield (2.8 g, 9 mmol). TLC (chloroform:methanol:acetic acid; 9.5:0.5:0.3, v:v:v), Rf=0.66. Calculated ESMS=309 Da. found ESMS=309.2 Da. M−1: 308.20, M+Na: 332.36, dimer [M+Na]$^+$: 641.59.

9(c) Synthesis of 9-hydroxymethyl-2-(t-Boc-amino) fluorene (Intermediate h)

Sodium borohydride (NaBH$_4$) (0.38 g, 10 mmol) was added portionwise to a suspension of Intermediate g (2.8 g, 9 mmol) obtained in step 9(b), in dry methanol, and the reaction allowed to proceed for 4 hours. The product, Intermediate h was purified by flash chromatography on silica gel column, that was eluted with chloroform:methanol (98:2, v:v), and was obtained in 50% yield (1.4 g, 4.5 mmol). TLC (chloroform:methanol, 9:1, v:v), Rf=0.54; Calculated ESMS=311 Da. found ESMS=311.42 Da, for [M+Na]$^+$=334.42, for [M+K]$^+$=350.34.

9(d). Synthesis of 9-hydroxymethyl-2-aminofluorene (Intermediate i)

Intermediate h (1.4 g, 4.5 mmol) obtained in step 9(c) was dissolved in 110 ml 5N HCl in dioxane. After 1 hour, the solvent was concentrated by evaporation and the product was precipitated with ether and lyophilized. Intermediate i was obtained in 84%, yield (0.79 g, 3.78 mmol). TLC (chloroform:methanol, 9:1, v:v), Rf=0.38; calculated ESMS=211.26 Da. found ESMS for [M+H]$^+$=211.10 Da.

9(e). Synthesis of 3-S-Acetylthiopropionic Acid

Pyridine (6.9 ml, 84.6 mmol) was added to a mixture of 3-mercaptopropionic acid (2.5 ml, 28.2 mmol) and acetic anhydride (16 ml, 84.6 mmol). The reaction solution was stirred for 16 h and concentrated by vacuum. Water (5 ml) was added for 20 min and the solution was concentrated by vacuum. The obtained oil was dissolved in ether (50 ml) and washed with water and KHSO$_4$ (0.5N). The ether fraction was dried with Na$_2$SO$_4$ and vacuum to produce the title product (Yield: 85%, 24 mmol, 3.6 g). $^1$H-NMR (CDCl$_3$) δ: 2.21 (s, 3H), 2.6 (t, 2H), 2.9 (t, 2H).

9W. Synthesis of 3-S-Acetylthiopropionic Anhydride

3-S-acetylthiopropionic acid of step 9(e) (1.8 g, 12 mmol) and DCC (1.4 g, 6 mmol) were dissolved in DMF (15 ml) for 4 hours. The precipitated DCU was filtered out and the anhydride thus formed was kept at 4° C. until used.

9(g). Synthesis of 9-hydroxymethyl-2-(3-acetylthiopropionyl-amino)-fluorene (Intermediate j)

Intermediate i (0.422 g, 2 mmol) obtained in step 9(d) and NaHCO$_3$ (0.74 g, 18 mmol) were dissolved in water/dioxane (1:1, 20 ml) and 3-S-acetylthiopropionic anhydride of step 9(f) in DMF (17 ml, 6 mmol) was added. The reaction solution was stirred for 1 hour. The organic solvents were removed by vacuum and the liquid solution was extracted with ether, washed with Na$_2$SO$_4$ (0.5N) and water and dried by vacuum. The obtained crude product, Intermediate j, was further purified by flash chromatography on silica gel column and elution with ethyl acetate:hexane (1:1, v:v). Yield: 60%, 0.4 g, 1.2 mmol. ESMS, (ca. 431) M+Na$^+$: 464, dimer 2M: 682, dimer 2M: Na$^+$: 705.67. $^1$H-NMR (CDCl$_3$) δ: HPLC (Chromolith column) 5.3 min (10-100% solution B in 10 min, 3 ml/min).

9(h). Synthesis of Precursor 5

Intermediate j obtained in step 9(g) was reacted with N-hydroxysuccinimide and phosgene, as depicted in Scheme 4. Thus, pyridine (0.215 ml, 2.7 mmol) was added dropwise to a stirred solution of Intermediate j (0.385 g, 0.9 mmol) and triphosgene (0.265 g, 0.9 mmol, 3 eq) in dry THF (5 ml). After 20 min, the precipitated pyridine hydrochloride salt was filtered out and the THF was removed by evaporation. The obtained oil was dissolved in dry THF (10 ml). N-hydroxysuccinimide (0.5 g, 4.4 mmol, 5 eq) and pyridine (0.215 ml, 2.7 mmol) were then added and the solution stirred for 20 min. The precipitated pyridine hydrochloride salt was filtered out and the THF was removed by vacuum. The obtained oil was further purified by flash chromatography on silica gel column and elution with ethyl acetate:hexane (1:1 and 4:1). The product, Precursor 5, was obtained in a yield of 88% (0.38 g, 0.78 mmol). ESMS: (ca 482) M: 482.2. HPLC (Chromolith column) 6.68 min (10-100% solution B in 10 min, 3 ml/min). TLC (ethyl acetate:hexane, 1:1, v:v) Rf=0.4.

Example 10

Synthesis of N-[2-(3-acetylthiopropionylamino)-7-sulfo-9-fluorenylmethoxycarbonyloxy]-succinimide (Precursor 6)

Precursor 6, depicted in Scheme 3, was prepared by sulfonation of Precursor 5 with chlorosulfonic acid as described above in Example 2.

Example 11

Synthesis of MAL-Fmoc-NHS, N-[2-(maleimidopropionyl-amino)fluoren-9-yl-methoxycarbonyloxy] succinimide) (Precursor 7)

Precursor 7, MAL-Fmoc-NHS depicted in Scheme 3, was prepared as depicted in Scheme 5 starting from 2-aminofluorene through the synthesis of the Intermediates f to i, described in Example 9 above, followed by the steps below:

11(a). Synthesis of 9-Hydroxymethyl-2-(maleimidopropionyl-amino)fluorene (Intermediate k)

3-Maleimidopropionic anhydride was prepared by dissolving 3-maleimido-propionic acid (1 g, 5.9 mmol) and DCC (0.69 g, 2.95 mmol) in 10 ml DMF and incubating for 4 h. DCU was filtered out and the anhydride thus formed was kept at 4° C.

9-Hydroxymethyl-2-amino-fluorene (Intermediate i; (0.4 g, 1.9 mmol) and NaHCO$_3$ (0.74 g, 8.85 mmol) were dissolved in water and 3-maleimidopropionic anhydride in DMF (12 ml, 2.95 mmol) was added. The reaction mixture was stirred for 40 min and product formation monitored by analytical HPLC on a Chromolith column (Rt=4.46 min, 10-100% B in 10 min, 3 ml/min). The crude product, Intermediate k, was purified using preparative HPLC (RP-18 column, 10-100% acetonitril:water [75:25; v:v], 60 min, 12 ml/min). Yield: 57%, 1.08 mmol, 0.39 g. Calculated ESMS=362.38 Da. found ESMS=362.42 Da).

11(b). Synthesis of MAL-FMOC-NHS

Pyridine (0.167 ml, 2 mmol) was added dropwise to a stirred solution of Intermediate k (0.37 g, 1.02 mmol) obtained in step 11(a) and triphosgene (0.425 g, 1.43 mmol, 4.2 eq) in dry THF (10 ml). After 20 min the precipitated pyridine hydrochloride salt was filtered out and the THF removed by vacuum. The oil obtained was dissolved in 10 ml dry THF with N-hydroxysuccinimide (0.61 g, 5.3 mmol). Pyridine (0.26 ml, 3.2 mmol) was then added and the solution was stirred for 20 min. Some additional precipitated pyridine hydrochloride salt was filtered out and the THF removed by vacuum. The oil obtained was dissolved in chloroform (100 ml) and washed with an aqueous $NaHCO_3$ solution (0.5N, 3×50 ml), HCl (0.1N, 3×50 ml), water (2×50 ml) and brine. The chloroform was removed by vacuum and the product, Precursor 7, was desiccated. Yield: 89% (0.9 mmol, 0.45 g). HPLC (Chromolith column) Rt=5.7 min (10-100% B in 10 min, 3 ml/min). Calculated ESMS=503 Da. found ESMS for $[M+Na]^+$=526.38 Da. found ESMS for $[M+K]^+$=542.30 Da.

Example 12

Synthesis of MAL-FMS-NHS, N-[2-(maleimidopropionylamino)-7-sulfo-fluoren-9-yl]methoxycarbonyloxysuccinimide (Precursor 8)

Precursor 8, depicted in Scheme 3, herein also identified by the abbreviation MAL-FMS-NHS (or MAL-FMS-OSu), was prepared by sulfonation of Precursor 7, MAL-Fmoc-NHS, with chlorosulfonic acid as depicted in Scheme 5, as follows:

To a solution of Precursor 7 (0.2 mmol, 0.1 g) obtained in Example 11 in trifluoroacetic acid (TFA) (10 ml), chlorosulfonic acid (0.5 ml) was added. After 15 minutes, cold ether (90 ml) was added and the precipitated product. Precursor 8, was washed with ether (×3) and desiccated. Yield: 95% (0.11 g, 0.19 mmol). HPLC (Chromolith column) Rt=2.65 min (10-100% B in 10 min, 3 ml/min). Calculated ESMS=583 Da. found ESMS for $[M-H]^+$=582.24 Da, for $[M+H]^+$=584.52 Da, and for $[M+Na]^+$=606.47 Da.

Example 13

Chemical Characterization of MAL-FMS-NHS

MAL-FMS-NHS or MAL-FMS-OSu is a water-soluble, hetero-bifunctional reagent consisting of a sulfonated fluorenylmethoxycarbonyl N-hydroxy-succinimide ester that reacts with peptide and protein amino groups. A maleimide group was attached to the fluorenyl backbone to enable coupling to sulfhydryl-containing $PEG_{40000}$-SH.

MAL-FMS-NHS is a cleavable reagent capable of reacting covalently with the amino side chains of peptides, proteins and aminoglycosides. According to the present invention, it enables PEG chains to be linked to peptides and proteins through a slowly hydrolysable chemical bond. PEG-FMS-peptide/protein conjugates thus formed undergo spontaneous hydrolysis at a slow rate upon incubation at ph 8.5, 37° C., with a $t_{1/2}$ value of 8-14±2 h, generating the unmodified parent molecule.

Chemical features of MAL-FMS-NHS. Table 1 summarizes several of the characteristic features of MAL-FMS-NHS. It is a water- and DMF-soluble compound. Mass spectrum analysis has yielded a calculated mass of 583 Da. The compound absorbs in the U.V. region with a molar extinction coefficient $\epsilon_{280}$=21,000±200 $mol^{-1}$ $cm^{-1}$. The curve shows a maximum at 290 nm, and a shoulder extending up to 330 nm. At 320 nm, where peptides or proteins absorb negligibly, MAL-FMS-NHS, either free or covalently bound to proteins, absorbs with a molar extinction coefficient $\epsilon_{320}$=16,100±150 $mol^{-1}$ $cm^{-1}$ (Table 1).

Stability of the MAL Functional Moiety in Aqueous Solutions.

Figure 1:
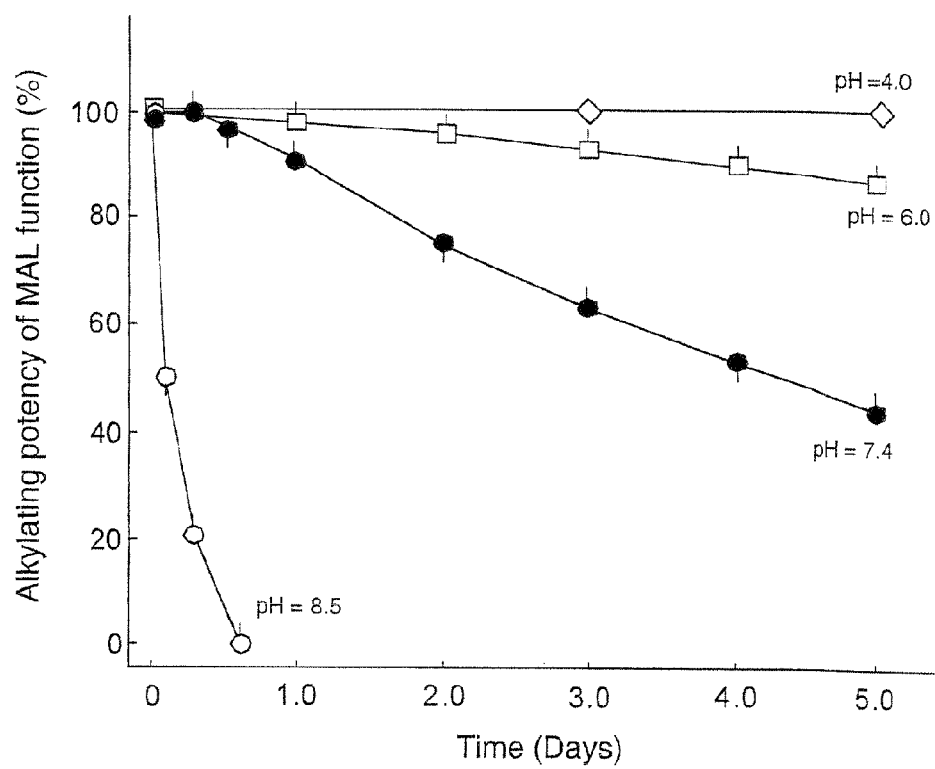
FIG. 1 shows the stability of the maleimide functional moiety in MAL-FMS-NHS in aqueous solutions having different pH values. MAL-FMS-NHS (1 mM) was incubated at room temperature in H$_2$O (pH 6.0), in 0.007 M acetic acid (pH~4.0), in 0.1 M phosphate buffer (pH 7.4), and in 0.1 M NaHCO$_3$ (pH 8.5). At the indicated time points, aliquots were allowed to react with a slight excess of GSH (15 min at pH 7.2) and the concentration of unreacted GSH was determined with 5,5-dithiobis(2-nitrobenzoic acid) (DTNB).

In order to test the stability of the maleimide function of MAL-FMS-NHS in aqueous solutions at different pH values, MAL-FMS-NHS (1 mM) was incubated at room temperature in water (pH 6.0), in 0.007M acetic acid (pH ~4.0), in 0.1M phosphate buffer (pH 7.4), and in 0.1M $NaHCO_3$ (pH 8.5). At several time points, aliquots were allowed to react with a slight excess of reduced glutathione (GSH) (15 min at pH 7.2) and the concentration of unreacted GSH was determined with DTNB (5,5'-dithio-bis-2-nitrobenzoic acid, Ellman's reagent), by measuring the absorbance of the produced yellow colored 5-thio-2-nitrobenzoic acid (TNB) at 405 or 412 nm. FIG. 1 demonstrates the potency of the reaction of MAL-FMS-NHS with GSH as a function of time, at different pH values. MAL-FMS-NHS was found fully stable at pH 4 to 6 over a period of a day or two and at pH 7.2 it is stable over a period of several hours. At pH 8.5, the maleimide moiety was destroyed at an accelerated rate ($t_{1/2}$ value=2.7±0.3 hr, FIG. 1).

Example 14

Figure 2:
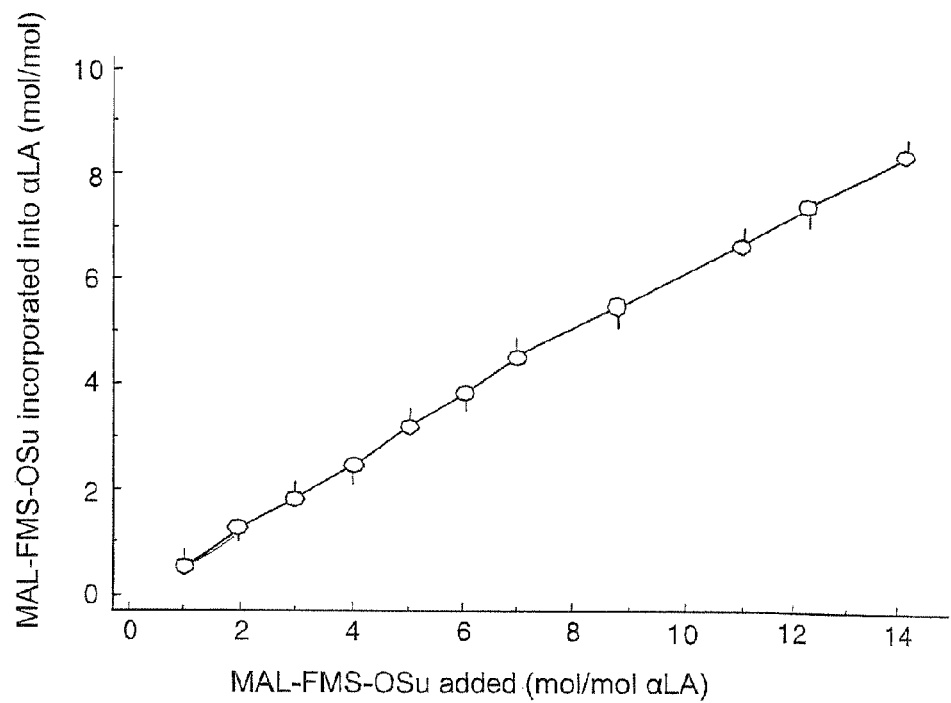
FIG. 2 shows the degree of incorporation of MAL-FMS-NHS at pH 7.2 into α-lactalbumin (α-LA) as a function of the amount of added reagent. To samples of α-LA (1.0 ml of 1 mg/ml in 0.1M phosphate buffer, pH 7.2), MAL-FMS-NHS was added at concentrations ranging from 1 equivalent up to 14 molar equivalents of MAL-FMS-NHS. For each treatment the amount incorporated into the protein was determined by the absorbance at 280 nm, after dialysis, and by quantitating the amount of unmodified amino-side chain moieties with trinitrobenzene sulfonic acid. (TNBS).

Degree of Incorporation of MAL-FMS-NHS at pH 7.2 into α-Lactalbumin as a Function of the Amount of Added Reagent To evaluate the degree of incorporation of the maleimide moiety into peptides/proteins as a function of the reagent, α-lactalbumin was used as a model. Thus, to samples of α-lactalbumin (α-LA, 1.0 ml of 1 mg/ml), MAL-FMS-NHS was added in 0.1M PBS, pH 7.2, at concentrations ranging from 1 equivalent up to 14 molar equivalents of MAL-FMS-NHS, for 30 min at 25° C., that is, under experimental conditions where the maleimide-alkylating capacity of the spacer remains unmodified. For each treatment, the amount incorporated into the protein was determined by UV absorbance at 280 nm, after dialysis, and by quantitating the amount of unmodified amino side-chain moieties with TNBS. As shown in FIG. 2, about one mole of MAL-FMS was incorporated into α-LA per 2.1 mole of reagent added, up to a fourteen molar excess over the protein.

Example 15

Synthesis of $PEG_{40}$-SH $PEG_{40}$-SH was prepared either by reaction of 2-tritylthioethylamine and $PEG_{40}$-OSu as described below in 15(a), or from $PEG_{40}$-OSu and cystamine[2,2'-dithio-bis(ethylamine)]dihydrochloride, as described below in 15 (b).

15(a). Synthesis of $PEG_{40}$-SH from 2-tritylthioethylamine and $PEG_{40}$-OSu Synthesis of 2-Tritylthioethylamine.

2-Amino-ethanethiol (3 g, 26.5 mmol) and triphenylmethyl alcohol (7 g, 26.9 mmol) were dissolved in TFA (20 ml) and stirred for 30 min at room temperature. The TFA was removed by evaporation and the remaining oil residue was dissolved in ether (400 ml) and stored at −20° C. The product isolated was washed with cooled ether and water. A concentrated ammonia solution (25%, 30 ml) was then added, and the aqueous phase was washed several times with ether. The ether was removed by vacuum and the product was desiccated. Yield, 78% (6.6 g, 20.7 mmol), Rt=5.35 min.

2-Tritylthioethylamine and $PEG_{40}$-OSu (0.25 g, 6.25 µmol) were dissolved in 4 ml THF:acetonitrile (1:2, v:v). After one hour, the product was precipitated with cooled ether and washed (×3). The dry pellet was dissolved in TFA:triethylsilane:water (95:2.5:2.5, 6 ml) and, after one hour, $PEG_{40}$-SH was precipitated by cooled ether (100 ml) and desiccated.

15(b). Synthesis of $PEG_{40}$-SH from Cystamine and $PEG_{40}$-OSu $PEG_{40}$-OSu was dissolved at a concentration of 40 mg/ml in an aqueous solution of cystamine-di-HCl (1M) and brought to pH 8.5 with $NaHCO_3$. Reaction was carried out for 2 h at 25° C. The product thus obtained was dialyzed overnight against 0.1 M $NaHCO_3$, treated with 30 mM dithiothreitol (25° C., 1 h) and re-dialyzed against 0.01 M HCl containing 10 mM ascorbic acid. $PEG_{40}$-SH was obtained with a 93% yield. It contained 1 mole sulfhydryl moiety per mole $PEG_{40}$, as determined with DTNB in the presence of ascorbate. $PEG_{40}$-SH was kept frozen until used.

Example 16

Preparation of PEG-FMS-Drug Conjugates from MAL-FMS-NHS (Procedure I)

For the preparation of PEG-FMS-drug conjugates according to the invention, a "two-step" Procedure I can be used as depicted in Scheme 6 whereby MAL-FMS-NHS is first reacted with an amino-containing drug or with the amino group of a peptide or protein drug and the resulting MAL-FMS-drug conjugate is further reacted with PEG-SH. as follows:

16(a). Preparation of MAL-FMS-Drug Conjugates

In the first step, a MAL-FMS-drug conjugate is prepared by adding one to seven molar excess of MAL-FMS-NHS, Precursor 8, to a stirred solution of the drug (1 mg/ml) in 0.1 M PBS buffer, pH 7.2. The reaction is carried out for 30 min at 25° C., and then dialyzed against water at 7° C. over a period of 24 h to remove excess MAL-FMS-NHS. The amount of FMS-MAL residues incorporated into the drug, e.g. a peptide or protein drug, is determined both by the absorption at 320 nm using molar extinction coefficient of $\epsilon_{320}$=16,100, and by quantitating the incorporated MAL function into the drug. This is performed by adding a measured aliquot into a GSH solution (0.1 mM in phosphate buffer, pH 7.2). The concentration of unreacted GSH remained is determined with DTNB.

16(b). Preparation of PEG-FMS-drug Conjugates

In the second step, a stoichiometric amount of solid $PEG_{40}$-SH is added to the MAL-FMS-drug conjugate of step 16(a), and the reaction proceeds for additional 60 min in 0.1 M phosphate buffer, pH 7.2, containing 2 mM ascorbic acid. The PEG-FMS-drug conjugate thus obtained is further purified by HPLC-procedures using C4 or C18 reverse phase columns under conditions resolving the conjugate from the drug, preferably a peptide or protein drug (or protein-FMS-MAL) that has not been covalently linked to $PEG_{40}$-SH.

Example 17

Preparation of PEG-FMS-Drug Conjugates from MAL-FMS-NHS (Procedure II)

PEG-FMS-drug conjugates according to the invention may be also prepared by an alternative "two-step" Procedure II depicted in Scheme 6 whereby MAL-FMS-NHS is first reacted with PEG-SH and the resulting PEG-FMS-NHS conjugate is further reacted with an amino-containing drug or with the amino group of a peptide or protein drug. as follows:

17(a). Preparation of PEG-FMS-NHS Conjugate

In the first step, a PEG-FMS-NHS conjugate is prepared by MAL-FMS-NHS to a stirred solution of PEG-SH in PBS buffer, pH 7.4. The reaction is carried out for 30 min at 25° C. and the product is then purified by HPLC and lyophilized.

17(b). Preparation of PEG-FMS-Drug Conjugates

In the second step, a stoichiometric amount of the MAL-FMS-NHS conjugate of step 17(a) is added to the amino-containing drug, and the reaction proceeds under stirring for 2 hours. The product is then purified by HPLC and lyophilized.

Example 18

Synthesis of $(PEG_{40}\text{-FMS})_1$-Insulin $(PEG_{40}\text{-FMS})_1$-insulin, was prepared by the two-step Procedure I described in Example 16. Thus, Mal-FMS-NHS (6 g, 10 µmol) was dissolved in water (0.25 ml) and added to an insulin ($Zn^{2+}$-free, 25 mg, 4.16 µmol) solution in PBS (0.5 ml, pH=7.4). The pH was adjusted to 7-8 with $NaHCO_3$. The reaction was stopped after 30 min with diluted hydrochloric solution (pH=6). The product was isolated using preparative HPLC (C18 column, 10-80% acetonitrile:water, 75:25, v:v, 50 min, 10 ml/min) and identified as monosubstituted insulin derivative Mal-FMS-insulin using electrospray mass spectrometry (ESMS (ca. 6280), M−1: 6278.83, M+1: 6280.73). Analytical HPLC (Chromolith column), Rt=4.58 min.

$PEG_{40}$-SH (20 mg, 0.5 µmol) was added to a solution of the Mal-FMS-insulin intermediate (2 mg, 0.317 µmol) in PBS (0.3 ml, pH=7.4), the pH was adjusted to 7-8 with $NaHCO_3$ and the reaction was stopped after 30 min with diluted hydrochloric solution (pH=6). The title product, $PEG_{40}$-FMS-insulin, was subjected to analytical HPLC (Chromolith column), Rt=6.6 min.

Example 19

Synthesis of $PEG_{40}$-FMS-Exendin-4

$PEG_{40}$-FMS-exendin-4 was prepared by the two-step Procedure I described in Example 16. Thus, 280 µg of MAL-FMS-NHS (28 µl from a fresh solution of MAL-FMS-NHS in DMF, 10 mg/ml, 2.0 molar excess over the peptide) was added to a stirred solution of exendin-4 (1 mg in 1.0 ml 0.1 M phosphate buffer, 2 mM ascorbate, pH 7.2, 0.239 mM). After 7 min, solid $PEG_{40000}$-SH was added to a final concentration of 0.5 mM (2.1 molar excess over the peptide). The reaction was carried out for 1 h hour, dialyzed overnight against water and then further filtered through Centricon with a molecular weight cutoff of 50 kDa to remove any residual exendin-4 or MAL-FMS-exendin-4 that had not linked to PEG$_{40000}$-SH. The concentration of the conjugate was determined by acid hydrolysis of a 20 µl aliquot followed by amino acid analysis, according to aspartic acid (2 residues), alanine (2 residues) and valine (1 residue), and absorbance at 280 nm was monitored. The calculated extinction coefficient at 280 nm is 26940±100, a value that is the additive absorbance of exendin-4 ($\epsilon_{280}$=5740) and PEG$_{40000}$-FMS ($\epsilon_{280}$=21200). A solution of 20 µM PEG$_{40000}$-FMS-exendin had OD$_{280}$=0.51. Thus the conjugate had a 1:1 PEG$_{40000}$-FMS/exendin stoichiometry (as determined from the UV absorption of the conjugate following purification and acid hydrolysis followed by amino acid analysis as described above).

Example 20

Synthesis of PEG$_{5000}$-FMS-Exendin-4

PEG$_{5000}$-FMS-exendin-4 was prepared by the two-step Procedure II described in Example 17. Thus, MAL-FMS-MHS (1.8 mg, 3 µmol) was added to a solution of PEG$_{5000}$-SH (15 mg, ~3 µmol) in PBS (0.5 ml, pH=7.4) and the reaction solution was stirred for 30 min. The product PEG$_{5000}$-FMS-NHS was purified by HPLC on a RP-4 column and lyophilized.

PEG$_{5000}$-FMS-NHS (2.3 mg, ~0.42 µmol) was then added to a solution of exendin-4 (1.6 mg, 0.4 µmol) in PBS (0.5 ml, pH=8) and the reaction solution was stirred for 2 h. The product PEG$_{5000}$-FMS-exendin-4 was purified by HPLC on a RP-4 column and lyophilized.

Example 21

Synthesis and Characterization of PEG$_{40}$-FMS-IFNα2

The attachment of a single PEG-chain of 40 kDa to IFNα2 appears sufficient to grossly arrest kidney filtration of the conjugate (Bailon et al., 2001). We therefore envisioned that the linkage of a single PEG$_{40}$-FMS chain to IFNα2 would suffice to obtain a prolonged-acting conjugate that releases IFNα2, with a desirable pharmacokinetic profile. In the procedure found most optimal for introducing one mole PEG$_{40}$-FMS/mol protein, IFNα2 was allowed to react first with 3 equivalents of MAL-FMS-NHS, at pH 7.2, for 7 min, followed by the addition of 3 equivalents of PEG$_{40}$-SH, at pH 7.2, for 1 hour. The NHS function of MAL-FMS-NHS is relatively unstable at prolonged aqueous neutral conditions, whereas the MAL function of the spacer preserves its alkylating capacity for several hours at pH 7.2 (not shown). We therefore preferred to use Procedure I of Example 16 and to react MAL-FMS-NHS first with IFNα2 and to subsequently link PEG$_{40}$-SH to the IFNα2-FMS-MAL conjugate.

To a stirred solution of IFNα2 (1 mg/1.0 ml) in phosphate buffer, pH 7.2 (52 µM), 91 µg of MAL-FMS-NHS was added (9.1 µl from a fresh solution of MAL-FMS-NHS, (10 mg/ml) in DMF, (3.0 molar excess over the protein). After 7 min, PEG$_{40}$-SH was added to obtain a final concentration of 156 µM (three molar excess over the protein). The reaction was carried out for 1 h, and then dialyzed overnight against H$_2$O to remove residual DMF and phosphate buffer. The conjugate thus obtained was characterized by MALDI-TOF as PEG$_{40}$-FMS-IFN-α2.

Table 2 summarizes several characteristic features of the conjugate thus obtained. MALDI-TOF mass spectra analysis shows a 1:1 PEG$_{40}$-FMS/IFNα2 stoichiometry. The experimental mass obtained, 63540 Da, corresponds to the additive masses found for PEG$_{40}$-SH (43818 Da), IFNα2 (19278 Da) and of the spacer molecule following conjugation (473 Da). PEG$_{40}$-FMS-IFNα2 migrates on analytical HPLC as a wide peak with Rt value=43 min. The conjugate is highly soluble in aqueous solutions. It has a molar extinction coefficient $\epsilon_{280}$=39270±100, corresponding to the absorption of the native cytokine and of FMS ($\epsilon_{280}$=21,200) (Gershonov et al., 2000).

Example 22

Synthesis of (PEG$_{40}$-FMS)$_2$-IFNα2

(PEG$_{40}$-FMS)$_2$—IFNα2 was prepared as described in Example 21 above for PEG$_{40}$-FMS-INFα2, but using 6 eq (16 µg, 44.5 nmol, in 10 µl DMF) of MAL-FMS-NHS.

Example 23

Synthesis of PEG$_{40}$-FMS-PYY$_{3-36}$

In the procedure found most optimal for coupling about one mole of PEG$_{40}$-SH per mol of MAL-FMS-PYY$_{3-36}$, PYY$_{3-36}$ was allowed to react first with 2 equivalents of MAL-FMS-NHS, at pH 7.2, for 7 min, followed by the addition of 2.1 equivalents of PEG$_{40}$-SH, at pH 7.2, for 1 hour.

To a stirred solution of PYY$_{3-36}$ (1 mg in 1.0 ml phosphate buffer, pH 7.2, 10 mM Na ascorbate (0.247 µM), 288 µg of MAL-FMS-NHS was added (28.8 µl, from a fresh 10 mg/ml solution of MAL-FMS-NHS in DMF; twofold molar excess over the peptide). After 7 min, PEG$_{40}$-SH was added to obtain a final concentration of 0.52 mM (2.1 molar excess over the peptide). The reaction was carried out for 1 h and the mixture was then dialyzed overnight against water. The resulting PEG$_{40}$-FMS-PYY$_{3-36}$ was characterized by MALDI-TOF MS.

Example 24

Synthesis of (PEG$_{40}$-FMS)$_2$-hGH (PEG$_{40}$-FMS)$_2$-hGH was prepared by the two-step procedure described in Example 16, as follows: To a stirred solution of human growth hormone (4.4 mg, 0.22 µmol) in phosphate buffer (1 ml, 0.1 M, pH 7.2), MAL-FMS-NHS (4 eq, 0.47 mg, 0.8 µmol) was added. The reaction was carried out for 30 min at 25° C., and then dialyzed against H$_2$O (pH 6) at 4° C. for 24 h, to remove excess MAL-FMS-NHS. Solid PEG$_{40}$-SH (7 eq, 65 mg, 1.5 µmol) was added, and the reaction proceeded for 2 h in phosphate buffer (1 ml, 0.1M, pH 7.2, containing 2 mM ascorbic acid). The thus obtained title compound was purified by RP-HPLC using a C4 column, and characterized by SDS gel electrophoresis (12.5%) indicating the presence of (PEG$_{40}$-FMS)$_2$-hGH.

Example 25

Synthesis of PEG$_{40}$-FMS-hGH

MAL-FMS-NHS (280 µg) was added to a solution of hGH (4.5 mg, 0.225 µmol) in 0.5 ml PBS, pH=7.4. After 10 min, PEG$_{40}$-SH (10 mg) was added and the reaction mixture was stirred for 1 h and dialyzed overnight against water. The product, PEG$_{40}$-FMS-hGH, was purified by RP-HPLC.

Example 26

Synthesis of PEG$_{40}$-FMS-ANP

To a stirred solution of atrial natriuretic peptide (ANP) (0.32 μmol, 1 mg) in phosphate buffer (1 ml, 0.1 M, pH 7.2), MAL-FMS-NHS (2 eq, 0.2 mg, 0.7 μmol) was added. The reaction was carried out for 10 min at 25° C. Solid PEG$_{40}$-SH (2.2 eq, 30 mg, 0.7 μmol) was added, and the reaction proceeded for 2 h in phosphate buffer (1 ml, 0.1M, pH 7.2, containing 2 mM ascorbic acid). The product was further purified by HPLC.

II. Biological Section

In this section, the biological activity of the PEG-Fmoc and PEG-FMS conjugates with gentamicin, peptides and proteins prepared in the examples above, was tested.

Example 27

Inactive PEG-Fmoc-Gentamicin Conjugates Undergo Reactivation

For assaying the antibacterial potency of gentamicin and its derivatives, a suspension of *Escherichia coli* (*E. coli* strain N-4156-W.T, 1% v/v in LB medium) was divided into plastic tubes (0.5 ml per tube) and incubated in a shaking water bath at 37° C., in either the absence or the presence of increasing concentrations of gentamicin (0.02 to 2 μM), and increasing concentrations of PEG$_{5,000}$-gentamicin derivatives (0.02-50 μM). *E. coli* replication was evaluated by measuring the absorbance at 600 nm. Incubation was terminated when O.D$_{600}$ nm in the tubes containing no gentamicin reached a value of 0.6±0.1. Under our assay conditions, native gentamicin inhibited half-maximally *E. coli* replication at a concentration of 0.22±0.02 μM (0.1 μg/ml). A PEG-gentamicin derivative showing an IC$_{50}$ value of 2.2±0.2 μM in this assay is considered having 10% the antibacterial potency of native gentamicin.

(PEG$_{5,000}$-Fmoc)$_1$-gentamicin and (PEG$_{5,000}$-Fmoc)$_2$-gentamicin, containing one or two moles of PEG$_{5,000}$-Fmoc/mol gentamicin, respectively, were prepared as a model in order to assess the reversibility of the PEG-Fmoc moieties. Both derivatives (0.2 mM of each) were incubated in 0.1 M NaHCO$_3$ (pH 8.5) at 37° C., and aliquots were withdrawn at different times and then analyzed for their potency to arrest *E. coli* replication (see method (xi) above). The IC$_{50}$ for each aliquot was determined. Native gentamicin inhibited *E. coli* replication with IC$_{50}$ value of 0.22±0.2 μM. (PEG$_{5,000}$-Fmoc)$_2$- and (PEG$_{5,000}$-Fmoc)$_1$-gentamicin had 0.01 and 2.1±0.1% of the antibacterial potency of gentamicin, respectively.

Figure 3A:
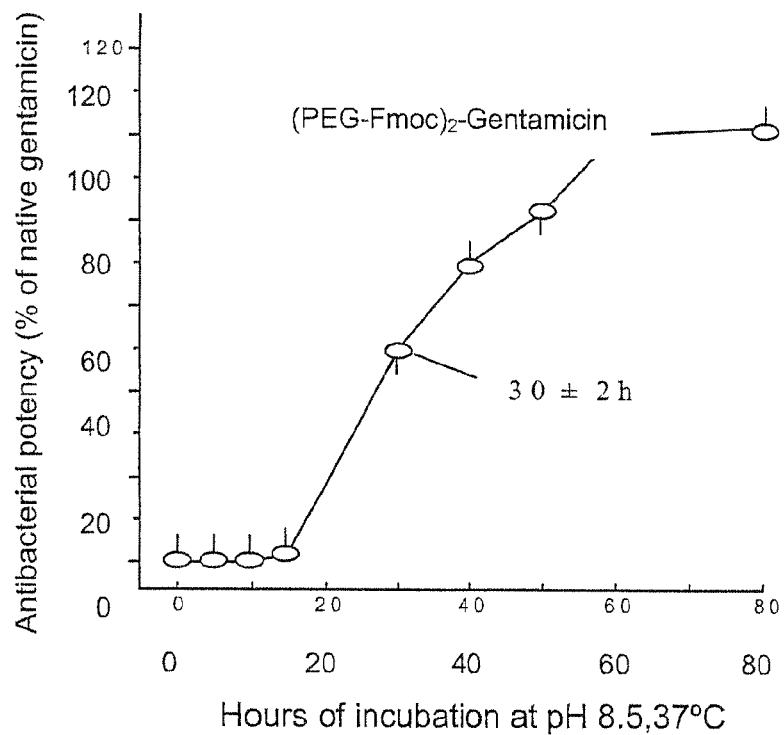
FIGS. 3A-3B show the time course of reactivation of (PEG$_{5000}$-Fmoc)$_2$-gentamicin and (PEG$_{5000}$-Fmoc)$_1$-gentamicin conjugates, respectively. After incubation at pH 8.5, 37° C., aliquots were withdrawn at the indicated time points and analyzed for their potency to arrest *E. coli* replication. The IC$_{50}$ for each aliquot was determined. Native gentamicin inhibited *E. coli* replication with IC$_{50}$ value=0.22±0.02 μM.
Figure 3B:
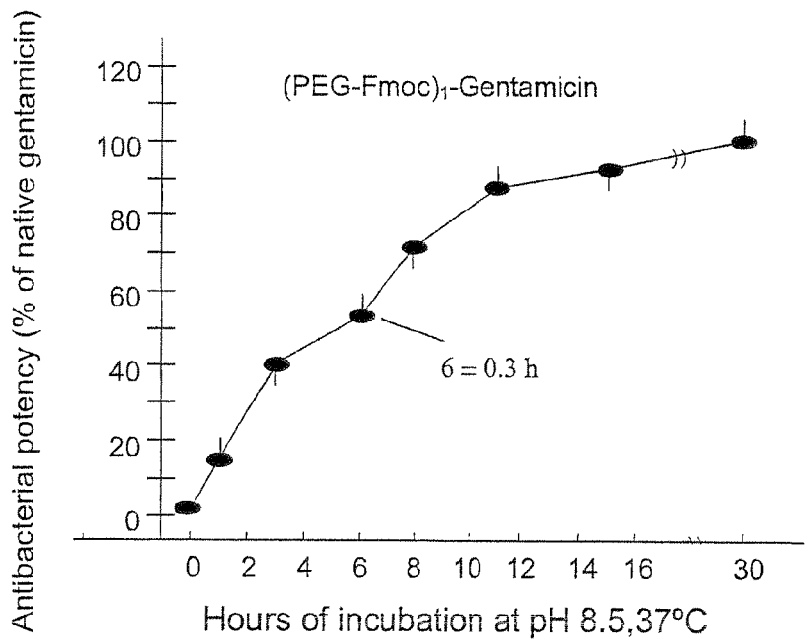

The results are shown in FIGS. 3A-3B. (PEG$_{5000}$-Fmoc)$_2$-gentamicin showed a prolonged lag period (about 15 hours) prior to noticeable reactivation (FIG. 3A). A sharp elevation in antibacterial potency then occurred, reaching 50 or 100% of the native potency after 30±2 or 60±3 hours of incubation, respectively (FIG. 3A). No lag period was observed upon incubation of (PEG$_{5,000}$-Fmoc)$_1$-gentamicin. Reactivation proceeded continuously with half-maximal reactivation at 6±0.3 hours, and full activation (100%) after 30 hours of incubation (FIG. 3B).

Example 28

Biological Activity of PEG-Fmoc-Insulin Conjugates

Materials and Methods (i) Materials. Recombinant human insulin was from Biotechnology General (Rehovot, Israel). D[U—$^{14}$C]Glucose (4-7 mCi/mol) was obtained from Du Pont NEN (Boston, Mass., USA). Collagenase type I (134 U/mg) was purchased from Worthington (Freehold, N.J., USA).

(ii) Rat adipocytes were prepared from fat pads of male Wistar rats (100-200 gr) by collagenase digestion as described (Rodbell, 1964). The fat pads were cut into small pieces with scissors and suspended in 3 ml of KRB buffer containing NaCl, 110 mM; NaHCO$_3$, 25 mM; Kcl, 5 mM; KH2PO$_4$, 1.2 mM; CaCl$_2$, 1.3 mM; MgSO$_4$, 1.3 mM; and 0.7% BSA (pH 7.4). Digestion was performed with collagenase type I (1 mg/ml) in a 25 ml flexible plastic bottle under an atmosphere of carbogen (95% O$_2$, 5% CO$_2$) for 40 min at 37° C. with vigorous shaking. Five ml of buffer was then added, and the cells were passed through a mesh screen. The cells were then allowed to stand for several minutes in a 15 ml plastic test tube at room temperature, floating, and the buffer underneath was removed. This procedure (suspension, floating, and removal of buffer underneath) was repeated three times.

(iii) Lipogenesis (incorporation of [U—$^{14}$C] glucose into the lipids of intact adipocytes). The incorporation of [U—$^{14}$C] glucose into adipose tissue in rat adipocytes was performed as described (Moody et al., 1974). Adipocyte suspensions (3×10$^5$ cells/ml) were divided into plastic vials (0.5 ml per vial) and incubated for 60 min at 37° C. under an atmosphere of carbogen with 0.2 mM [U—$^{14}$C]glucose, in either the absence or presence of insulin. Lipogenesis was terminated by adding toluene-based scintillation fluid (1.0 ml per vial) and the radioactivity in extracted lipids was counted. In a typical experiment, insulin-stimulated lipogenesis was 4-5 fold higher than basal (basal: 2000 cpm per 3×10$^5$ cell/h; V$_{insulin}$ 8,000-10,000 cpm per 3×10$^5$ cells/h). In this assay, insulin stimulates lipogenesis with ED$_{50}$ value=0.15±0.03 ng/ml. An insulin analog exhibiting ED$_{50}$ value=15 ng/ml is considered to have ~1% of the biological potency of the native hormone.

(iv) Glucose-lowering potency of insulin and its derivatives was determined in mice following administration under the conditions specified in each experiment. Blood samples were taken from the tail vein at different time points after administration, and blood glucose levels were determined with glucose analyzer (Beckman Instrumen, Fullerton, Calif., USA) by the glucose oxidase method. The level of glucose in normal healthy CD1-mice was 140±7 mg/dl (7.77 mM). Each group consisted of 4-5 mice. Data are presented as means±SEM.

28 (i). Progressive Modification of Amino Acid Moieties of Insulin with PEG$_{5000}$-Fmoc-OSu Human insulin was modified with increasing concentrations of Precursor 1 and loss of biological potency as a function of PEG$_{5000}$-Fmoc incorporated into insulin was determined.

Figure 4B:
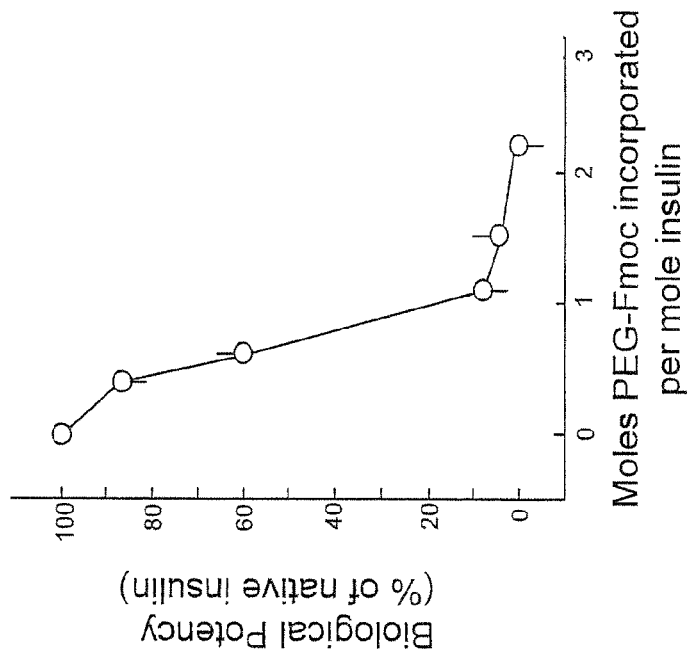
FIGS. 4A-4B show progressive modification of the amino acid moieties of human insulin with PEG$_{5000}$-Fmoc-OSu and loss of biological potency as a function of PEG$_{5000}$-Fmoc incorporated into insulin, respectively. (4A) Insulin (17.24 nmoles in 0.2 ml 0.01 M NaHCO$_3$) reacted with increasing concentrations of PEG$_{5000}$-Fmoc-OSu at a molar excess over the protein as indicated in the figure for 2 hours at 25° C. The number of free amino groups that remained unmodified were quantitated with TNBS. (4B) Aliquots containing 0.4, 0.7, 1.1, 1.5 and 2.2 moles PEG$_{5000}$-Fmoc covalently attached per mole insulin, were assayed for their lipogenic potency in rat adipocytes. Under the assay conditions, human insulin stimulates lipogenesis, 4-6 times above basal levels with ED$_{50}$ value of 0.2±0.02 ng/ml. An insulin derivative exhibiting ED$_{50}$ of 2.0±0.2 ng/ml in this assay is considered as having 10% the lipogenic potency of native insulin.
Figure 4A:
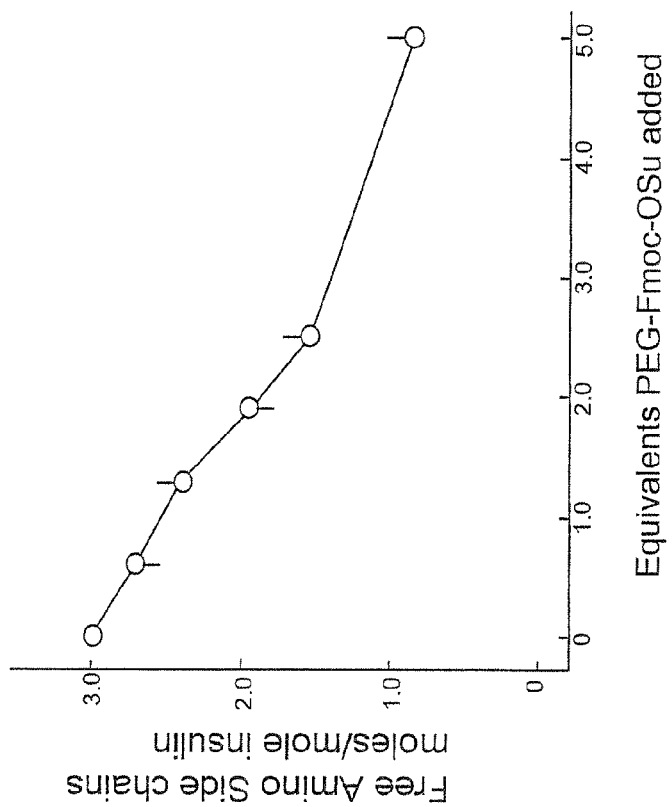

Insulin (17.24 nmoles in 0.2 ml 0.01 M NaHCO$_3$) reacted with increasing concentrations of PEG$_{5000}$-Fmoc-OSu at a molar excess over the protein as indicated in FIG. 4A for 2 hours at 25° C. The degree of derivatization was quantitated by determining the number of free amino groups that remained unmodified and were available for reaction with TNBS. Theoretically, insulin can incorporate 3 moles of $PEG_{5000}$-Fmoc on the amino side chains of Lys B29, PheB1 and GlyA1. As shown in FIG. 4A, upon reacting insulin with 0.6, 1.3, 1.9, 2.5 and 5.0 molar excess of $PEG_{5000}$-Fmoc-OSu, 0.3±0.03, 0.59±0.05, 1.1±0.1, 1.5±0.2 and 2.2±0.2 moles of $PEG_{5,000}$-Fmoc were incorporated into insulin, respectively, indicating that two (of the three) amino side chains of insulin are readily accessible for derivatization.

Aliquots containing 0.4, 0.7, 1.1, 1.5 and 2.2 moles $PEG_{5000}$-Fmoc covalently attached per mole insulin, were assayed for their biological potencies in a lipogenic assay in rat adipocytes. Under the assay conditions, human insulin stimulates lipogenesis, 4-6 times above basal levels with $ED_{50}$ value of 0.2±0.02 ng/ml. An insulin derivative exhibiting $ED_{50}$ of 2.0±0.2 ng/ml in this assay is considered as having 10% the lipogenic potency of native insulin. The results in FIG. 4B show that the respective biological potencies were 87±4, 60±3, 8±1, 4±0.3 and less than 1% when 0.3, 0.6, 1.1, 1.5 and 2.2 mol $PEG_{5000}$-Fmoc/mol insulin has been incorporated.

28(ii). $PEG_{5000}$-Fmoc-Insulins Undergo Time-Dependent Reactivation

Figure 5:
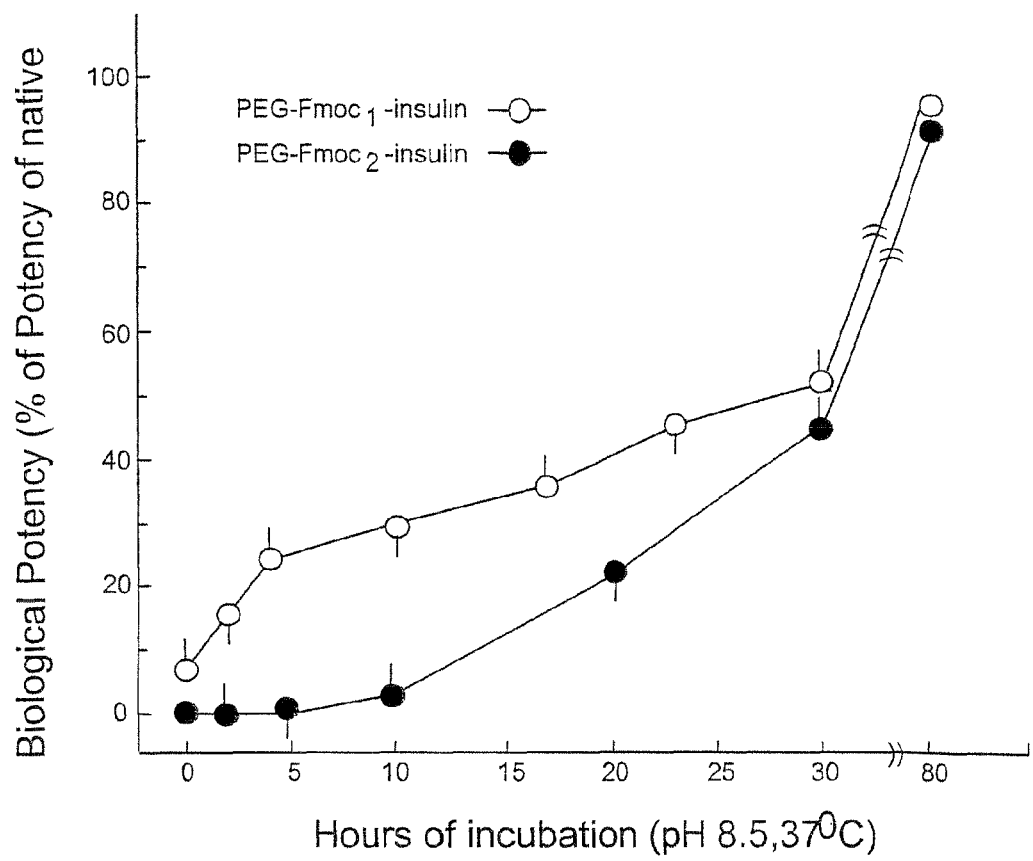
FIG. 5 shows the rate of reactivation of PEG$_{5000}$-Fmoc-insulin conjugates upon incubation at pH 8.5, 37° C.

Insulin conjugates containing one and two moles of $PEG_{5000}$-Fmoc/mole insulin were incubated for different times at a concentration of 0.172 µM in 0.1 M $NaHCO_3$ –0.5% bovine serum albumin (BSA) and 1 mM $NaN_3$ (pH 8.5) at 37° C. The results are shown in FIG. 5. At the indicated time points, aliquots were analyzed (in several concentrations for each aliquot) for their lipogenic potencies in rat adipocytes. With $(PEG_{5000}$-Fmoc$)_2$-insulin, no reactivation could be observed in the first 10 hours of incubation. Lipogenic activity then increased, reaching 45±3 and 90% of the native insulin potency at 30±2 and 80±4 hours, respectively.

With $(PEG_{5000}$-Fmoc$)_1$-insulin, no such lag period was observed. Activity was regenerated slowly but continuously yielding 16, 24, 30, 36 and 95% of the native potency following 2, 4, 10, 17 and 80 hours of incubation, respectively. Insulin containing about one mole of $PEG_{5000}$-Fmoc/mol insulin ($PEG_{5000}$-Fmoc$_1$-insulin) was therefore selected for further studies. Mass-spectrum and analytic HPLC analyses revealed that this preparation contains predominantly monomodified derivatives of insulin (MW=11,096 kDa), the remainder being unmodified insulin (about 5%, MW=5,813 kDa) and small quantities of bis(MW=16,587 kDa) and tris (MW=22,661 kDa) modified derivatives.

As shown in FIG. 4B, $(PEG_{5000}$-Fmoc$)_1$-insulin has 7±1% the biological potency of the native hormone prior to undergoing PEG-Fmoc hydrolysis. Based on these findings in vitro, $(PEG_{5000}$-Fmoc$)_1$-insulin was administered in vivo at ten times higher concentrations than the native hormone, in order to obtain the same glucose-lowering effect (see below).

28(iii). $(PEG_{5000}$-Fmoc$)_1$-Insulin Facilitates Prolonged Glucose-Lowering Action In Vivo Native insulin ($Zn^{2+}$ free, 1.72 nmol/mouse) or $(PEG_{5000}$-Fmoc$)_1$-insulin (17.2 nmoles/mouse) were administered subcutaneously to groups of mice (n=5 in each group), and the glucose lowering profiles were determined. The results are shown in FIG. 6. Native insulin reduced blood glucose level maximally at 30 min. Circulating glucose levels then returned to normal values with $t_{1/2}$=1.8±0.2 hours. Following subcutaneous administration of (PEG-Fmoc)$_1$-insulin, circulating glucose levels were lowered maximally at 4 hours, and were then maintained at the low glucose level for an additional 4 hours, before returning to the normal values with a $t_{1/2}$=12±1 hours (FIG. 6).

28(iv) $(PEG_{5000}$-Fmoc$)$-Insulin Manifests Prolonged Glucose Lowering Action Also after Intraperitoneal Administration The prolonged action of subcutaneously administered $(PEG_{5000}$-Fmoc$)_1$-insulin can be attributed, theoretically, to a slower absorption rate from the subcutaneous compartment to the circulation as well as to the low fraction of the administered material exposed to receptor-mediated degradation and hydrolysis of the inactive to the active species. In order to differentiate between these factors, the subcutaneous compartment was bypassed by administering native insulin ($Zn^{2+}$-free, 0.345 nmoles/mouse, in 0.2 ml PBS buffer) or $(PEG_{5000}$-Fmoc$)_1$-insulin (3.45 nmoles/mouse, in 0.2 ml PBS buffer) intraperitoneally. The glucose lowering capacities were then monitored. Blood glucose levels were determined at different time points.

The results are shown in FIG. 7. Following administration of insulin, circulating glucose levels fell maximally at 15 min and returned to normal level with a $t_{1/2}$ value of 1.0±0.1 hours. In the case of intraperitoneally administered $(PEG_{5000}$-Fmoc$)_1$-insulin, circulating glucose level declined more gradually, reaching a maximal fall at 1.0 hour. Levels were then gradually elevated, showing a $t_{1/2}$ value of 3.4±0.1 hours, and returning to normal values only 6 hours after administration (FIG. 7).

Example 29

Biological Activity of PEG-FMS-Exendin Conjugates

Exendin-4 is an insulinotropic glucagon-like peptide-1 (GLP-1) agonist associated with the β-pancreatic cells, elevates endogenous cAMP levels, enhances secretion of insulin, and lowers circulating glucose levels (Eng et al., 1992; Goke et al., 1993; Schepp et al., 1994; Fehmann et al., 1994). A profound pharmacological advantage of this GLP-1 agonist is that, following administration at any dosage, the circulating blood glucose level (BGL) never falls below a threshold glucose level that, in non-diabetic healthy CD1-mice, is 74±7 mg/dl (Shechter et al., 2003).

According to the present invention, the conjugate $PEG_{40000}$-FMS-exendin-4 was prepared (Example 19). Exendin-4 contains one His Nα amino function and two Lys Nε amino groups, enabling modification at these three positions. Indeed, N-terminal amino acid sequencing revealed that, although the $PEG_{40000}$-FMS-exendin-4 product eluted as a single peak on HPLC, it was actually a mixture containing primarily the Nα-modified hormone. However, in view of the pegylation reaction's reversibility according to the present invention, regenerating the native peptide and protein hormones in physiological environment, this point deserves only minor consideration.

Materials and Methods (i) Materials. Exendin-4 and a non-lysine-containing synthetic irrelevant peptide of 27 amino acids (SEQ ID NO: 14) were synthesized by the solid phase method using a multiple-peptide synthesizer, AMS 422 (Abimed Analyser Technik GmbH, Langenfeld, Germany). An Fmoc-strategy was employed throughout the peptide-chain assembly. 5,5-dithio-bis(2-nitrobenzoic acid) (DTNB), reduced glutathione (GSH) and trinitrobenzene sulfonic acid (TNBS) were purchased from Sigma Chemical Co., (St. Louis, Mo., USA). All other materials used in this study were of analytical grade.

$PEG_{40000}$-FMS-exendin-4 and $PEG_{5000}$-FMS-exendin-4 were prepared as described in Examples 18 and 19, respectively.

For the preparation of $PEG_{40000}$-exendin-4, exendin-4 (0.3 mg, 75 nmol) was dissolved in PBS (pH=7.5) and reacted with $PEG_{40000}$-OSu (20 mg, 470 nmol) for 3 h, filtered (×7) through Centricon (cut off=50 kDa) and characterized by MALDI-TOF mass spectrometry (found 48074 Da).

$PEG_{40000}$-FMS-Peptide 27 was prepared as described for $PEG_{40000}$-FMS-exendin-4.

A Centricon-50 ultrafiltration device for aqueous solutions was purchased from Millipore S.A. (France).

Ultraviolet spectra were obtained by Beckman DU 7500 spectrophotometer in 1 cm path length UV cuvettes. Mass spectra were determined using MALDI-TOF and ESMS techniques (Bruker-Reflex-Reflectron model, Germany, and VG-platform-II electrospray single quadrupole mass spectrometer, Micro Mass, U.K., respectively).

(ii) HPLC analyses were performed using a Spectra-Physics SP8800 liquid chromatography system equipped with an Applied Biosystems 757 variable wavelength absorbance detector, and a Spectra-SYSTEM P2000 liquid chromatography system equipped with a Spectra-SYSTEM AS100 autosampler and a Spectra-SYSTEM UV1000, all controlled by a ThermoQuest chromatography data system (ThermoQuest Inc., San Jose, Calif., USA). The column effluents were monitored by UV absorbance at 220 nm. Analytical RP-HPLC was performed using a pre-packed Chromlith™ Performance RP-18e (4.6×100 mm, Merck, Darmstadt, Germany). The column was eluted with a binary gradient of 10-100% solution B over 10 min with a flow rate of 3 ml/min (solution A was 0.1% TFA in $H_2O$ and solution B was 0.1% TFA in acetonitrile:$H_2O$; 3:1, v:v). PEGylated compounds were analyzed using a RP-4 column (250×4 mm, 5 μm bead size, VYDAC, Hesperia, Calif., USA) with a binary gradient of 10-100% solution B in 50 min at a flow rate of 1 ml/min.

(iii) Preparative separations were performed with pre-packed VYDAC RP-18 or RP-4 columns (250×22 mm; Hesperia, Calif.). The column was eluted with 10-100% solution B over 60 min (12 ml/min).

(iv) Glucose-lowering assay. Three groups of CD1 mice (n=6 per group) were subcutaneously administered with saline, native exendin-4 (4 μg/mouse) or $PEG_{40000}$-FMS-exendin-4 (4 μg peptide/mouse). Circulating glucose levels were measured with a glucose analyzer (Beckman Instrument, Fullerton, Calif., USA) by the glucose oxidase method. Blood samples for the blood glucose analyses were taken from the tail veins. The level of glucose in normal healthy CD1-mice was 140±7 mg/dl (7.77 mM).

29(i) PEG-FMS-Exendin-4 Releases Exendin-4 Upon Incubation

A solution of $PEG_{40}$-FMS-exendin-4 (0.25 mM, 1 ml/ml in terms of exendin-4 in 0.1 M $NaHCO_3$, pH 8.5) was incubated at 37° C. At different time points, aliquots (50 μl) were withdrawn and analyzed for the release of exendin-4 from the conjugate, using HPLC on a RP-4 column. As shown in FIG. 8, exendin-4 was released from the conjugate [$PEG_{40}$-FMS]$_2$-exendin-4 in a slow, homogeneous fashion, with a $t_{1/2}$ of 16±2 h. Exendin-4 was fully released from the conjugate after 48 h of incubation.

29(ii) The Hydrolysis Rates and Reaction Orders of $PEG_{40}$-FMS-Exendin-4, $PEG_{5000}$-FMS-Exendin-4 and $PEG_{5000}$-FMS-4-Nitro-Phenethylamine The hydrolysis rates and reaction orders of the PEG-FMS conjugates $PEG_{5000}$-FMS-4-nitro-phenethylamine, $PEG_{5000}$-FMS-exendin-4 and $PEG_{40}$-FMS-exendin-4, and one MAL-FMS conjugate, N-(MAL-FMS)-Peptide 27, were evaluated at pH=8.5, 37° C. The structures and half-lives of the conjugates are presented in Table 3. $PEG_{5000}$-FMS-4-nitro-phenetylamine was prepared as described in Example 20. The conjugate MAL-FMS-Peptide 27 was prepared by reaction of MAL-FMS-NHS with the non-relevant peptide 27 (SEQ ID NO:14).

FIG. 9 shows the hydrolysis of $PEG_{5000}$-FMS-exendin-4 (circles) and of $PEG_{5000}$-FMS-4-nitro-phenethylamine (squares) after incubation in PBS at pH 8.5, 37° C. Results in FIGS. 8 and 9 are expressed as percent of the maximal peak area of released exendin-4 and 4-nitrophenethylamine, as a function of time.

The hydrolysis rate at pH 8.5 is equivalent to the hydrolysis rate in serum. The release of 4-nitro-phenethylamine and exendin-4 was monitored by RP-HPLC and was determined to be a first order reaction (Table 3 and FIGS. 8, 9). As shown (FIGS. 8-9, Table 3), the peptides and protein were released from the conjugates in a slow homogenous fashion, with $t_{1/2}$ of 9.4 ($PEG_{5000}$-FMS-4-nitro-phenethylamine), 13.8 ($PEG_{5000}$-FMS-exendin-4), and 11.9 ($PEG_{40000}$-FMS-exendin-4). Exendin-4 was fully released from the $PEG_{40}$ conjugate after 48 h of incubation.

The conjugate MAL-FMS-Peptide 27 is TNBS negative as the sole α-amino moiety of Peptide 27 was derivatized. A solution of MAL-FMS-Peptide 27 (0.5 mM in 0.1 M $NaHCO_3$, pH 8.5) was incubated at 37° C. Aliquots (0.2 ml) were withdrawn at different time points and analyzed for the appearance of the free α-amino group using TNBS. The FMS-MAL (N-ethyl maleimide) moiety was hydrolyzed in a slow and nearly homogeneous fashion from the α-amino moiety of the peptide, with a $t_{1/2}$ value of 8.4 h. Hydrolysis was complete after 32 hrs of incubation.

29(iii) $PEG_{40}$-FMS-Exendin-4 Facilitates Prolonged Glucose Lowering Action in Mice FIGS. 10A-10B show the glucose-lowering profile of subcutaneously administered native exendin-4 and of $PEG_{40}$-FMS-exendin-4, both at a dose of 10 μg (FIG. 10A) or 4 μg (FIG. 10B) peptide/mouse relative to a saline-treated group of mice.

FIG. 10A shows the glucose lowering profile of subcutaneously administered native-exendin-4 and of $PEG_{40}$-FMS-exendin-4, both at a dose of 10 μg/mouse. With the native peptide, blood glucose levels declined from 139±10 to 96±7 within 0.5 h reaching a maximal fall in 2-4 hours after administration (74 mg/dl). The return to initial glucose level was then proceeded with a $t_{1/2}$ value of 14.2±1 h. Following the subcutaneous administration of $PEG_{40}$-FMS-exendin-4, little decrease in blood glucose level is seen at 0.5 h after administration. Circulating glucose level then fall gradually, with the lowest glucose concentration reached at 6-8 hours after administration (80-90 mg/dl). Stable, low circulating glucose concentrations then maintained over nearly 50 hours, prior to the return to initial glucose levels with a $t_{1/2}$ value of 70±3 hrs.

FIG. 10B shows the glucose lowering profile of subcutaneously administered native-exendin-4 and of $PEG_{40}$-FMS-exendin-4, both at a dose of 4 μg/mouse. With the native peptide, blood glucose levels declined by 26-28% (from 140 mg/dl to 104-101 mg/dl), with the largest percent change in blood glucose levels occurring 0.5-1 h after administration. Glucose concentrations then returned to their initial levels with a $t_{1/2}$ value of 3.7±0.3 h. Following the subcutaneous administration of $PEG_{40}$-FMS-exendin-4, the decrease in blood glucose level took place at a more moderate rate. Circulating glucose reached its lowest concentration 8-12 hours after administration (92 mg/dl, 33%). Stable, low circulating glucose concentrations were then maintained for a further 12 hours. Return to initial glucose levels took place with a $t_{1/2}$ of 30±2 h, being 7.5 times longer than that obtained by the same dose of the native hormone.

Calculations based on the hydrolysis rates of FMS-exendin-4 (described in U.S. patent application Ser. No. 10/408, 262) and $PEG_{40000}$-FMS-exendin-4 at 37° C. in normal sera and PBS (pH 8.5), respectively, revealed that ~4% of exendin-4 is released from the conjugate each hour in vivo (Shechter et al., 2001). We further hypothesized that this release rate, if combined with prolonged maintenance of the conjugate in the circulatory system, prior to exendin-4 hydrolysis, should yield a long-lasting glucose-lowering signal in mice, as indeed is found following a single subcutaneous administration of $PEG_{40000}$-FMS-exendin-4 conjugate (FIG. 10B). Irreversibly conjugated $PEG_{40000}$-exendin-4 has only ≤1% of the activity of native exendin-4 ($IC_{50}$=250±30 pmol/mouse versus $IC_{50}$=2.5±0.24 pmol/mouse for the native exendin-4, not shown).

Example 30

Biological Activity of $PEG_{40}$-FMS-IFNα2

Type I interferons (IFNs) are proteins that initiate antiviral and antiproliferative responses. Interferons are clinically important, and several subtypes of IFNα2 were approved as drugs for the treatment of hepatitis B and C as well as for cancers such as chronic myelogenous leukemia and hairy cell leukemia. Interferons regulate signals through the Janus tyrosine kinase (Jak/STAT proteins), and by reducing phosphorylation and activation of MEK1 and ERK1/2 through a Ras/Raf independent pathways (Romerio et al., 2000). Human type I interferons induce differential cellular effects, but act through a common cell surface receptor complex comprised of the two subunits, Ifnar1 and Ifnar2. Human Ifnar2 binds all type I IFNs, but with a lower affinity and specificity than the Ifnar complex. Human Ifnar1 has a low intrinsic binding affinity towards human IFNs, but modulates specificity and affinity of other ligands of the Ifnar complex (Cutrone and Langer, 2001).

IFNα2 may be administered intramuscularly, subcutaneously or intravenously, resulting in different pharmacokinetic profiles. In any mode, the administered cytokine is rapidly inactivated by body fluids and tissues (O'Kelly et al., 1985), and cleared from the blood plasma several hours following administration (Rostaing et al., 1998). The major routes of IFNα2 elimination from the circulatory system are through proteolysis, receptor mediated endocytosis and kidney filtration (Goodman and Gilman, 2001).

Prolonging the maintenance dose of IFNα2 in circulation is a desirable clinical task. A non-reversible, 12 kDa-PEG-IFNα2 conjugate, has been therapeutically approved in 2001. It is administered once a week to hepatitis C patients, and facilitates a sustained anti-viral response rate of 24%, as opposed to a 12% response rate obtained by the native cytokine (Schering-Plough Corporation, 2001 press release; Baker, 2003). However, while the covalent attachment of PEG chains to proteins prolongs their lifetime in vivo, it often results in a dramatic reduction or even loss of biological and pharmacological activities (Fuertges and Abuchowski, 1990; Katre, 1993; Bailon and Berthold, 1998; Nucci et al., 1991; Delgado et al., 1992; Fung et al., 1997; Reddy, 2000; Veronese, 2001). The pegylated formulation of IFNα2 currently in use has 7% the activity of the native cytokine, calling for higher doses to be administered (Bailon et al., 2001). Furthermore, PEG-IFN does not readily penetrate all tissues: while 12 kDa PEG-IFNα2b is widely distributed, 40 kDa-PEG-IFNα2a is restricted to the blood and the interstitial fluid (Glue et al., 2000; Reddy et al., 2002). This major drawback can be overcome by designing a PEG-IFNα2 conjugate capable of generating native IFNα2 at a slow rate under physiological conditions.

These problems of the prior art can be overcome by the mono- and bis-$PEG_{40}$-FMS-IFN-α2 conjugates of the invention, in which IFN-α2 is linked to the PEG moiety through the FMS moiety that provides the slowly hydrolysable bond. These novel reversibly pegylated-conjugates and their prolonged anti-viral activity in vivo are discussed here in detail.

Materials and Methods (i) Materials. Non-glycosylated human IFN-α2 was prepared as described in in WO 02/36067 as previously described by Piehler and Schreiber (1999). Preparation of $PEG_{40}$-FMS-IFNα2 and $(PEG_{40}$-FMS$)_2$—IFNα2 is described in Examples 21 and 22, respectively.

(ii) Receptor binding affinities were evaluated by BIAcore (SPR Detection) measurements. The BIAcore® 3000 system, sensor chips CMS, HBS (10 mM Hepes, 3.4 mM EDTA, 150 mM NaCl, 0.05% surfactant P20, pH 7.4) and the amine coupling kit were from BIAcore (Sweden). Chip immobilization by Ifnar2 and the BIAcore measurements were carried out according to Piehler and Schreiber (2001). In short, Ifnar2-EC was immobilized to the surface using the non-neutralizing anti-Ifnar2-EC (Ifnar2-extra cellular) mAb 46.10, followed by cross-linking with a second mAb (117.7) (kindly provided by D. Novick, Weizmann Institute of Science, Rehovot, Israel). The binding curves were evaluated with the BIAevaluation software (Biacore AB, Sweden) using a simple one-to-one kinetic model. Increase in RU (resonance unit) after specific binding to the receptor corresponds to the amount of protein bound to the sensor surface. To estimate the increase in RU resulting from the nonspecific effect of the protein on the bulk refractive index, binding of the protein to a control surface with no immobilized ligand was also measured and subtracted. For the determination of the active interferon concentration the equilibrium response was plotted against the estimated initial concentration. The data were fitted using KaleidaGraph (version 3.0.4, Abelbeck Software) using the equation:

$$y = \frac{1 * 10^8 * m1 * m2}{1 * 10^8 * m1 * m0 + 1}$$

whereby a $K_A$ of $1 \times 10^8$ was determined independently for IFNα2 binding and fixed for all samples, m1=is Ru/Rmax (the percent of active interferon measured in the sample), m2 is Rmax, and m0 is the observed Ru.

(iii) In vivo experiments were performed using male Wistar rats (150-170 g). Rats were injected either subcutaneously or intravenously (0.2 ml/rat).

(iv) Antiviral activity of IFNα2 and its derivatives was determined by the capacity of the cytokine to protect human amnion WISH cells against Vesicular Stomatitis Virus (VSV)-induced cytopathic effects (Rubinstein et al., 1981).

(v) Simulations of experimental data were performed using Pro-Kineticist II, a $2^{nd}$ Order Global Kinetic Analysis software (Applied Photophysics Ltd., England).

For the i.v. administration, the following model was considered:

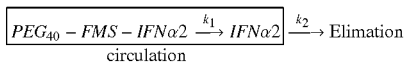

Whereby, $k_1=0.01$ $hr^{-1}$ and $k_2=0.65$ $hr^{-1}$ (determined experimentally by antiviral assay).

For the s.c. administration, the following model was considered:

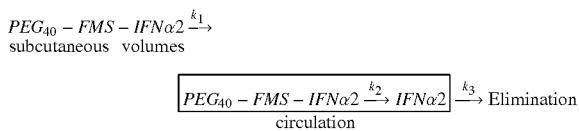

Whereby, $k_1=0.02$ $hr^{-1}$, $k_2=0.01$ $hr^{-1}$, and $k_3=0.65$ $hr^{-1}$.

$k_1$, which could not be determined directly, was estimated to be 0.02 $hr^{-1}$ from the fit of the simulation to the experimental data.

30(i) PEG$_{40}$-FMS-IFNα2 has Modified Receptor-Binding Capacity

The binding capacity of the modified IFNα2 of the invention toward the immobilized recombinant extracellular part of IFNα2 receptor (ifnar2-EC) was monitored under flow-through conditions by an optical probe called reflectometric interference spectroscopy (RIFS). This method detects biomolecular interactions of ligands to transducer-bound proteins as a shift in the interference spectrum caused by change of the apparent optical thickness of the transducer chip. A shift of 1 pm corresponds to approximately 1 pg/mm² protein on the surface. The transducer surface was modified with a dextran layer and carboxylated by reaction with molten glutaric anhydride (S administered to rats (30 μg/rat) intravenously. For native interferon, the same half-life was measured, indicating that it readily penetrates the circulatory system following subcutaneous administration (FIG. 13). For PEG$_{40}$-FMS-IFNα2, antiviral activity was still detected 150 hours following intravenous administration, demonstrating the prolonged effects of the pegylated cytokine. Discharged IFNα2 level of 10 pM still remained 150 hours post administration, while native IFNα2 was eliminated within 30 hours post-administration. It should be noted that the large shoulder observed following subcutaneous administration of the conjugate (FIG. 12) is not observed when PEG$_{40}$-FMS-IFNα2 was administered intravenously (FIG. 13).

30(v) Simulations of Experimental Data

Using the rate constants obtained from both BIAcore data (k=0.01 hr$^{-1}$ for the discharge of IFNα2 from the PEG conjugate) and the antiviral activity assay of native IFNα2 (k=0.65 hr$^{-1}$ for the elimination of interferon), both the subcutaneous and intravenous administration modes of PEG$_{40}$-FMS-IFNα2 to rats were simulated (FIGS. 14A and 14B, respectively). In both cases, the simulated data and the experimental results were in good agreement. As became evident from the simulated data, the passage of the conjugate, but not of the native interferon, from the subcutaneous volume to the bloodstream, proceeds at a slow rate and is in the order of the discharge of interferon from the conjugate. This explains the shoulder observed between 10-70 hours in the active protein concentration. As expected, this shoulder is not found when PEG$_{40}$-FMS-IFNα2 is administered intravenously.

Discussion

As mentioned before, the pegylating technology applied to therapeutic proteins often leads to a drastic loss in the biological and the pharmacological potencies of the conjugates. In principle, this deficiency can be overcome by introducing the PEG chains via a chemical bond that is either sensitive to hydrolysis or can be cleaved enzymatically by serum proteases or esterases. A prerequisite condition for efficient pegylation is that the hydrolysis of the PEG chains from the conjugate is to take place at a slow rate, and in a homogenous fashion in vivo.

Two basic irreversible PEG-IFNα2 conjugates are in therapeutic use at present. The first, a 12 kDa-PEG-IFNα2, which satisfactorily permeates into tissues. This preparation, however, is a relatively short-lived in vivo, since its low molecular mass (calculated mass=32 kDa) is insufficient to markedly arrest kidney filtration. The second formulation, a 40 kDa-PEG-IFNα2, is an extremely long-lived species in vivo. This conjugate, however, has poor permeability into tissues. Following administration, the conjugate is distributed only in the blood and in the intestinal fluids (Bailon et al., 2001). We have, therefore, anticipated that the two prerequisite features for an optimal PEG-IFNα2 conjugate, namely, a prolonged maintenance in vivo combined with free access to peripheral tissues, can be obtained by linking a slowly hydrolyzable PEG$_{40}$-chain to IFNα2.

We have previously found that upon linkage of FMS to proteins, the FMS-protein conjugate undergoes hydrolysis at physiological conditions with a desirable pharmacokinetic pattern (Gershonov et al., 2000; Shechter et al., 2001, 2002, 2003). The rate of FMS hydrolysis is dictated exclusively by the pH and the nucleophilicity of the serum, both of which are maintained in mammals under strict homeostasis (Shechter et al., 2001). We therefore based our new development on the FMS principle. In neutral, aqueous solutions, FMS moieties undergo slow, spontaneous hydrolysis, resulting in the regeneration of the native proteins (Shechter et al., 2001). For this purpose, NHS-FMS-MAL was synthesized, enabling us to link sulfhydryl-containing PEG chains to the amino groups of peptides and proteins via the hydrolyzable FMS function. The working hypothesis was that an inactive PEG-interferon conjugate could regenerate the native protein in its active form in a continuous fashion over a long period of time. The principal monomodified PEG$_{40}$-FMS-IFNα2 conjugate obtained (Table 2) is devoid of the cytokine binding potency and can therefore be referred to as a 'prodrug'. Upon incubation, the native cytokine is released by hydrolysis, and the binding potency of IFNα2 to Ifnar2 is regenerated with a rate constant of 0.01 hr$^{-1}$.

A single subcutaneous administration of PEG$_{40}$-FMS-IFNα2 significantly prolonged the levels of IFNα2 in the serum of rats. While IFNα2 was short-lived in vivo, having a half-life of ~1 hr, the PEG$_{40}$-FMS-IFNα2 conjugate exerted its antiviral activity over a period of 200 hours. Furthermore, there is a dose-dependent ratio between the quantity administered and the active interferon levels over a prolonged duration in vivo. This observation is beneficial for optimization of dosing regimens in future clinical use.

It should be noted that the IFNα2 molecule contains 13 amino functions theoretically available for PEG$_{40}$-FMS attachment. The exact site of pegylation was not determined. In view however, of its reversibility and the generation of the native protein, it seems that this point deserves a rather minor consideration.

In summary, following the new conceptual approach for reversible-pegylation of the invention, whereby a pharmacologically 'silent' conjugate is 'trapped' in the circulatory system and releases the parent protein with a desirable pharmacokinetic profile, we have succeeded in combining prolonged maintenance of IFNα2 in vivo with the release of active-native IFNα2 to ensure access to peripheral tissues.

Example 31

Biological Activity of the PEG$_{40}$-FMS-PYY$_{3-36}$ Conjugate

The hypothalamic family of neuropeptide Y (NPY) receptors plays a major role in regulating satiety and food intake (Schwartz, 2000). The putative inhibitory Y2 pre-synaptic receptor (Y2R) is expressed in the arcuate nucleus, which is accessible to local and peripheral agonists of the NPY family (Broberger et al., 1997; Kalra et al., 1999). One such Y2R agonist is peptide YY$_{3-36}$ (PYY$_{3-36}$), which is released from the gastrointestinal tract post-prandially in proportion to the caloric content of a meal (Pedersen-Bjergaard et al., 1996; Adrian et al., 1985; Grandt et al., 1994). Recently, it was demonstrated that peripheral administration of PYY$_{3-36}$ inhibits food intake in humans, mice and rats and reduces weight gain in rats [Pittner et al., 2002; Batterham et al., 2002, 2003). Thus, infusion of PYY$_{3-36}$ to reach the normal postprandial circulatory concentrations of this peptide lead to a peak in serum PYY$_{3-36}$ within 15 min, followed by a rapid decline to normal levels within 30 min. Despite this rapid clearance, administration of PYY$_{3-36}$ to fasting individuals decreases their appetite and reduces food intake by 33% within a 12 h period following PYY$_{3-36}$ administration. Furthermore, no compensatory food intake occurs over the next 12 h (Batterham et al., 2002). Therefore, PYY$_{3-36}$ may find a clinical use in treatment of obesity and its associated disorders, including type II diabetes mellitus and cardiovascular diseases (Schwartz and Morton, 2002).

The short circulatory half-life of PYY$_{3-36}$ and its potential in management of obesity prompted us to develop a longer-acting form of PYY$_{3-36}$. Indeed, in our hands the satiety induced by PYY$_{3-36}$ in mice lasted for only 2-4 h following subcutaneous (sc) injection. As mentioned before, covalent attachment of PEG to proteins and peptides prolong their half-life in vivo but often leads to a drastic loss of their biological or pharmacological activity. We found that PYY$_{3-36}$, pegylated using standard chemistry, i.e. through formation of a stable bond, indeed lost its biological activity. We have then prepared and test here the biological activity of the PEG$_{40}$-FMS-PYY$_{3-36}$ pro-drug of the invention.

Materials and Methods (i) Animals. C57BL/6J male mice (Harlan Labs) aged 9±1 week (20-30 g body weight) were used. Mice were kept under controlled temperature (21-23° C.) and light conditions (light on 6:00-18:00) at the Weizmann Institute of Science (Rehovot, Israel) animal facility. The mice were acclimated for at least one week prior to the initiation of the study. Mice had free access to drinking water at all times during the experiments. All experimental protocols were in accordance with the Israeli regulations of laboratory animal welfare and were approved by the Institutional Internal Committee for Animal Welfare.

(ii) Reagents. Peptide YY$_{3-36}$ was synthesized by the solid phase method, using a multiple-peptide synthesizer AMS 422 (Abimed Analyser Technik GmbH, Langenfeld, Germany). The resulting peptide was HPLC-purified and characterized by MALDI-TOF mass spectroscopy (MS) and N-terminal protein micro-sequencing. All other reagents were of analytical grade and were purchased from Sigma Chemical Co. (Ness Ziona, Israel).

(iii) Analytical Procedures. Mass spectra were determined using MALDI-TOF and Electro Spray (ES-MS) techniques (Bruker-Reflex-Reflectron model, Germany, and VG-platform-II electrospray single quadropole mass spectrometer, Micro Mass, U.K., respectively). PYY$_{3-36}$, PEG$_{40}$-FMS-PYY$_{3-36}$ and PEG40 were resolved by analytical HPLC (Lichrosorb RP-4 column, 4×250 mm, Merck). Buffer A was 0.1% aq. trifluoroacetic acid (TFA) and Buffer B was 0.1% TFA in 75% aq. Acetonitrile. A gradient of 10-100% Buffer B was used over 50 min. at a flow rate of 1 ml/min. The retention times (Rt) of PYY$_{3-36}$, PEG$_{40}$-FMS-PYY$_{3-36}$ and PEG$_{40}$-9-sulfo-fulvene were 21.53, 39.03 and 44.387 min., respectively. Amino acid analyses were performed following 6N HCl hydrolysis at 110° C. for 24 h using a Dionex Automatic amino acid analyzer HP1090 (Palo Alto, Calif., USA). N-terminal sequence analyses were performed with a Model 491A Procise Protein sequencer (Applied Biosystems, Foster City, Calif., USA).

(iv) Synthetic Procedures:

PEG$_{40}$-FMS-PYY$_{3-36}$ was Prepared as in Example 23.

PEG$_{40}$-FMS-Glycine ethyl ester (PEG$_{40}$-FMS-GEE). To a stirred solution of PEG$_{40}$-SH (0.25 mM in 0.1M phosphate buffer pH 7.2-10 mM Na ascorbate), 292 μg MAL-FMS-NHS was added (two-fold molar excess over PEG$_{40}$-SH). After 7 min, 0.2 ml from a solution of 0.5M glycine ethyl ester was added. The reaction was carried out for 1 h, and the mixture was then dialyzed overnight against water. The resulting PEG$_{40}$-FMS-glycine ethyl ester was characterized and quantitated by its absorbance at 280 nm/$\epsilon_{280}$=21,200) and by the amount of glycine in the preparation following acid hydrolysis of a 20 μl aliquot and amino acid analysis.

PEG$_{40}$-PYY$_{3-36}$. Irreversibly pegylated PYY$_{3-36}$ was prepared by reacting PYY$_{3-36}$ (1 mg/ml in 0.1 M phosphate buffer pH 7.2) with four equivalents of solid PEG$_{40}$-OSu, (43 mg). The reaction was carried out for 1 h and the mixture was then dialyzed overnight against water. The conjugate thus obtained contains one PEG$_{40}$ residue per PYY$_{3-36}$, as determined by MALDI-TOF MS. (PEG$_{40}$-OSu, 43,626 D; PYY$_{3-36}$, 4,047 D; conjugate, 47,712 D).

(v) Food intake measurements: Groups of 10 mice were deprived of food for 24 h and then given excess pre-weighed standard chow for a period of 2 h. Drinking water was provided at all times. The mice received sc injections of either saline (0.1 ml/mouse), native PYY$_{3-36}$ or PYY$_{3-36}$ derivatives at the indicated doses and times within 24 h prior to the start of the 2 h re-feeding period. A minimum interval of 1 h was introduced between injection and re-feeding to avoid a stress-dependent decrease in food intake. The amount of food consumed per group was determined at the end of the feeding period. Remaining chow was weighed after the 2 h re-feeding period and the cumulative food intake per 10 mice was calculated. Values of food intake in replicate experiments were normalized according to the saline controls. Results are expressed as food intake per 10 mice±SD from 2-5 replicate experiments.

(vi) Statistical analysis. The significance of differences in food consumption was determined by the Student's t-test, using the total weight of food consumed by each group of 10 mice as a single value. A saline-injected group of 10 mice was included in each experiment as a control. A two-tailed, paired t-test was performed between the control and treated groups.

31(i) the Effect of PYY$_{3-36}$ on Food Intake in Mice

To evaluate the duration and magnitude of the effect of PYY$_{3-36}$ and its derivatives on food intake, we employed the mouse re-feeding model of 24 h starvation followed by a re-feeding period of 2 h. Initially we repeated previous studies, where PYY$_{3-36}$ was administered immediately prior to the re-feeding period. However, we found that the stress of mere handling the mice had a profound and inconsistent effect on food intake, thereby reducing the difference between saline and PYY$_{3-36}$. We then injected the mice sc 1 h prior to start of the re-feeding period and obtained a much more consistent difference between PYY$_{3-36}$ and saline. FIG. 15 shows that PYY$_{3-36}$ inhibited food intake in a dose-dependent manner. Mice receiving saline or PYY$_{3-36}$ at a dose of 5 nmol/mouse consumed 10.7±1.26 and 5.26±1.47 g chow per 10 mice, respectively (P<0.001, N=5). These figures correspond to a 50% decrease in food intake by the PYY$_{3-36}$ groups, as compared with the control saline groups. Inhibition was statistically significant at all doses used, including the lowest dose of 0.2 nmol/mouse (0.8 μg/mouse, P>0.05, N=3). The dose-response corresponded to a half maximal effect of PYY$_{3-36}$ at about 0.5 nmol/mouse (FIG. 15).

We then determined the duration of the satiety induced by sc administration of PYY$_{3-36}$ (5 nmol/mouse) at different times prior to the re-feeding period. The satiety induced by PYY$_{3-36}$ was maximal when given 1 h prior to re-feeding and rapidly decreased when PYY$_{3-36}$ was administered at earlier times. The half-life of its biological response was about 3 h and no effect was seen with 5 nmol PYY$_{3-36}$ when administered nearly 10 h prior to the re-feeding period (FIG. 16).

Intraperitoneal (rather than subcutaneous) administration of PYY$_{3-36}$ to mice has induced a considerably shorter-lived satiety effect. For example, an ip dose of 5 nmol PYY$_{3-36}$/mouse was fully effective when administered 30 min before re-feeding, but had no effect when administered 2 h before meal (not shown).

We then attempted to extend the biological activity of PYY$_{3-36}$ by conventional pegylation. Thus, mono-pegylated PYY$_{3-36}$ was prepared (see Materials and Methods above)

and tested for its biological activity by sc administration (5 nmol/mouse) 1 h prior to the re-feeding period. No significant reduction in food intake was obtained as compared with the saline control, indicating that conventional pegylation, which results in a stable pegylated peptide, abolished the biological activity of $PYY_{3-36}$ (FIG. 17).

We then tested if the inactivation of $PYY_{3-36}$ was due to the bulkiness of the PEG group or due to blocking of the amino residues of $PYY_{3-36}$. Acetylation of the two amino groups of $PYY_{3-36}$ largely abolished the effect of $PYY_{3-36}$ in inducing satiety in vivo. Thus, mice injected with 20 μg Nα-Nε-diacetyl-$PYY_{3-36}$ per mouse ate 10.54±0.08 g chow per 10 mice, as compared with 10.6±1.26 g in the saline group and 5.26±1.47 g in the $PYY_{3-36}$ group. Hence, even attachment of a small acetyl group was sufficient to disrupt the biological activity of $PYY_{3-36}$.

31(ii) Preparation and Characterization of $PEG_{40}$-FMS-$PYY_{3-36}$

The lack of biological activity following pegylation or even acetylation of $PYY_{3-36}$ prompted us to prepare the $PEG_{40}$-FMS-$PYY_{3-36}$ conjugate described in Example 23 hereinabove. This product was analyzed by mass-spectrometry to determine the ratio of $PEG_{40}$ to $PYY_{3-36}$ by MALDI-TOF MS analyses. $PYY_{3-36}$ exhibited a molecular mass of 4047.51 D (calc.=4049.6 D). $PEG_{40}$-SH had an average mass of 43,626 D, and the conjugate yielded a major peak corresponding to a molecular mass of 47,712.6 D (not shown). The calculated mass of the 1:1 conjugate of $PEG_{40}$-SH and MAL-FMS-$PYY_{3-36}$ is 48,087 D. Thus the main product corresponds to such a 1:1 conjugate.

31(iii) $PEG_{40}$-FMS is Linked to the α Amino Group of $PYY_{3-36}$

Peptide $YY_{3-36}$ contains the N-terminal α-amino group of isoleucine and one ε-amino group of lysine at position 2, both of which are potentially available for acylation by MAL-FMS-OSu. To determine the site(s) of acylation, $PEG_{40}$-FMS-$PYY_{3-36}$ was reacted with a 500 molar excess of acetic anhydride at pH 7.0 for 1 h, followed by dialysis against water overnight. The $PEG_{40}$-FMS group was then removed by incubating the acetylated $PEG_{40}$-FMS-$PYY_{3-36}$ for 4 days at pH 8.5. The product was then subjected to N-terminal protein sequence analysis. As shown in FIG. 18, cycles 1, 2 and 3 yielded the expected amounts of isoleucine, ε-acetyl lysine and proline, respectively. No free lysine was found in cycle 2. Thus, the conjugate consists of $PEG_{40}$-FMS and $PYY_{3-36}$ at a 1:1 ratio. Furthermore, based on the sequencing yields, the $PEG_{40}$-FMS group is primarily linked to the N-terminal α-amino group of $PYY_{3-36}$. Nevertheless, this analysis could not entirely exclude the presence of a $PYY_{3-36}$ mono-substituted at its ε-lysine side chain. However, in view of the complete regeneration of the native peptide, this point is of a rather minor significance.

31(iv) $PEG_{40}$-FMS-$PYY_{3-36}$ Hydrolyses to Yield $PYY_{3-36}$ Under Physiological Conditions To evaluate the rate of $PYY_{3-36}$ release from $PEG_{40}$-FMS-$PYY_{3-36}$, we incubated the conjugate in phosphate buffer (pH 8.5, 0.1 M, 37° C.). Aliquots were withdrawn at different times and subjected to analytical HPLC, using eluting conditions, which resolve $PEG_{40}$-FMS-$PYY_{3-36}$ from $PYY_{3-36}$. At pH 8.5, the rate of FMS hydrolysis from FMS-peptides or proteins is nearly identical to that obtained in normal human serum (Shechter et al., 2001). As shown in FIG. 19, $PYY_{3-36}$ was released from the conjugate in a slow, nearly homogenous fashion with a half-life of 5.3 h. After 40 h, the cumulative amount of free $PYY_{3-36}$ reached 79% of the input $PEG_{40}$-FMS-$PYY_{3-36}$.

31(v) Hydrolysis of $PEG_{40}$-FMS-$PYY_{3-36}$ in Normal Mouse Serum

We found that $PYY_{3-36}$ undergoes rapid proteolysis in normal mouse serum at 37° C. with a half-life of 3±0.7 min. (FIG. 20, insert). Therefore, the rate of $PEG_{40}$-FMS-$PYY_{3-36}$ hydrolysis was evaluated by the amount of 2-$PEG_{40}$-9-sulfo-fluorene released during hydrolysis. $PEG_{40}$-FMS-$PYY_{3-36}$ was incubated in normal mouse serum at 37° C. Aliquots were withdrawn at different times, ethanol (3 volumes) was added to precipitate serum proteins, and following centrifugation the amount of 2-$PEG_{40}$-9-sulfo-fluorene was measured in the supernatants by HPLC. As shown in FIG. 20, hydrolysis of $PEG_{40}$-FMS-$PYY_{3-36}$ in normal mouse serum at 37° C. proceeded in a nearly homogenous fashion with a half-life of 7.0±0.3 h.

31(vi) $PEG_{40}$-FMS-$PYY_{3-36}$ Induces a Prolonged Satiety in Mice

We then determined the duration of the effects of $PEG_{40}$-FMS-$PYY_{3-36}$ (5 nmol/mouse) on food intake. The half-life of the biological response of $PYY_{3-36}$ was about 3 h (FIG. 16). By comparison, the biological activity of $PEG_{40}$-FMS-$PYY_{3-36}$ was much more persistent (FIG. 21). Mice given $PEG_{40}$-FMS-$PYY_{3-36}$ 18 h prior to re-feeding ate 4.7±0.14 g chow per 10 mice, a value representing a 52% reduction in food intake as compared with the control (saline) group ($P>0.05$). A statistically significant reduction of 27% in food intake was also seen in mice given $PEG_{40}$-FMS-$PYY_{3-36}$ 24 h prior to re-feeding ($P<0.05$; FIG. 21). Thus, the half-life of the satiety effect exerted by $PEG_{40}$-FMS-$PYY_{3-36}$ was about 24 h, namely, 8-fold longer than that of unmodified $PYY_{3-36}$. In a control study, sc administration of $PEG_{40}$-FMS-Glycine ethyl ester (5 nmoles/mouse) 15 h before refeeding had no effect whatsoever on food intake as compared with saline (FIG. 21, right columns).

Example 32

Biological Activity of $(PEG_{40}$-FMS$)_2$-hGH and $PEG_{40}$-FMS-hGH

Human growth hormone (hGH) is an essential pituitary hormone which regulates growth and development of peripheral tissues. HGH is an FDA-approved drug that is widely in use for replacement therapy in growth hormone deficient children. As valid for other non-glycosylated protein drugs of molecular mass lower than 50 kDa, hGH is cleared rapidly from the circulatory system having a $t_{1/2}$ value of 20-30 min in humans. Clearance takes place primarily via the kidney. The covalent attachment of PEG chains to hGH can substantially decrease clearance by glomerular filtration via the kidneys, and therefore elongate life-time in vivo. Several PEG chains must be introduced to hGH in order to appreciably elongate its life-time in vivo. Pegylation often results in a drastic decrease in the biological or pharmacological potencies of peptides and proteins. This is especially valid for hGH owing to the relatively large surface area of site 1 and site 2 through which the hormone binds the first receptor and then the second receptor to form a homodimeric receptor complex that initiates signaling.

The covalent attachment of PEG chains to hGH in a non-reversible fashion however, leads to a drastic loss in the biological potency of this hormone. For instance, Clark et al., 1996, have linked two to seven $PEG_{5000}$ chains to the amino side chain moieties of hGH. The linkage of two $PEG_{5000}$/hGH only already led to ~90% loss in the biological potency of hGH. About five such $PEG_{5000}$ chains had to be linked to the protein for increasing circulating half-life substantially. Such $(PEG_{5000})_5$ hGH conjugates however had less than 0.1% the biological potency of hGH.

Two PEG-FMS-hGH conjugates have been prepared according to the invention (Examples 24-25). In fact, hGH contains several conjugatable amino functions. However, in view of the pegylation reaction's reversibility according to the present invention and regeneration of the native peptide and protein hormones in physiological condition, this point deserves only minor consideration.

32(i) Receptor-binding capacity of $(PEG_{40}$-FMS$)_2$-hGH and $PEG_{40}$-FMS-hGH The hGH displacement assay was performed as previously described (Tsushima et al., 1980). $(PEG_{40}$-FMS$)_2$-hGH, prepared by linking two $PEG_{40}$-FMS moieties to hGH, has an effective molecular weight of about 120 kDa and exhibits 9±2% the receptor binding potency of the native hGH. Receptor binding capacity is regenerated upon incubation at 37° C. in normal rat serum or in 0.1M phosphate buffer (pH 8.5) at 37° C. with a $t_{1/2}$ value of ~20 hrs, reaching 70-80% the native-receptor binding capacity following 50 hours of incubation (not shown).

32(ii) the Hydrolysis Rate and Reaction Order of $PEG_{40}$-FMS-hGH

The hydrolysis rate and reaction order of $PEG_{40000}$-FMS-hGH were evaluated at pH=8.5, 37° C. The release of hGH was monitored by RP-HPLC and was determined to be a first order reaction (Table 3, FIG. 22). In vitro, $PEG_{40000}$-FMS-hGH exhibits no receptor binding affinity. Upon incubation, recognition of the released hGH by the native hGH receptor was preserved (FIG. 22). Human growth hormone was released from the conjugate in a slow homogenous fashion, with $t_{1/2}$ of 11.8 h (Table 3, FIG. 23).

Example 33

$PEG_{40}$-FMS-ANP Undergoes Time-Dependent Hydrolysis at Physiological Conditions Atrial natriuretic peptide (ANP) is a 28-mer amino acid non-lysine containing peptide which exerts natriuretic, diuretic and vasorelaxant actions. It plays an important role in the body's blood volume and blood pressure homeostasis. ANP has a very high affinity for its receptor sites (10 pm), and is therefore cleared very rapidly ($t_{1/2}$~0.5 min) by receptor and protease-mediated events. ANP is therefore not suitable as a drug for subcutaneous administration for regulation of blood pressure homeostasis in humans. The covalent attachment of a $PEG_{40}$-chain to the α-amino moiety of ANP generates a conjugate which is fully devoid of receptor binding affinity (data not shown).

$PEG_{40}$-FMS-ANP, prepared by linking $PEG_{40}$-FMS to the α-amino side chain of ANP, is TNBS negative. Upon incubation at pH 8.5 and 37° C., this conjugate undergoes spontaneous hydrolysis with a $t_{1/2}$ value of 23±2 hrs, generating the parent ANP following 50 hours of incubation (Table 5). Preliminary measurements in rats in vivo revealed that SC-administered $PEG_{40}$-FMS-ANP has a 60-fold increase in serum half-life, in comparison to native ANP. The conjugate is fully protected from receptor-mediated degradation prior to the fall-off of the $PEG_{40}$-FMS chain from ANP by hydrolysis.

Example 34

An Albumin-Insulin Conjugate Releases Insulin Slowly Under Physiological Conditions The covalent linkage of peptides or protein drugs to human serum albumin (HSA) greatly prolongs their lifetime in vivo, but is pharmacologically irrelevant when irreversibly inactivates them. We retain drug bioactivity by synthesizing a heterobifunctional reagent (Mal-Fmoc-OSu: 9-hydroxymethyl-2-(amino-3-maleimidopropionate)-fluorene-N-hydroxysuccinimide) that generates HSA-Fmoc-insulin on covalent conjugation to insulin's amino group and HSA's cys-34 side chains. HSA-Fmoc-insulin is water-soluble and, upon incubation in aqueous buffers reflecting normal human serum conditions, slowly, spontaneously and homogeneously hydrolyzes to release unmodified insulin with a $t_{1/2}$ of 25±2 hrs. A single subcutaneous or intraperitoneal administration of HSA-Fmoc-insulin to diabetic rodents lowers circulating glucose levels for about 4 times longer than an equipotent dose of $Zn^{2+}$-free insulin. Following subcutaneous administration, onset of the glucose-lowering effect is delayed 0.5-1 hr and persists for 12 hrs. Thus, we present a prototype insulin formulation possessing three desirable parameters: high aqueous solubility, delayed action following subcutaneous administration and prolonged therapeutic effect.

Most polypeptide drugs, in particular nonglycosylated proteins of molecular mass less than 50 kDa, are short-lived species in vivo, having a circulatory half-life of 5-20 min. The short lifetimes of proteins in vivo are attributed to several mechanisms, including glomerular filtration in the kidney and proteolysis at several levels. Insulin is degraded primarily in the liver, through a mechanism defined as receptor-mediated endocytosis. This mechanism is an efficient route for terminating the action of the hormone after the levels of glucose and other nutrients have been normalized. Chemically modified insulins with negligible receptor binding affinities are therefore longer-lived species within the circulation, however they are biologically ineffective.

IDDM patients receive multiple daily subcutaneous administrations of 'rapid' and long-acting insulins. Prolonged long-acting insulin preparations are needed to supply low basal levels of circulating insulin between meals and overnight, this being a physiological requirement for reducing triglyceride breakdown and suppressing hepatic glucose output under 'resting' conditions.

Most long-acting insulins currently in use are suspensions of crystals, produced either by $Zn^{2+}$ ions, or by the addition of basic protamine. Such injected suspensions have decreased rates of absorption from the subcutaneous compartment to the circulatory system. Slow dissolution at the site of injection brings about the protracted effect.

In recent years, major efforts have been devoted to prolonging the action of insulins that are soluble in aqueous buffered media. In one such innovative approach, two arginine moieties were covalently linked to insulin, to raise the isoelectric point of the hormone. The derivative thus obtained is formulated in a soluble form in a slightly acidic media, and is crystallized and precipitated immediately after injection, at the physiological, neutral pH of the subcutaneous space.

Albumin is long-lived in vivo. Similarly, drugs and endogenous substances that associate tightly with albumin have lower clearance rates than do the unbound substances, and exhibit prolonged life-time profiles in vivo (Taylor and Granger, 1984). Long chain-free fatty acids bind tightly to albumin (Ka=$10^8 M^{-1}$ (Carter and Ho, 1994)), a fact that provided the impetus for preparation of soluble fatty acid acylated insulins that could bind to serum albumin. However, the affinity of the insulin conjugates for albumin (Ka~$10^5 M^{-1}$) was considerably less than that of the unbound long chain-free fatty acids and the conjugates exhibited only moderately prolonged actions in vivo (Kurtzhals et al., 1995, 1996, 1997).

A series of HSA-peptide conjugates have been recently prepared through formation of a stable covalent bond between maleiimido-derivatives of biologically active peptides (e.g. ANP (Leger et al., 2003), dynorphine (Holmes et al., 2000), or the Kringle 5 region of plasminogen (Leger et al., 2004)) and the mercapto moiety of HSA's Cys-34. This was undertaken with the aim of increasing the peptide's half-life in circulation by reducing elimination through the kidney and concomitantly protecting it from proteolysis by plasma enzymes. The activities of the HSA-bound peptides, though significantly reduced as compared to the parent peptides, were found to be rather substantial. Moreover, the conjugates proved to be long-acting species.

Therapeutically, insulin differs from many other polypeptide drugs, in the sense that overdosing may lead to severe hypoglycemia. To avoid that, only a limited dosage of insulin can be administered each time. Such a dosage is often insufficient to maintain the basal nighttime insulin level needed to avoid hyperglycemia at dawn. This therapeutic drawback can be overcome by engineering an insulin-prodrug that is biologically inactive at the time of administration.

In this example, we aim to link insulin to HSA via a covalently stable bond. We expect such a non-dissociable molecule to share albumin's longevity in vivo. As an extended surface area of the insulin molecule is engaged in receptor binding (Pullen et al., 1976), we initially thought it unlikely that such a conjugate would be biologically (and therapeutically) active. Nevertheless, even an inactive, insulin-HSA chimera could be advantageous if the conjugate is capable of generating the active unmodified parent insulin with a desirable pharmacokinetic pattern. Our efforts in this latter direction are brought here in detail.

Materials and Methods (i) Materials.

Human ($Zn^{2+}$-free) insulin was donated by Novo Nordisk (Bagsvaerd, Denmark) and by Biotechnology General (Rehovot, Israel) and was used without further purification. D-[$U^{14}$-C]Glucose (4-7 mCi/mol) was obtained from DuPont-NEN (Boston, Mass.). Collagenase, type I, (134 U/mg) was purchased from Worthington (Freehold, N.J.). 9-Fluorenylmethoxycarbonyl-N-hydroxy-succinimide (Fmoc-OSu) and di-tert-butyldicarbonate (t-Boc)$_2$O were obtained from Novabiochem (Laüfelfingen, Switzerland). MIB-NHS was obtained from Sigma-Aldrich (Rehovot, Israel). HSA was acquired from Omrix Biopharmaceutical Ltd. (Weizmann Science Park, Nes-Ziona, Israel). The protein was treated with one equivalent of dithiothretol for 20 min at pH 6.0, and then extensively dialyzed. This treatment removes any mixed disulfide form and/or any other removable protection from cysteine-34 of HSA (36). HSA prepared by this procedure contains 0.76±0.03 mol SH per mol HSA as determined with DTNB (37). All other materials used in this study were of analytical grade.

HPLC analyses were performed using a Spectra-Physics SP-8800 liquid chromatography system with an Applied Biosystems 757 variable wave length absorbance detector and a Spectra-SYSTEM and P2000 liquid chromatography system with a Spectra-SYSTEM AS100 Autosampler and Spectra-SYSTEM UV1000, all controlled by a ThermoQuest chromatography data system (ThermoQuest Inc., San Jose, Calif.). The column effluents were monitored by UV absorbance at 220 nm. Analytical reverse phase-HPLC was performed using a pre-packed Chromolith™ Performance RP-18e column (4.6×100 mm, Merck KGaA, Darmstadt, Germany). The column was eluted with a binary gradient established between solution A (0.1% TFA in $H_2O$) and solution B (0.1% TFA in acetonitrile:$H_2O$; 3:1 v/v). Preparative separations were performed with a pre-packed Vydac, RP-18 or RP-4 column (250×22 mm, Hesperia, Calif., USA).

(ii) Biological Methods and Procedures

Iodination of insulin and of HSA using [$^{125}$I] iodine was performed using the chloramine-T method (Hunter and Greenwood, 1962). Rat adipocytes were prepared from the fat pads of male Wistar rats (100-200 g) by collagenase digestion (Rodbel, 1964). Lipogenesis (during which [$U^{14}$-C] glucose was incorporated into the lipids) was performed using the procedure of Moody et al (Moody et al., 1974). Diabetes was induced by a single intravenous injection of freshly prepared streptozocin (STZ) solution (55 mg/kg body wt) as previously described (Meyerovitch et al., 1987). Rats were maintained at 24° C. under conditions of controlled lighting and were fed ad libitum. Blood samples for the analysis of blood glucose were taken from the tail veins and measured with a glucose analyzer (Beckman Instruments, Fullerton, Calif.) by the glucose oxidase method. Groups consisted of five Wistar rats weighing 170±5 g. Data are presented as means±SE.

34(i) Pharmacological Pattern of Subcutaneously Administered HSA in the Rat $^{125}$I-labeled HSA was administered subcutaneously to rats and the pharmacological pattern was constructed as a function of time by withdrawing blood aliquots at various time points and determining the TCA-precipitable counts for each aliquot. Subcutaneously administered HSA is a long-lived species in the rat circulatory system in vivo. It reached a peak value 14±1 h after administration and then declined with a t1/2 of 41±2 h (FIG. 24). For comparison, we subcutaneously administered $^{125}$I-insulin under similar experimental conditions. Insulin reached its peak value at 1±0.1 h and then declined with a t1/2 of 9.0±1.0 hrs. Thus, subcutaneously administered HSA exhibits a substantially prolonged life-time in vivo compared to insulin or any other nonglycosylated peptide or protein of molecular mass lower than 17 kDa (reviewed in Shechter et al., 2001).

34(ii) Preparation of HSA-Fmoc-Insulin

To a stirred solution of $Zn^{2+}$ free insulin (5.9 mg, 1 μmoles in 1.0 ml of 0.1M phosphate buffer at pH 7.2) was added 505 μg (1 eq) of MAL-Fmoc-OSu (50.5 μl from a fresh solution of MAL-Fmoc-OSu in DMF, 10 mg/ml). The reaction was carried out for 20 minutes at 25° C. HSA (0.37 ml from a solution of 1.6 mM) was then added to a final concentration of 0.42 mM (0.6 mol/mol insulin). The reaction was carried out for 2 hrs, and the mixture was then dialyzed overnight against $H_2O$ at 7° C. HSA-Fmoc-insulin was purified from unreacted insulin and/or from insulin-Fmoc-MAL that had not reacted with HSA by preparative HPLC (RP-4 column, Hesperia Calif. 20-100% B over 60 min with a flow rate of 10 ml/min.) The fractions corresponding to HSA-Fmoc-insulin, co-eluted with HSA, were collected and lyophilized.

34(iii) Preparation of HSA-BENZ-Insulin

This (irreversible) HSA-insulin conjugate was prepared under identical conditions to those used for HSA-Fmoc-insulin in 34(ii) above, except that the heterobifunctional agent used was MIB-NHS. The reagent (32 µl from a fresh solution of MIB-NHS at 10 mg/ml) was reacted with insulin for 20 min at 25° C., prior to the addition of HSA. HPLC-purified HSA-BENZ-insulin was characterized by MALDI-TOF MS. A mass of 72.4324 kDa was found (calculated mass for 1:1 conjugate is 72.570 kDa).

34(iv) Engineering an HSA-Insulin Conjugate that Releases Insulin Under Physiological Conditions As described in 34(iii) above, the covalent linking of insulin to HSA with MIB-NHS resulted in a non-dissociable HSA-insulin conjugate having negligible biological potencies in vitro. We therefore the heterobifunctional agent MAL-Fmoc-OSu (Precursor 7), consisting of an Fmoc-OSu derivative in which a maleimide group is attached to the fluorenyl backbone. Using MAL-Fmoc-OSu enabled us to link proteins via their amino side chains to the single cysteinyl residue of HSA. Previously, we have found that Fmoc moieties, linked to the amino side chains of peptides and proteins, undergo slow hydrolysis in aqueous solutions under physiological conditions, generating the unmodified parent peptides and proteins (Shechter et al., 2001; Gershonov et al., 1999).

The procedure described in detail in 34(ii) above was found optimal for coupling equimolar amounts of insulin to HSA. In brief, MAL-Fmoc-OSu is first reacted stoichiometrically with insulin for 20 min at pH 7.2, this being a pH value at which MAL remains chemically stable for several hours (Hazum et al., 1992). Albumin is then added with a stoichiometry of 0.6 mol per mol derivatized insulin to ensure quantitative coupling of insulin-Fmoc-MAL to the cysteinyl-34 of this carrier protein. Unreacted insulin and/or insulin-Fmoc-MAL are removed by a semi-preparative HPLC procedure.

34(v) General Features of HSA-Fmoc-Insulin

Table 6 summarizes several characteristic features of the HPLC-purified HSA-Fmoc-insulin we prepared. It is a highly water-soluble derivative (>200 mg/ml) in buffered near-neutral solutions (pH 6-7) owing to the extreme solubility of the carrier protein (Peters, 1996). MALDI-TOF MS analysis revealed a molecular mass of 73.189 kDa (calculated mass for the 1:1 conjugate is 73.250 kDa). Analytical HPLC revealed that HSA-Fmoc-insulin co-emerges with HSA as a single symmetric peak (FIG. 25; retention time 8.1 min). A molar extinction coefficient of $\epsilon 280=54,400$ ($\epsilon_{280}^{0.1\%}0.743$) was found (calculated for 1:1 conjugate $\epsilon 280=62,285$). The HSA-Fmoc-insulin thus obtained contains 24±3 µg covalently linked insulin per mg HSA as judged by HPLC analysis following the release of the covalently linked insulin from the conjugate by incubation at pH 10.3 for 4 hrs at 25° C. (FIG. 25).

34(vi) Biological Potency of HSA-Fmoc-Insulin

FIG. 26 shows the dose-response curve for native insulin and for HSA-Fmoc-insulin in a lipogenic assay in rat adipocytes. Based on the value of 24±3 µg covalently linked insulin per mg HSA in the conjugate (Table 6), HSA-Fmoc-insulin has 12±3% the biological potency of the native hormone (ED50 value=2.5±0.1 ng/ml versus $ED_{50}=0.3\pm0.01$ ng/ml for insulin, FIG. 26). The covalent linking of insulin to HSA, using the non-reversible agent MIB-NHS under similar experimental conditions (see Methods), yielded a conjugate having negligible potency ($ED_{50}=130\pm10$ ng/ml, being ~0.2% of the biological potency of insulin).

34(vii) HSA-Fmoc-Insulin Releases Insulin Upon Incubation Under Physiological Conditions Incubation of HSA-Fmoc-insulin at pH 10.3 for 4 hrs at 25° C. causes the covalently linked insulin to be released quantitatively from the conjugate (FIG. 25B). In FIG. 27A, HSA-Fmoc-insulin was incubated in 0.1M phosphate buffer (pH 8.5, 37° C.) and the amount of insulin released from the conjugate as a function of time was quantified by HPLC analysis. At pH 8.5 the rate of Fmoc hydrolysis from Fmoc-protein conjugates is nearly identical to that obtained in normal human serum at 37° C. (Shechter et al., 2001; Gershonov et al., 1999). As shown in FIG. 27A, insulin is released from the conjugate in a slow homogenous fashion, having a half-life of 24±3 hrs. After 80 hrs and 150 hrs the cumulative amount of free insulin reached 71% and 100%, respectively, of the initial HSA-Fmoc-insulin level.

34(viii) Reactivation of HSA-Fmoc-Insulin Upon Incubation

In FIG. 27B, aliquots were withdrawn from incubated HSA-Fmoc-insulin (pH 8.5, 37° C.) at different time points and analyzed for their biological potencies in a lipogenic assay in rat adipocytes. As shown in FIG. 27B, the conjugate undergoes reactivation upon incubation in a nearly linear fashion. Thus, starting from 12±3% at time 0, lipogenic potency is elevated to 31±3%, 43±4% and 59±5% following 10 hrs, 20 hrs and 40 hrs of incubation, respectively. Upon 150 hr of incubation, HSA-Fmoc-insulin regains its full biological potency (FIG. 27B).

34(ix) a Single Intraperitoneal or Subcutaneous Administration of HSA-Fmoc-Insulin Facilitates a Prolonged Glucose-Lowering Pattern in Mice In FIG. 28, we compare the glucose-lowering pattern of HSA-Fmoc-insulin (0.4 mg/mouse, corresponding to 9.6 µg covalently linked insulin) to that of $Zn^{2+}$-free insulin (3 µg/mouse), following a single administration. For FIG. 28A, administration was intraperitoneal, while in FIG. 28B it was subcutaneous. As shown in FIG. 28A, HSA-Fmoc-insulin facilitates a prolonged and stable glucose-lowering pattern over a period of 14 hrs, exceeding by about 4 times the duration obtained by the native hormone. Nearly the same glucose lowering patterns were obtained following subcutaneous administration (FIG. 28B). Again, the conjugate produced a prolonged and stable glucose-lowering pattern over many hours. A noticeable difference, however, is a delay of about 0.5 hrs until the fall in glucose level following subcutaneous administration of the conjugate commences (FIG. 28B). This suggests that the rate of conjugate diffusion from the subcutaneous compartment into the circulatory system is considerably slower than that from the peritoneum. Indeed, diffusion and transportation rates of subcutaneously administered proteins across capillary membranes are known to decrease in proportion with increasing size of atomic radius (Taylor and Granger, 1984; Eisenberg and Crothers, 1979).

34(x) Glucose-Lowering Pattern of HSA-Fmoc-Insulin in STZ-Rats

FIG. 29 shows the glucose-lowering pattern of the conjugate after a single subcutaneous administration in streptozocin-treated hyperglycemic rats. Here we have compared a conjugate dose (7 mg/STZ-rat) that is equipotent to the administered dose of $Zn^{2+}$-free insulin (20 µg/STZ-rat) at the time of administration. The dosage calculation was based on 24±3 µg of covalently linked insulin per mg HSA having 12% of the biological potency of the free hormone (Table 6, FIG. 26). As shown in FIG. 29, HSA-Fmoc-insulin's glucose lowering effect is about 2.6 times greater than that of the native hormone. A small decrease is seen shortly after administration (i.e. at 0.5 hrs). Circulating glucose levels then fall gradually, reaching a maximal decrease at 2-3 hrs after administration (190±20 mg/dl). Hyperglycemia then reoccurs ($t_{1/2}$=5.7 hrs). The area under the curve of the saline treated group, following HSA-Fmoc-insulin administration exceeds, by about four times, comparing to that obtained with native hormone (integrated from FIG. 29). Thus, HSA-Fmoc-insulin is considerably more effective than insulin in lowering circulating glucose levels in insulin-deficient diabetic rats.

Discussion

Long fatty-acid acylated insulins that are noncovalently associated with albumin, even with moderate affinity ($Ka=10^5 M^{-1}$), are long-acting species in vivo (Kurtzhals et al., 1995, 1996). We wondered whether this would be equally valid if an insulin molecule were to be covalently linked to the carrier protein, particularly since HSA-peptide conjugates have been found to retain substantial parent-peptide activity (Leger et al., 2003, 2004; Holmes et al., 2000). Since the linkage of insulin to HSA through the non-reversible linker MIB-NHS yielded an inactive conjugate (HSA-BENZ-insulin, see Example 34(iii) above), we used the Fmoc-containing heterobifunctional reagent MAL-Fmoc-OSu. This development enabled us to link insulin (and potentially any other peptide or protein drug) via its amino groups to cysteine-34 of HSA. In previous studies we found that Fmoc moieties linked to proteins are detached in a slow and spontaneous fashion under aqueous physiological conditions generating the unmodified parental proteins. The rate of Fmoc hydrolysis is dictated exclusively by the pH, temperature and protein concentration of the serum, three parameters that are maintained in mammals in strict homeostasis. We therefore anticipated that HSA-Fmoc-insulin will yield insulin in a rather similar manner.

HSA-Fmoc-insulin is an extremely water-soluble conjugate in which insulin has about 12% the biological potency of the native hormone (FIG. 26), in lipogenesis assay. We had expected it to have negligible activity, given that an extended surface area of the insulin molecule is required for receptor binding. This activity, however, may stem from release of insulin from its conjugate during the assay, i.e. incubation for 2 hr at 37° C. in the presence of 20 mg/ml BSA. Indeed, such an explanation would be consistent with the inactivity of the stable covalent conjugate HSA-BENZ-insulin. Yet, upon incubation in aqueous solutions (i.e. pH 8.5, 37° C.) the covalently linked insulin is released from the HSA-Fmoc-insulin conjugate in a nearly homogenous fashion over a prolonged period (t1/2=24±3 hrs) with the concomitant regeneration of insulin possessing full biological potency (FIGS. 27A, 27B). HSA-Fmoc-insulin facilitates prolonged glucose lowering patterns in mice and in STZ-rats following a single subcutaneous or intraperitoneal administration. Based on administering equipotent doses of insulin and of the conjugate at time 0, the glucose lowering potency of HSA-Fmoc-insulin exceeds 3-4 times that facilitated by insulin in terms of longevity as well as efficacy (FIGS. 28A, 28B, 29).

REFERENCES

Adrian T E, Ferri G L, Bacarese-Hamilton A J, Fuessl H S, Polak J M, Bloom S R: Human distribution and release of a putative new gut hormone, peptide YY. *Gastroenterol.* 89:1070-1077 (1985).

Bailon, P. & Berthold, W. Poly(ethylene glycol)-conjugated pharmaceutical proteins. *Pharm. Sci. Technol. Today* 1, 352-356 (1996).

Bailon P, Palleroni A, Schaffer C. A., Spence C. L., Fung W-J, Porter J. E., Ehrlich G. K., Pan W, Xu Z. X., Modi M. W., Farid A, Berthold W and Graves M. Rational design of a potent, long-lasting form of interferon: a 40 kDa branched polyethylene glycol-conjugated interferon alpha-2a for the treatment of hepatitis C. *Bioconjug Chem* 12: 195-202 (2001).

Baker, D. E. Pegylated interferon plus ribavirin for the treatment of chronic hepatitis C. *Rev. Gastroenterol. Disord.* 3, 93-109 (2003).

Batterham R L, Cowley M A, Small C J, Herzog H, Cohen M A, Dakin C L, Wren A M, Brynes A E, Low M J, Ghatei M A, Cone R D, Bloom S R: Gut hormone $PYY_{3-36}$ physiologically inhibits food intake. *Nature* 418:650-654 (2002).

Batterham R L, Cohen M A, Ellis S M, Le Roux C W, Withers D J, Frost G S, Ghatei M A, Bloom S R: Inhibition of food intake in obese subjects by peptide YY3-36. *N Engl J Med* 349:941-948 (2003).

Broberger C, Landry M, Wong H, Walsh J N, Hokfelt T: Subtypes of Y1 and Y2 of the neuropeptide Y receptor are respectively expressed in pro-opiomelanocorin and neuropeptide-Y containing neurons of the rat hypothalamic arcuate nucleus. *Neuroendocrinol.* 66:393-408 (1997).

Carter, D. C. &. Ho, J. X. Structure of serum albumin. Adv. Protein Chem. 45, 153-203 (1994).

Clark R. et al., Long-acting growth hormones produced by conjugation with polyethylene glycol. *J Biol Chem* 271, 21969-77 (1996).

Cutrone, E. C. and Langer, J. A. Identification of critical residues in bovine IFNAR-1 responsible for interferon binding. *J. Biol. Chem.* 276, 17140-48 (2001).

Delgado, C., Francis, G. E. & Derek, F. F. The uses and properties of PEG-linked proteins. *Critical Rev. Ther. Drug Carrier Syst.* 9, 249-304 (1992).

Eisenberg, D. & Crothers, D. Physicochemical Chemistry with Aapplications to the Life Sciences. 700-745 (Benjamin Cummings, Menlo Park, Calif., 1979).

Ellman, G. A colorimetric method for determining low concentrations of mercaptans. Arch. Biochem. Biophys. 74, 443-450 (1958).

Eng. J., Kleinman, W. A., Singh, L., Singh, G., Raufman, J. P. Isolation and characterization of exendin-4, an exendin 3 analogue for *heloderma suspectum* venom: further evidence for an exendin receptor on dispersed acini from guinea pig pancreas. *J. Biol. Chem.* 267, 7402-7405 (1992).

Fehmann, H. C., Jiang, J., Schweinfurth, J., Wheeler, M. A., Boyd, A. E., Göke, B. Stable expression of the rat GLP-I receptor in CHO cells activation and binding characteristics utilizing GLP-(7-36)-amide, oxyntomodulin, exendin-4, and exendin-(9-39). *Peptides* 15, 453-456 (1994).

Fuerteges, F. and Abuchowski, A. The clinical efficacy of poly(ethylene glycol)-modified proteins. *J. Controlled Release* 11, 139-148 (1990).

Fung, W-J., Porter, J. E. & Bailon, P. Strategies for the preparation and characterization of polyethylene glycol (PEG) conjugated pharmaceutical proteins. *Polymer Preprints* 38, 565-566 (1997).

Gershonov, E., Shechter, Y. & Fridkin, M. New concept for long-acting insulin, spontaneous conversion of an inactive modified insulin to the active hormone in circulation: 9-fluorenylmethyloxycarbonyl derivative of insulin. *Diabetes* 48, 1437-1442 (1999).

Gershonov, E., Goldwaser, I., Fridkin, M. & Shechter, Y. A novel approach for a water-soluble long-acting insulin prodrug: Design, preparation, and analysis of [(2-sulfo)-9-fluorenylmethyloxycarbonyl]$_3$-insulin. *J. Med. Chem.* 43, 2530-2537 (2000).

Glue, P., Fang, J. W., Rouzier-Panis, R., Raffanel, C., Sabo, R., Gupta, S. K., Salfi, M. and Jacobs, S. Pegylated interferon-alpha2b: pharmacokinetics, pharmacodynamics, safety, and preliminary efficacy data. Hepatitis C Intervention Therapy Group. *Clin. Pharmacol. Ther.* 68, 556-567 (2000).

Göke, R., Fehmann, H. C., Linn, T., Schmidt, H., Krause, M. Exendin-4 is a high potency agonist and truncated exendin-(9-39)-amide an antagonist at the glucagon-like peptide 1-(7-36)-amide receptor of insulin-secreting β-cells. *J. Biol. Chem.* 268, 19650-19655 (1993).

Goodman, L. S., and Gilman, A. G. (2001) *The Pharmacological Basis of Therapeutics* (Goodman, L. S., Gilman, A. G., Limbird, L. E., and Hardman, J. G. Eds.) 9$^{th}$ ed., pp. 1211-1213, The McGraw-Hill Company, New York.

Grandt D, Schimiczek M, Belinger C, Layer P, Goebell H, Eysselein V E, Reeve J R J: Two molecular forms of peptide YY (PYY) are abundant in human blood: characterization of a radioimmunoassay recognizing PYY 1-36 and PYY 3-36. *Regul. Pept.* 51:151-159 (1994).

Greenwald R. B., Pendri A, Conover C. D., Zhao H, Choe Y. H., Martinez A, Shum K, Guan S. Drug delivery systems employing 1,4- or 1,6-elimination: poly(ethylene glycol) prodrugs of amine-containing compounds. *J. Med. Chem.* 42, 3657-3667 (1999).

Greenwald, R. B., Choe, Y. H., Conover, C. D., Shum, K., Wu, D., & Royzen, M., Drug delivery systems based on trimethyl lock lactonization: poly(ethylene glycol) prodrugs of amino-containing compounds. *J. Med. Chem.* 43, 475-487 (2000)

Hartley, R. W., Peterson, E. A. & Sober, H. A. The relation of free sulfhydryl groups to chromatographic heterogeneity and polymerization of bovine plasma albumin. Biochemistry 1, 60-68 (1962).

Hazum, E., Shisheva, A. & Shechter, Y. Preparation and application of radioiodinated sulfhydryl reagents for the covalent labeling of SH-proteins present in minute quantities. J. Biochem. Biophys. Methods 24, 95-106 (1992).

Holmes, D. L. et al. Site specific 1:1 opioid:albumin conjugate with in vitro activity and long in vivo duration. Bioconjug. Chem. 11, 439-444 (2000).

Hunter, W. M. & Greenwood, F. C. Preparation of iodine-131 labeled human growth hormone of high specific activity. Nature (London) 194, 495-496 (1962).

Kalra S P, Dube M G, Pu S, Xu B, Horvath T L, Kalra P S: Interacting appetite-regulating pathways in the hypothalamic regulation of body weight. *Endocr. Rev.* 20:68-100 (1999).

Katre, N. V. The conjugation of proteins with poly(ethylene glycol) and other polymers: altering properties to enhance their therapeutic potential. *Adv. Drug. Delivery Sys.* 10, 91-114 (1993).

Kurtzhals, P. et al. Correlations of receptor binding and metabolic and mitogenic potencies of insulin analogs designed for clinical use. Diabetes 49, 999-1005 (2000).

Kurtzhals, P. et al. Albumin binding of insulins acylated with fatty acids: Characterization of the ligand-protein interaction and correlation between binding affinity and timing of the insulin effect in vivo. Biochemical J. 312, 725-731 (1995).

Kurtzhals, P. et al. Albumin binding and time action of acylated insulins in various species. J. Pharmaceut. Sci. 85, 304-308 (1996).

Kurtzhals, P., Havelund, S., Jonassen, I. B. & Markussen, J. Effect of fatty acids and selected drugs on the albumin binding of a long-acting, acylated insulin analogue. J. Pharmaceut. Sci. 86, 1365-1368 (1997).

Leger, R. et al. Synthesis and in vitro analysis of atrial natriuretic peptide-albumin conjugates. Bioorg. Med. Chem. Lett. 13, 3571-3575 (2003).

Leger, R. et al. Kringle 5 peptide-albumin conjugates with anti-migratory activity. Bioorg. Med. Chem. Lett. 14, 841-845 (2004).

Lee S, Greenwald R. B., McGuire J, Yang K, Shi C. Drug delivery systems employing 1,6-elimination: releasable poly(ethylene glycol) conjugates of proteins. *Bioconjugate Chemistry* 12, 163-169 (2001).

Meyerovitch, J., Farfel, Z., Zack, J. & Shechter, Y. Oral administration of vanadate ions, normalizes blood glucose level of streptozotocin treated rats, general characterization and mode of action. J. Biol. Chem. 262, 6658-6662 (1987).

Moody A J, Stan M A, Stan M, Gliemann J. A simple free fat cell bioassay for insulin. *Horm Metab Res.* 6(1):12-16 (1974).

Nucci, M. L., Shorr, R. & Abuchowski, A. The therapeutic value of poly(ethylene glycol)-modified proteins. *Adv. Drug Delivery Rev.* 6, 133-151 (1991).

O'Kelly, P., Thomsen, L., Tilles, J. G. and Cesario, T. Inactivation of interferon by serum and synovial fluids. *Proc. Soc. Exp. Biol. Med.* 178, 407-411 (1985).

Pedersen-Bjergaard U, Host U, Kelbaek H, Schifter S, Rehfeld J F, Faber J, Christensen N J: Influence of meal composition on postprandial peripheral plasma concentrations of vasoactive peptides in man. *Scand. J. Clin. Lab. Invest.* 56:497-503 (1996).

Peters, T. J. The albumin molecule: Its structure and chemical properties. in All about albumin, Biochemistry, Genetics and medical applications. (editor Peters, T.) 24-54 (Academic Press, Inc., San Diego, 1996).

Piehler, J. and Schreiber, G. Biophysical analysis of the interaction of human ifnar2 expressed in *E. coli* with IFNalpha2. *J. Mol. Biol.* 289, 57-67 (1999).

Piehler, J. and Schreiber, G. Fast transient cytokine-receptor interactions monitored in real time by reflectometric interference spectroscopy. *Anal. Biochem.* 289, 173-186 (2001).

Pullen, R. A. et al. Receptor-binding region of insulin. *Nature* 259, 369-373 (1976).

Reddy, K. R. Controlled-release, pegylation, liposomal formulations: New mechanisms in the delivery of injectable drugs. *The Annals of Pharmacotherapy* 34, 915-923 (2000).

Reddy R. K., Modi M. W. and Pedder S. Use of peginterferon alfa-2a (40 KD) (Pegasys) for the treatment of hepatitis C. *Adv Drug Delivery Rev* 54, 571-586 (2002).

Roberts, M. J., Bentley, M. D. & Harris, J. M., Chemistry for peptide and protein PEGylation. *Adv Drug Deliv Rev.* 54: 459-476 (2002).

Rodbell M. Metabolism of isolated fat cells. I. Effects of hormones on glucose metabolism and lipolysis. *J Biol Chem* 239: 375-380 (1964).

Romerio, F., Riva, A. and Zella, D. Interferon-alpha2b reduces phosphorylation and activity of MEK and ERK through a Ras/Raf-independent mechanism. *Br. J. Cancer* 83, 532-538 (2000).

Rostaing, L., Chatelut, E., Payen, J. L., Izopet, J., Thalamas, C., Ton-That, H., Pascal, J. P., Durand, D. and Canal, P. Pharmacokinetics of alphaIFN-2b in chronic hepatitis C virus patients undergoing chronic hemodialysis or with normal renal function: clinical implications. *J. Am. Soc. Nephro.* 9, 2344-2348 (1998).

Rubinstein, S., Familletti, P. C. and Pestka, S. (1981) Convenient assay for interferons. *J. Virol.* 37, 755-758.

Schepp, W., Schmidtler, J., Riedel, J., Dehne, K., Schusdziarra, V., Hoist, J. J. Exendin-4 and exendin-(9-39)NH2 agonist and antagonist, respectively, at the rat parietal cell receptor for glucagon-like peptide-1-(7-36)NH2. *Eur. J. Pharmacol.* 269, 183-191 (1994).

Schwartz M W, Morton G J: Obesity: keeping hungar at bay. *Nature* 418:595-597 (2002).

Schwartz M W, Woods S C, Porte D J, Seeley R J, Baskin D G: Central nervous system control of food intake. *Nature* 404:661-67 (2000).

Shechter, Y., Goldwaser, I., Lavon, I., Gershonov, E., Mester, B., Mironchik, M., Patt, L. P. and Fridkin, M. A new approach for prolonging the half-life of peptides, proteins and low-molecular-weight drugs in vivo. *Drugs of the Future* 26, 669-676 (2001).

Shechter, Y., Patt, L. P., Schreiber, G. and Fridkin, M. Prolonging the half-life of human interferon-alpha 2 in circulation: Design, preparation, and analysis of (2-sulfo-9-fluorenylmethoxycarbonyl)7-interferon-alpha 2. *Proc. Natl. Acad. Sci. USA* 98, 1212-1217 (2001a).

Shechter, Y., Tsubery, H. and Fridkin, M. N-[(2-Sulfo)-9-fluorenyl-methoxycarbonyl](3)-gentamicin C(1) is a long-acting prodrug derivative. *J. Med. Chem.* 45, 4264-4270 (2002).

Shechter, Y., Tsubery, H. and Fridkin, M. [2-Sulfo-9-fluorenyl-methoxycarbonyl]3-exendin-4-a long-acting glucose-lowering prodrug. *Biochem. Biophys. Res. Commun.* 305, 386-391 (2003).

Tsushima, T., Sasaki, N., Imai, Y., Matsuzaki, F., Friesen H. G. Characteristics of solubilized human-somatotropin-binding protein from the liver of pregnant rabbits *Biochem J.* 187 479-492 (1980).

Veronese, F. M. Peptide and protein PEGylation: A review of problems and solutions. *Biomaterials* 22, 405-417 (2001).

Working, P. K., et al., Safety of poly(ethylene glycol) and poly(ethylene glycol) derivatives. In: J. M. Harris and S. Zalipsky, Editors, Poly(ethylene glycol) Chemistry and Biological Applications, ACS Books, Washington, D.C. (1997), pp. 45-57.

Zalipsky S, Qazen M, Walker J. A. 2nd, Mullah N, Quinn Y. P., Huang S. K. New detachable poly(ethylene glycol) conjugates: cysteine-cleavable lipopolymers regenerating natural phospholipid, diacyl phosphatidylethanolamine. *Bioconjugate Chemistry* 10, 703-707 (1999).

TABLE 1

Chemical features of MAL-FMS-NHS

| Characteristic | Numerical value |
|---|---|
| Solubility in aqueous buffer (pH 7.2) | >10 mg/ml |
| Mass spectra data[a] | |
| Calculated ESMS | 583 Da |
| Found ESMS for [M + H]+ | 584.52 Da |
| Found ESMS for [M + Na]+ | 606.47 Da |
| Retention time (analytical HPLC)[b] | 2.65 min |
| Molar extinction coefficient at 280 nm[c] | 21,200 ± 200 mole$^{-1}$cm$^{-1}$ |
| Molar extinction coefficient at 320 nm[c] | 16,100 ± 150 mole$^{-1}$cm$^{-1}$ |

[a]Mass spectra were determined using the electrospray ionization technique
[b]The HPLC column used is a Chromolith column; (C$_{18}$); linear gradient of 10-100% of solvent B (3 ml/min).
[c]Based on the absorbance at 280 and 301 nm in PBS, pH 7.2, with compound concentration determined by quantitating the MAL-function with excess GSH and DTNB.

TABLE 2

Chemical features of PEG$_{40}$-FMS-IFNα2

| Characteristic[a] | Numerical Value |
|---|---|
| Absorbance at 280 nm[b,c] | $\epsilon_{280}$ = 39270 ± 100 |
| Mass spectra[d] | |
| PEG-FMS-IFNα2[e], calculated | 63569 daltons |
| PEG-FMS-IFNα2[e], measured | 63540 daltons |
| Retention time (analytical HPLC)[f] | 43 ± 0.5 min. |
| Solubility in aqueous buffer, pH 7.4 | >20 mg/ml |

[a]For characterization, IFNα2-FMS-MAL was dialyzed against H$_2$O prior to linking PEG$_{40}$-SH. The final product was filtered through a centricon having a cut-off value of 50 kDa. These procedures remove free MAL-FMS-NHS and any residual native IFNα2, or IFNα2-FMS-MAL that has not been linked to PEG$_{40}$-SH.
[b]Determined by UV spectroscopy. Derivative concentration was determined by acid hydrolysis of a 20 µl aliquot followed by amino acid analysis, calculated according to aspartic acid (14 residues), alanine (9 residues) and isoleucine (8 residues).
[c]Native IFNα2 absorbs at 280 nm with $\epsilon_{280}$ = 18070 (30).
[d]Mass spectra were determined by using MALDI-TOF mass spectroscopy.
[e]Calculated mass is obtained by the additive masses found for native IFNα2 (19278 daltons); for PEG$_{40}$-SH (43818 daltons) and for the spacer molecule following conjugation (473 daltons).
[f]Native IFNα2 elutes under identical analytical HPLC procedure with retention time = 33.9 min.

TABLE 3

Structures and half-life time of PEG-FMS conjugates.

| | Structure | k (h$^{-1}$)[b] | t$_{1/2}$ (h)[c] |
|---|---|---|---|
| Mal-FMS-Peptide 27[a] | 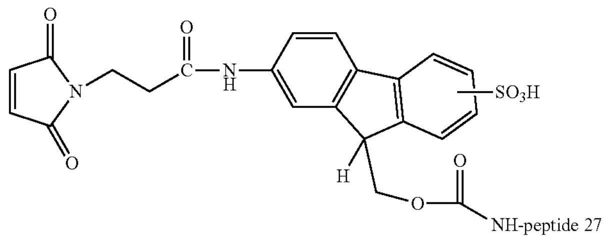 | 0.082 | 8.4 |
| PEG$_{40000}$-FMS-exendin-4 [d] | 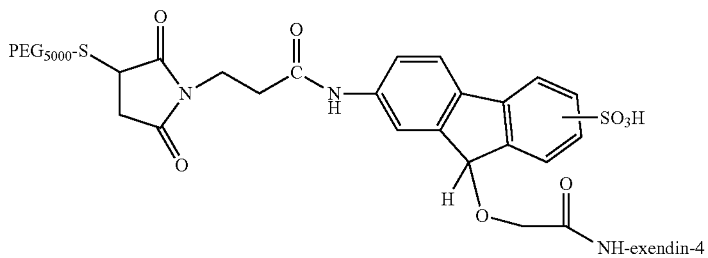 | 0.058 | 11.9 |
| PEG$_{5000}$-FMS-exendin-4 | 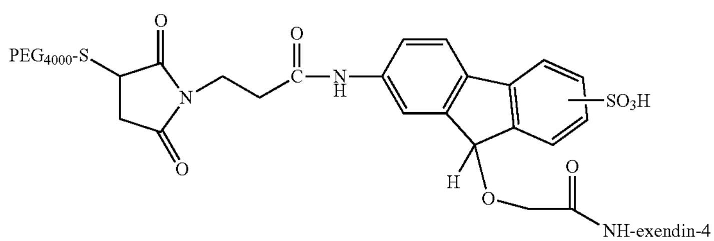 | 0.050 | 13.8 |
| PEG$_{5000}$-FMS-4-nitro-phenethylamine | 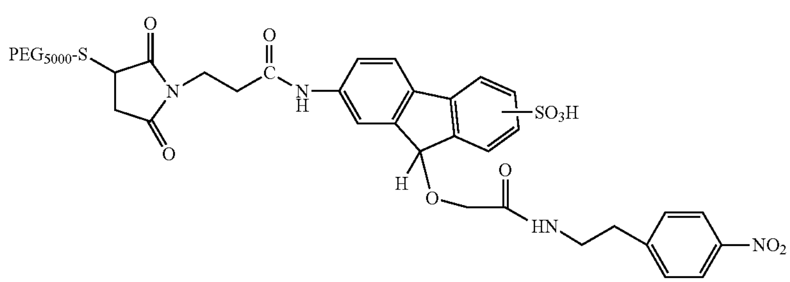 | 0.074 | 9.4 |
| PEG$_{40000}$-FMS-human growth hormone (hGH) [d] | 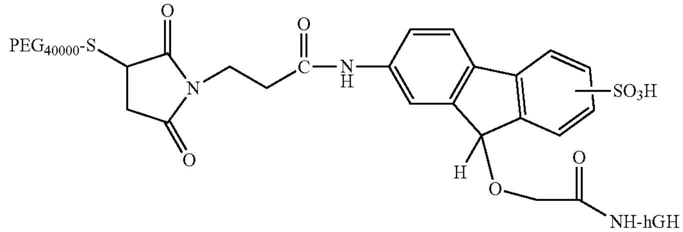 | 0.059 | 11.8 |

[a] Rate of hydrolysis was followed by trinitrobenzene sulfonic acid assay
[b] k is the slope constant derived from the plot of ln [PEG-FMS conjugate] against time (h)
[c] t$_{1/2}$ was determined from the formula t$_{1/2}$ = ln2/k.
[d] plot of hydrolysis can be found as FIG. 23.

TABLE 4

Receptor binding capacity of mono- and bis-PEG-FMS-IFN-α2 conjugates prior to, and following, incubation with ifnar-2-EC.

| Derivative designation | Mole PEG$_{40}$-FMS per mole IFNα2 | Receptor binding capacity[a] % | Receptor binding capacity following 50 h of incubation at pH 8.5, 37° C. %[b] | t$_{1/2}$ of regenerating receptor binding capacity (h) |
|---|---|---|---|---|
| Native IFNα2 | — | 100 | 97 ± 2 | — |
| (PEG$_{40}$-FMS)$_1$-IFNα2 | 1.0 | 9 ± 1 | 95 ± 4 | 9 ± 1 |
| (PEG$_{40}$-FMS)$_2$-IFNα2 | 1.9 | 0.4 ± 0.05 | 92 ± 3 | 24 ± 3 |

[a]Receptor binding capacity toward immobilized ifnar-2-EC was assessed by the reflectometric interference spectroscopy procedure-RIFS.
[b]Incubation was performed in 0.1M phosphate buffer pH 8.5, containing 0.5% BSA.

TABLE 5

Rate of hydrolysis of PEG$_{40}$-FMS-ANP at pH 8.5, 37° C.

| Time of Incubation (pH 8.5, 37° C.) hours | % hydrolyzed |
|---|---|
| 0 | 0 |
| 3 | 7 |
| 6 | 18 |
| 10 | 27 |
| 15 | 40 |
| 23 | 50 |
| 33 | 75 |
| 43 | 87 |
| 50 | 100 |

TABLE 6

Chemophysical features of HSA-Fmoc-insulin

| | | |
|---|---|---|
| Covalently-linked insulin[a] | | 24 ± 3 μg/mg HSA |
| Solubility in aqueous buffer (pH 7.0) | | >200 mg/ml |
| HPLC analysis retention time[a] | | 8.1 min |
| MALDI-TOF Mass Spectrum analysis[b] (m/z) | Calculated | 73.250 kDa |
| | Found | 73.189 kDa |
| Molar extinction coefficient | Calculated[c] | $\epsilon_{280}$ = 62,285 |
| | Found | $\epsilon_{280}$ = 54,400 Error! Bookmark not defined. |
| | | $\epsilon_{280}^{0.1\%}$ = 0.744 |

[a]Determined by HPLC analysis following incubation of the conjugate in 0.1M Na2CO3 (pH 10.3) for 4 h at 25° C. Analytical HPLC procedures were carried out under the experimental conditions specified in the legend to FIG. 25. Under these conditions, insulin elutes with Rt = 6.91 min and has a surface area of 187,000 ± 9000 mav/μg insulin and HSA (either free or linked to insulin) elutes with Rt = 8.1 min and has a surface area of 156,000 ± 7000 mav/μg HSA.
[b]MALDI-TOF MS analyses were carried out with the Bruker-Reflex-Reflection model.
[c]Molar extinction coefficient for HSA-Fmoc-insulin was calculated by combining the ε280 values of HSA (ε280 = 35,280, ref. 37), insulin (ε280 = 5800) and Fmoc (ε280 = 10,250).

Scheme 1: Precursors 1-4

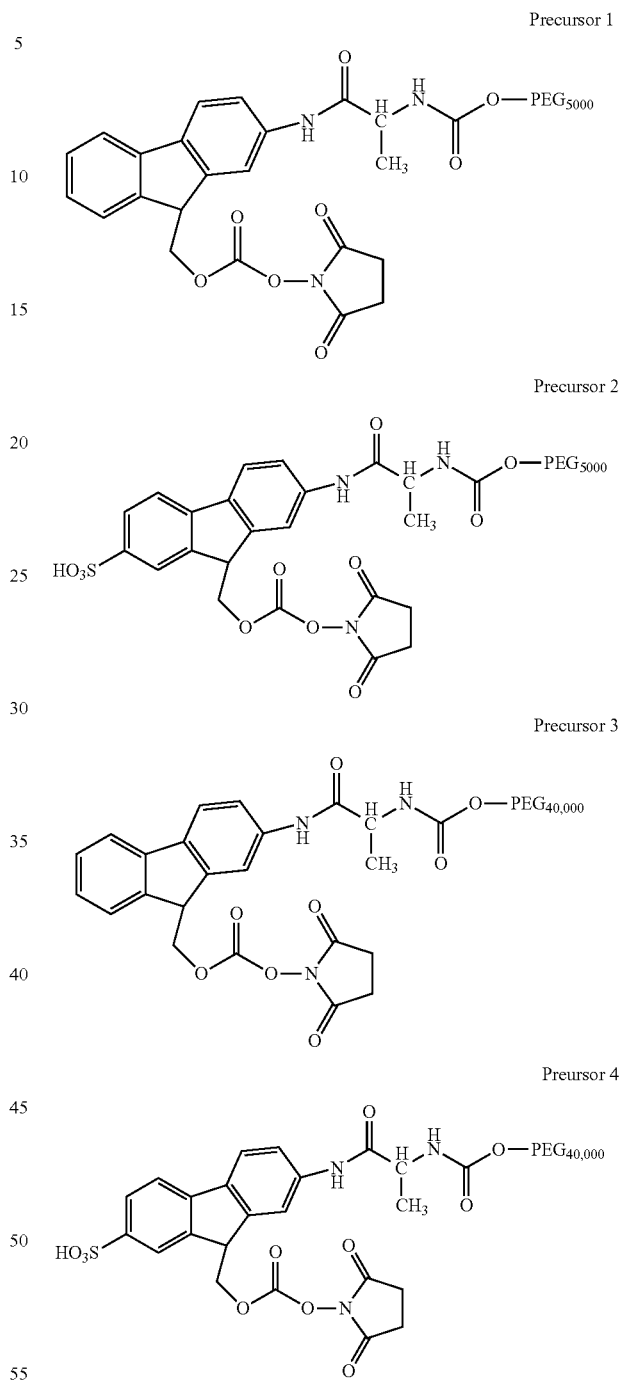

Scheme 2: Synthesis of Precursors 1-4

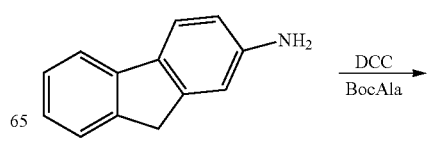

71
-continued
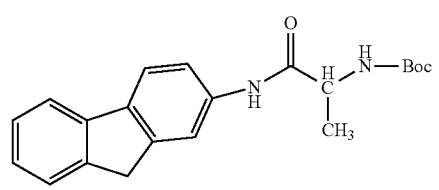
Intermediate a
NaH
Ethyl formate →
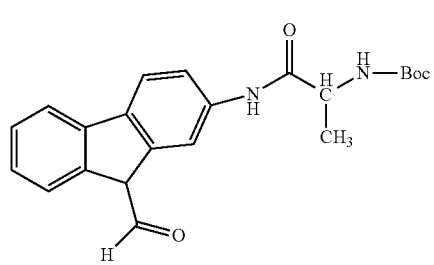
Intermediate b
NaBH₄ →
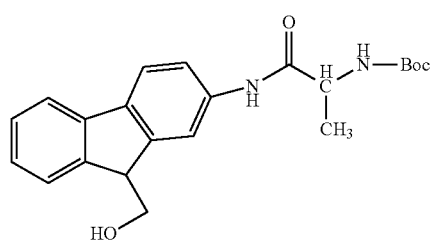
Intermediate c
THF →
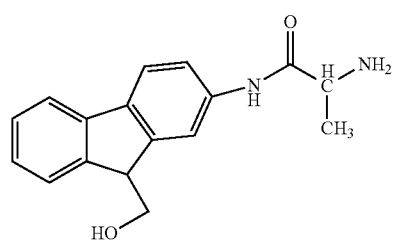
Intermediate d
PEG—OSu →
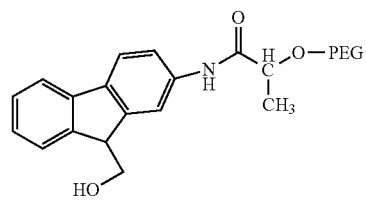
Intermediate e
Triphosgene
N-hydroxysuccinimide →
72
-continued
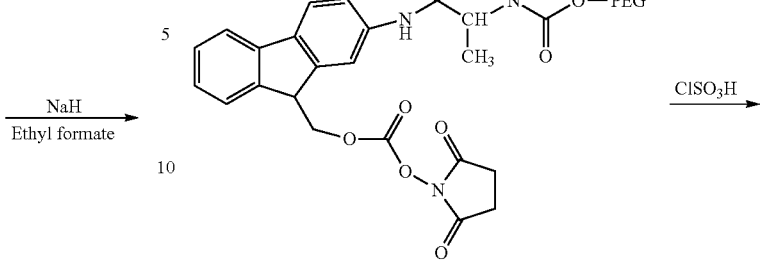
Precursor 1 (PEG₅,₀₀₀)
Precursor 3 (PEG₄₀,₀₀₀)
ClSO₃H →
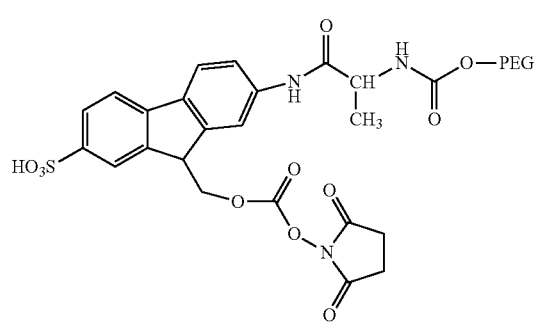
Precursor 2 (PEG₅,₀₀₀)
Precursor 4 (PEG₄₀,₀₀₀)
Scheme 3: Precursors 5-8
Precursor 5
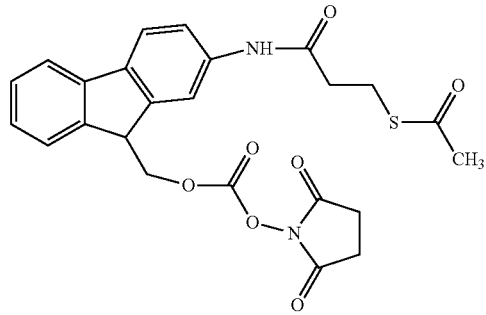
Precursor 6
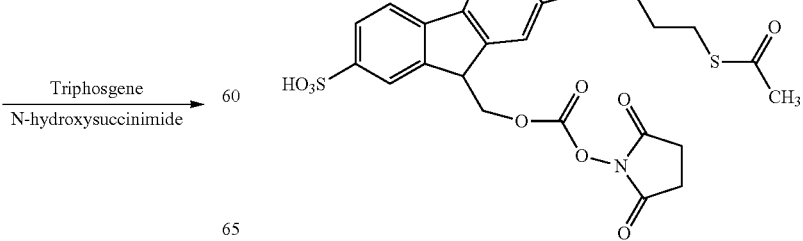

73
-continued
Precursor 7
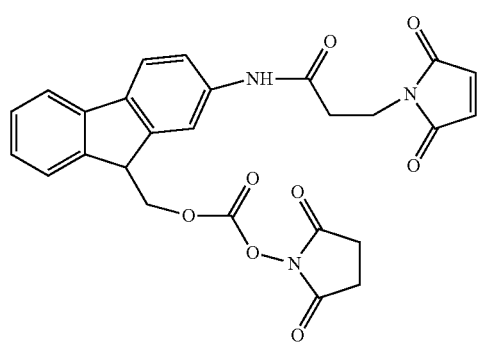
74
-continued
Precursor 8
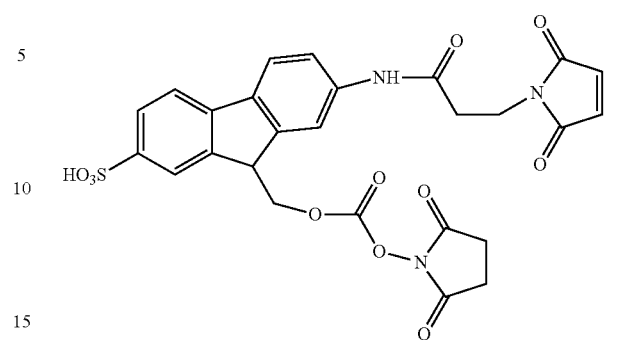
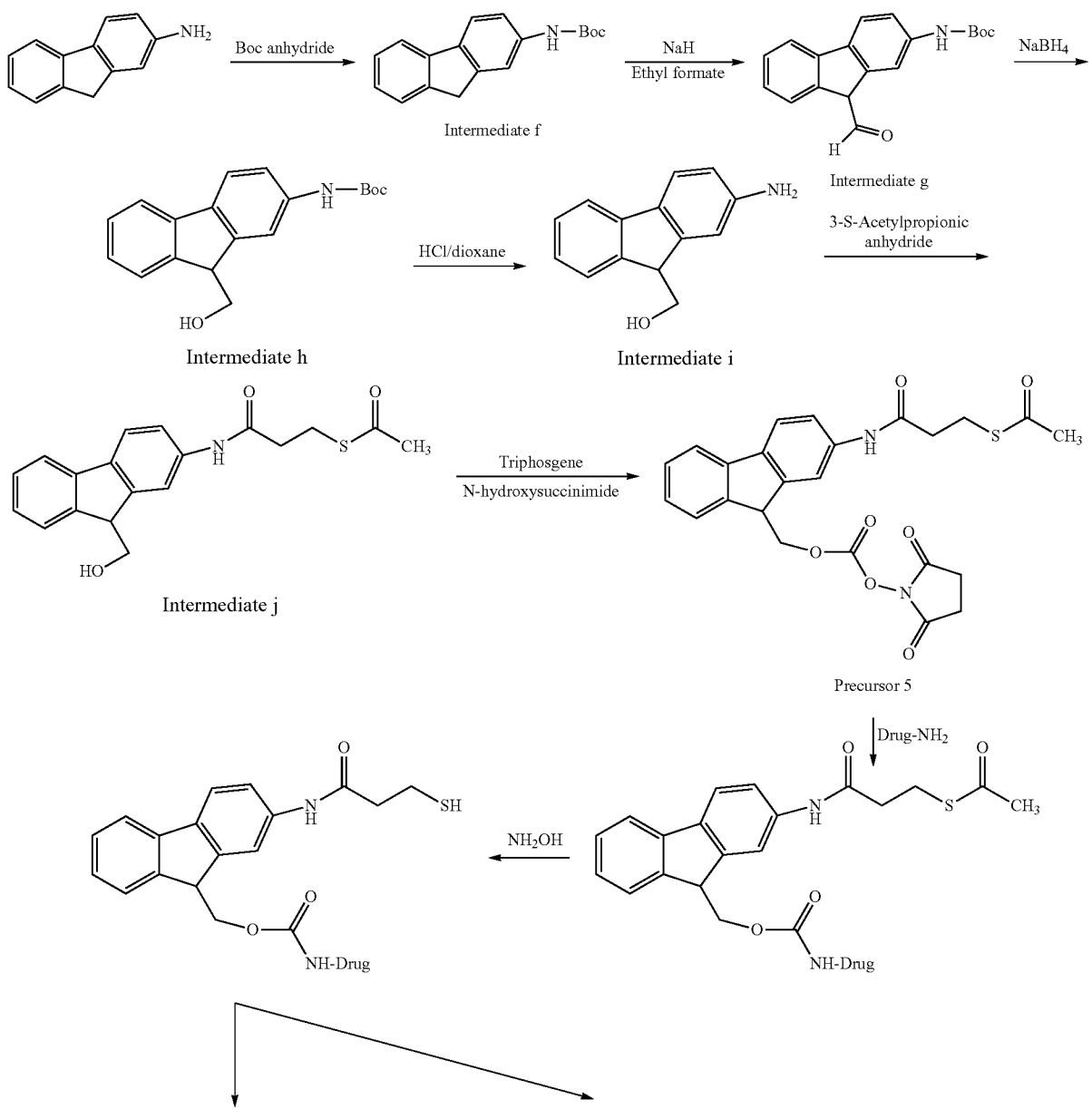
Scheme 4: Synthesis of Precursor 5

-continued
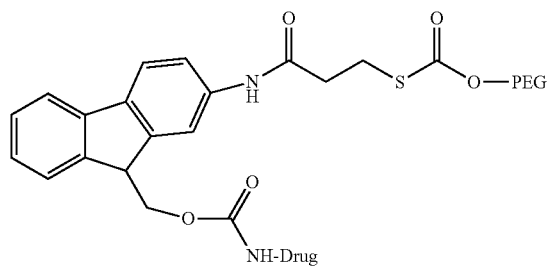
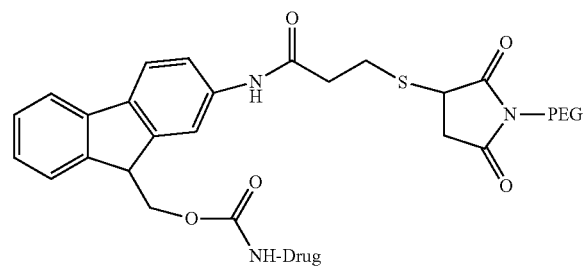
-continued
Scheme 5: Synthesis of Precursors 7 and 8
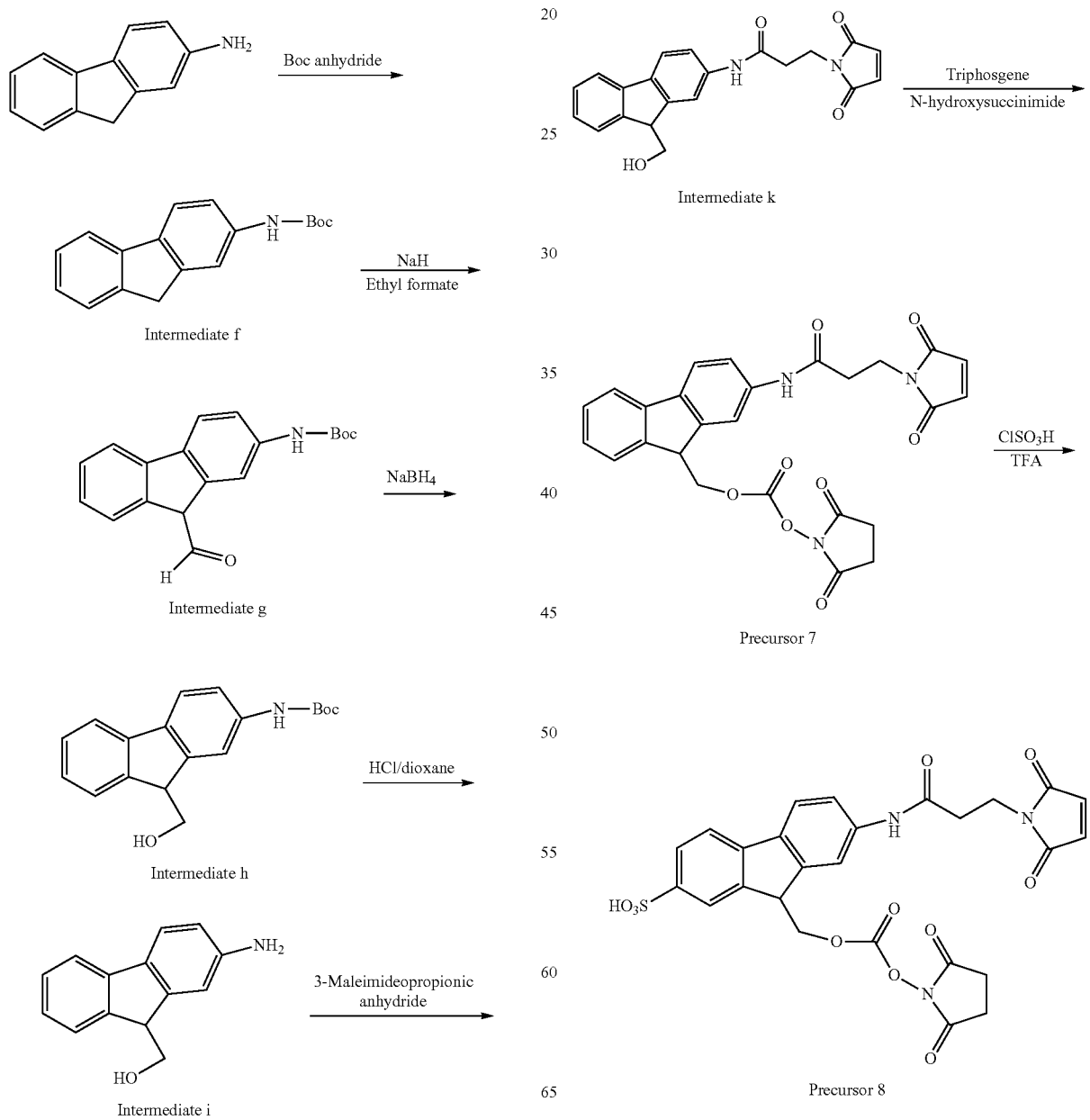

Scheme 6: Procedures for preparation of PEG—FMS-drugs
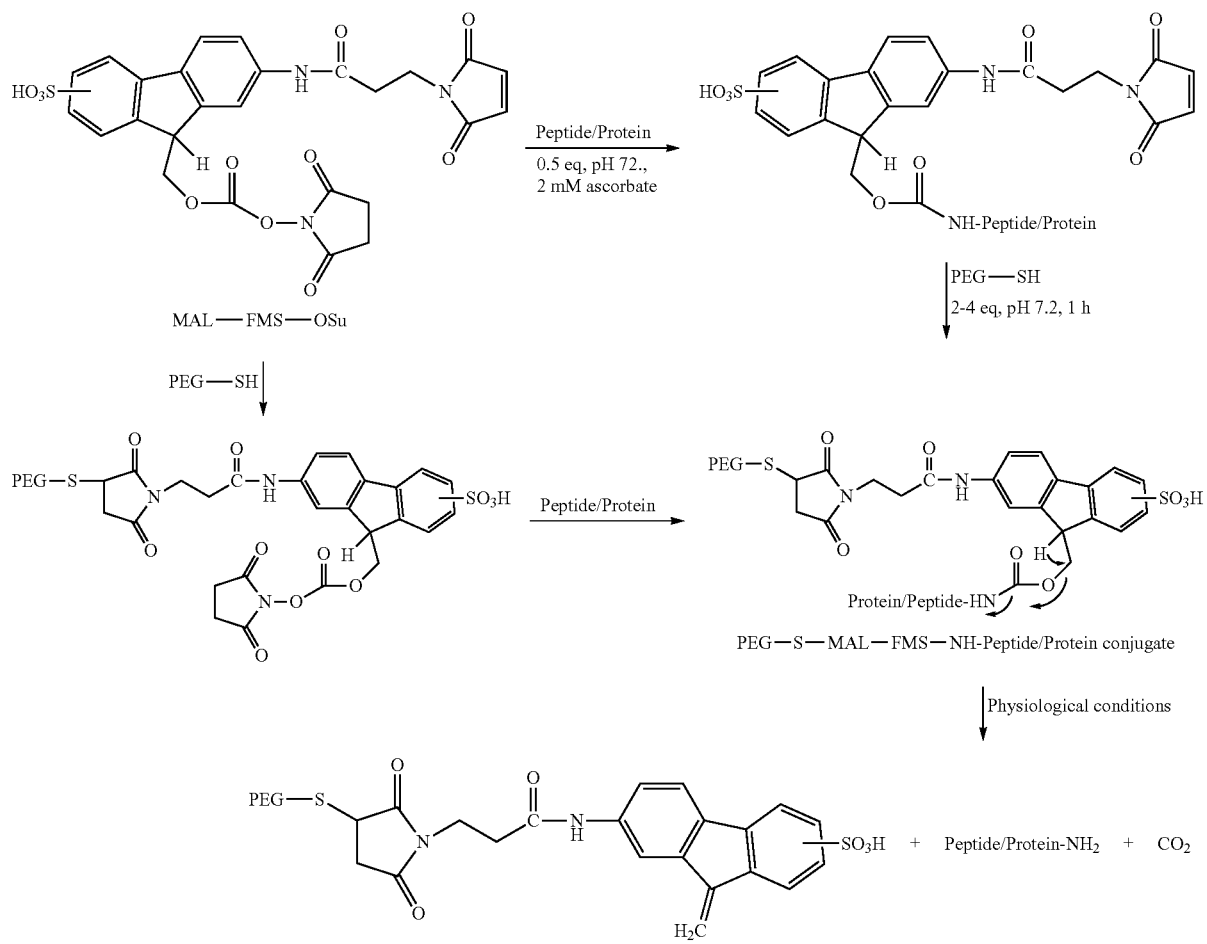
| Fmoc/FMS derivative | $R_5$-$R_6$—PEG | PEG derivative |
|---|---|---|
| Scheme 7 (page a) | | |
| 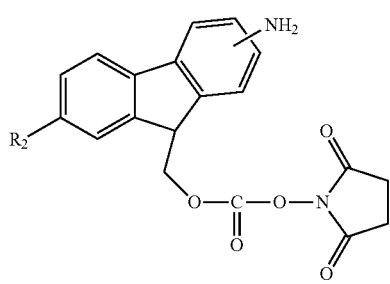 <br> $R_2$ is H or sulfo | —NH—CO—O—PEG | PEG—OCO—Cl |
| | —NH—CO—CH$_2$—NH$_2$—CO—NH—PEG | PEG—NH$_2$ |
| | —NH—CO—PEG | PEG—COOH |
| | —NH—CH$_2$—PEG | PEG—CHO |
| | —NH—CO—NH—PEG | PEG—N=C=O |
| | —NH—CS—NH—PEG | PEG—N=C=S |

| Fmoc/FMS derivative | $R_5$-$R_6$—PEG | PEG derivative |
|---|---|---|
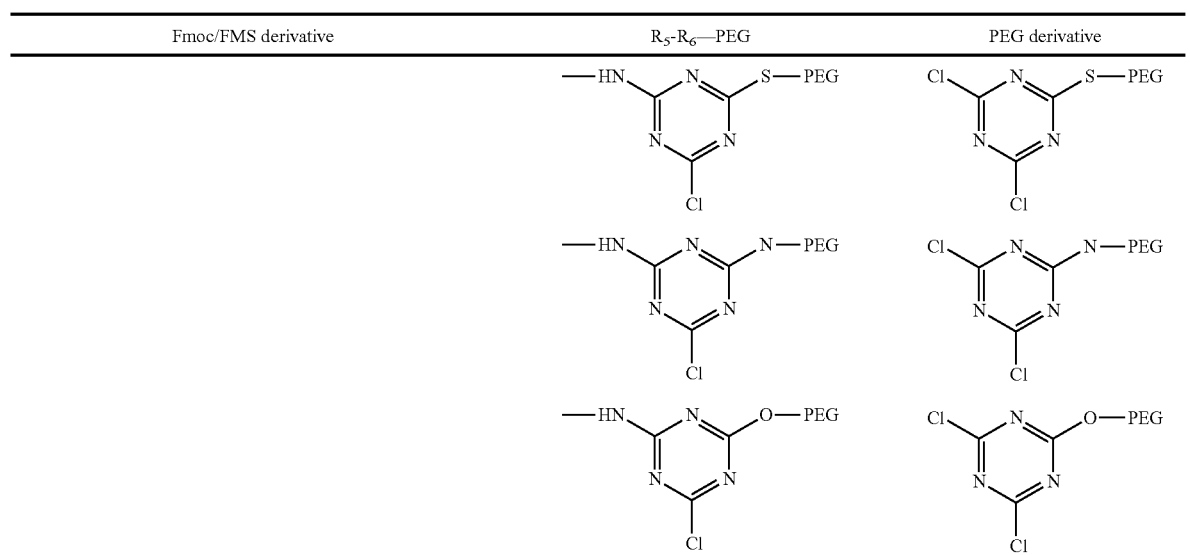
Sheme 7 (page b)
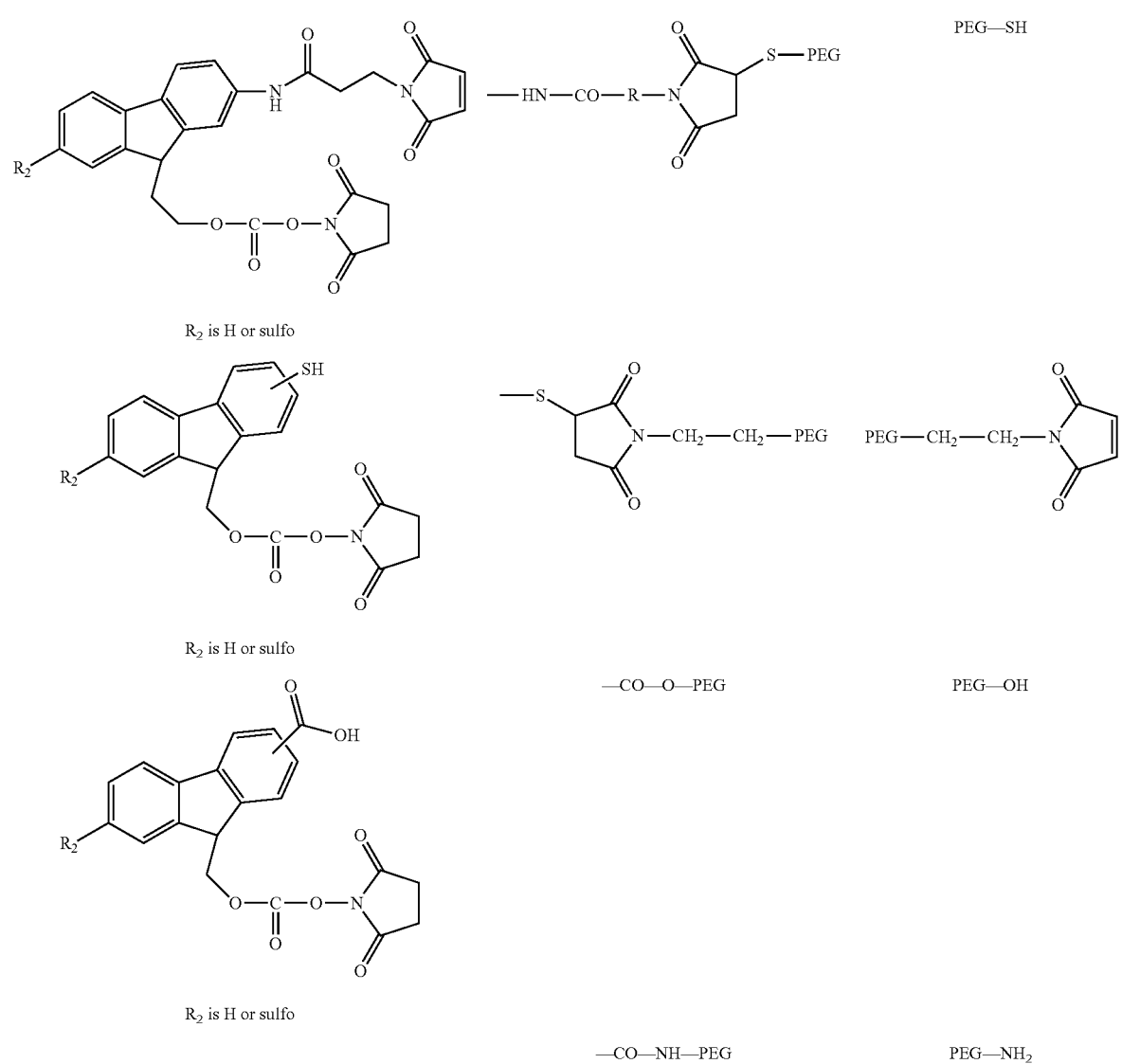

-continued
| Fmoc/FMS derivative | $R_5$-$R_6$—PEG | PEG derivative |
|---|---|---|
| Scheme 7 (page c) | | |
| 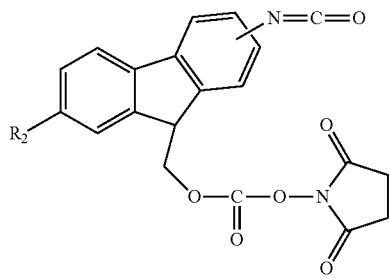 R$_2$ is H or sulfo | —NH—CO—NH—PEG | PEG—NH$_2$ |
| 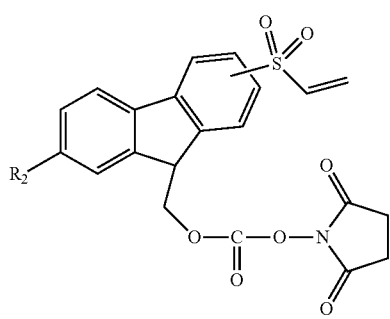 R$_2$ is H or sulfo | —SO$_2$—CH$_2$—CH$_2$—S—PEG | PEG—SH |
| 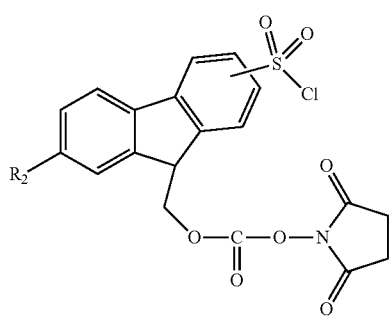 R$_2$ is H or sulfo | —SO$_2$—NH—PEG | PEG—NH |
| 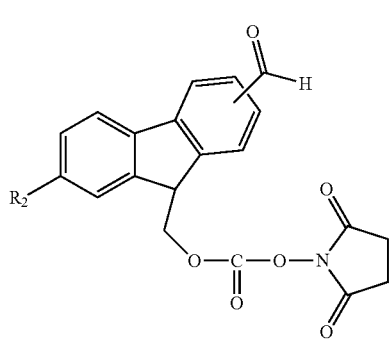 R$_2$ is H or sulfo | —CH$_2$—NH—PEG | PEG—NH$_2$ |

| Fmoc/FMS derivative | R₅-R₆—PEG | PEG derivative |
|---|---|---|
| Scheme 7 (page d) | | |
| [structure: fluorene with R-SO₂Cl group, R₂ substituent, and CH₂-O-C(=O)-O-NHS ester; R₂ is H or sulfo] | —PO₂—NH—PEG | PEG—NH₂ |
| | —PO₂—O—PEG | PEG—OH |
| [structure: fluorene with (CH₂)ₙ—Br, Cl, F, I group, R₂ substituent, and CH₂-O-C(=O)-O-NHS ester; R₂ is H or sulfo] | —(CH₂)ₙ₋₁—CH₂—NH—PEG | PEG—NH₂ |
| | —(CH₂)ₙ₋₁—CH₂—S—PEG | PEG—SH |

The invention claimed is:

1. A method for reduction of food intake and for treatment of obesity and diseases, conditions or disorders which can be alleviated by reduction of food intake, including hypertension, dyslipidemia, cardiovascular risk, insulin-resistance, and diabetes mellitus, said method comprising administering to an individual in need an effective amount of a conjugate of the formula:

$(X)_n$—Y wherein

Y is a PYY agonist; and

X is a radical of the formula (i):

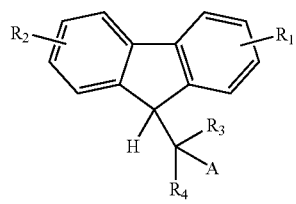

(i)

wherein $R_1$ is a radical of the formula —$R_5$—$R_6$-PEG, wherein PEG is a linear or branched polyethylene glycol (PEG) moiety;

$R_2$ is selected from the group consisting of hydrogen, (C1-C8)alkyl, (C1-C8) alkoxy, (C1-C8) alkoxyalkyl, (C6-C10) aryl, (C1-C8) alkaryl, (C6-C10) aryl, (C1-C8) alkyl, halogen, nitro, —$SO_3H$, —$SO_2NHR$, amino, ammonium, carboxyl, $PO_3H_2$, and $OPO_3H_2$, and R is selected from the group consisting of hydrogen, (C1-C8)alkyl and (C6-C10)aryl;

$R_3$ and $R_4$, the same or different, are each selected from the group consisting of hydrogen, (C1-C8) alkyl and (C6-C10) aryl;

$R_5$ is selected from the group consisting of —NH—, —S—, —CO—, —$CH_2$—, —$SO_2$—, and —$PO_2$—; and A is OCO— linked to an amino group of the PYY agonist; and n is an integer of at least one, provided that:

(i) when $R_5$ is —NH—, $R_6$ is —CO—, —COO—, —$CH_2$—, —$CH(CH_3)$—, —CO—NH—, —CS—NH, —CO—$CH_2$—NH—CO—, —CO—$CH(CH_3)$—NH—CO—, —CO—$CH_2$—NH—CO—NH,

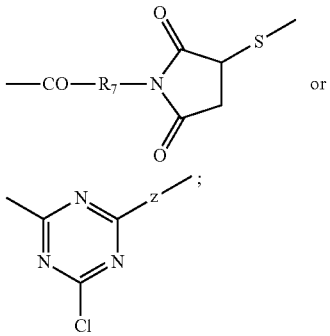

Z is O, S or NH that is linked to the PEG moiety; and $R_7$ is selected from the group consisting of C1-C18 straight or branched alkylene, phenylene, an oxyalkylene radical having 3-18 carbon atoms in the backbone, a residue of a peptide containing 2-10 amino acid residues, and a residue of a saccharide containing 1-10 monosaccharide residues;

(ii) when $R_5$ is —S—, $R_6$ is

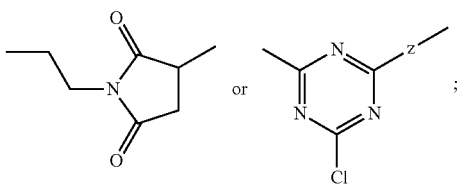

and Z is O, S or NH;

(iii) when $R_5$ is —CO—, $R_6$ is —O—, —NH—, —NH—$R_7$—COO—, —NH—$R_7$—NH, —NH—$R_7$—CO—NH,

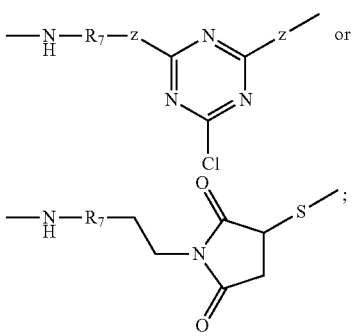

Z is O, S or NH; and $R_7$ is selected from the group consisting of C1-C18 straight or branched alkylene, phenylene, an oxyalkylene radical having 3-18 carbon atoms in the backbone, a residue of a peptide containing 2-10 amino acid residues, and a residue of a saccharide containing 1-10 monosaccharide residues;

(iv) when $R_5$ is $-CH_2-$, $R_6$ is $-(CH_2)_n-S-$ or $-(CH_2)_n-NH-$,
wherein n is 0 to 18;

(v) when $R_5$ is $-SO_2-$, $R_6$ is $-O-$; $-NH-$ or $-CH_2-CH_2-S$; and (vi) when $R_5$ is $-PO_2-$, $R_6$ is $-O-$ or $-NH-$.

2. The method of claim 1, wherein (i) $R_2$, $R_3$ and $R_4$ each is hydrogen; or (ii) $R_2$ is $-SO_3H$ at position 2 of the fluorine ring, and $R_3$ and $R_4$ each is hydrogen.

3. The method of claim 1, wherein said PYY agonist is $PYY_{3-36}$ [SEQ ID NO:12].

4. The method of claim 1, wherein $R_5$ is $-NH-$.

5. The method of claim 4, comprising administering a conjugate of the formula:

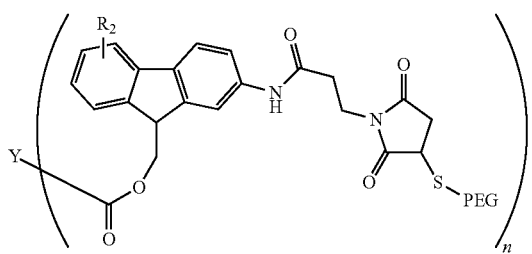

wherein $R_2$ is H or $-SO_3H$ at position 2 of the fluorene ring, and PEG is a linear or branched PEG moiety of molecular weight in the range of 200 to 200,000 Da.

6. The method of claim 5, wherein n is an integer from 1 to 3.

7. The method of claim 6, wherein the PEG moiety has a molecular weight in the range of 5,000 to 40,000 Da.

8. The method of claim 7, wherein the PEG moiety is a branched molecule of 40,000 Da or 5,000 Da.

9. The method of claim 6, wherein $R_2$ is $-SO_3H$ at position 2 of the fluorene ring, and the PEG moiety is a branched molecule of 40,000 Da.

10. The method of claim 4, comprising administering a conjugate of the formula:

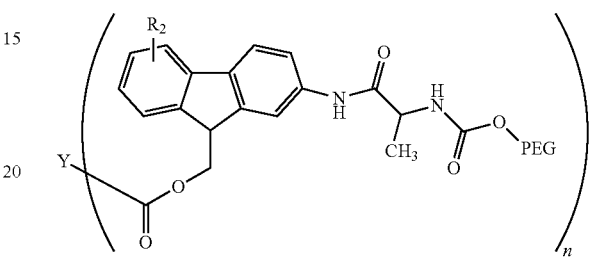

wherein $R_2$ is H or $-SO_3H$ at position 2 of the fluorene ring, and PEG is a linear or branched PEG moiety of molecular weight in the range of 200 to 200,000 Da.

11. The method of claim 10, wherein the PEG moiety has a molecular weight in the range of 5,000 to 40,000 Da.

12. The method of claim 11, wherein the PEG moiety is a branched molecule of 40,000 Da or 5,000 Da.

* * * * *